(12) United States Patent
Janetka et al.

(10) Patent No.: US 10,738,070 B2
(45) Date of Patent: Aug. 11, 2020

(54) MANNOSE-DERIVED ANTAGONISTS OF FIMH USEFUL FOR TREATING DISEASE

(71) Applicant: Fimbrion Therapeutics, Inc., St. Louis, MO (US)

(72) Inventors: James W. Janetka, St. Louis, MO (US); Laurel Mydock-McGrane, St. Louis, MO (US)

(73) Assignee: Fimbrion Therapeutics, Inc., St. Louis, MO (US)

( * ) Notice: Subject to any disclaimer, the term of this patent is extended or adjusted under 35 U.S.C. 154(b) by 0 days.

(21) Appl. No.: 16/087,305

(22) PCT Filed: Mar. 23, 2017

(86) PCT No.: PCT/US2017/023764
§ 371 (c)(1),
(2) Date: Sep. 21, 2018

(87) PCT Pub. No.: WO2017/165619
PCT Pub. Date: Sep. 28, 2017

(65) Prior Publication Data
US 2019/0106451 A1    Apr. 11, 2019

Related U.S. Application Data

(60) Provisional application No. 62/312,017, filed on Mar. 23, 2016.

(51) Int. Cl.
| C07H 15/26 | (2006.01) |
| C07H 15/203 | (2006.01) |
| A61K 31/7052 | (2006.01) |
| A61K 45/06 | (2006.01) |
| A61P 31/04 | (2006.01) |

(52) U.S. Cl.
CPC ....... *C07H 15/203* (2013.01); *A61K 31/7052* (2013.01); *A61K 45/06* (2013.01); *A61P 31/04* (2018.01); *C07H 15/26* (2013.01)

(58) Field of Classification Search
None
See application file for complete search history.

(56) References Cited

U.S. PATENT DOCUMENTS

| 6,153,396 | A | 11/2000 | Hultgren | |
| 6,962,791 | B2 | 11/2005 | Hultgren | |
| 7,790,183 | B2 | 9/2010 | Darouiche | |
| 8,937,167 | B2* | 1/2015 | Janetka | C07H 15/203 536/4.1 |
| 9,567,362 | B2* | 2/2017 | Janetka | A61K 31/7048 |
| 9,957,289 | B2* | 5/2018 | Janetka | A61K 45/06 |
| 10,273,260 | B2* | 4/2019 | Janetka | A01N 43/78 |
| 2007/0167378 | A1 | 7/2007 | Saraiva | |
| 2008/0171706 | A1 | 7/2008 | Berglund | |
| 2008/0268006 | A1 | 10/2008 | Molin | |
| 2010/0015600 | A1 | 1/2010 | Barnich | |
| 2012/0309701 | A1 | 12/2012 | Janetka | |
| 2014/0274930 | A1 | 9/2014 | Dietrich | |
| 2015/0175644 | A1 | 6/2015 | Ernst | |
| 2015/0197538 | A1 | 7/2015 | Janetka | |
| 2016/0145289 | A1 | 5/2016 | Janetka | |
| 2017/0247401 | A1 | 8/2017 | Janetka | |
| 2018/0194792 | A1 | 7/2018 | Janetka | |
| 2019/0211045 | A1 | 7/2019 | Janetka | |
| 2020/0002303 | A1 | 1/2020 | Janetka | |

FOREIGN PATENT DOCUMENTS

| EP | 0383092 | 8/1990 | |
| WO | 1995014028 | 5/1995 | |
| WO | 2001100386 | 2/2001 | |
| WO | 2005089733 | 9/2005 | |
| WO | 2011050323 | 4/2011 | |
| WO | 2011073112 | 6/2011 | |
| WO | 2012109263 | 8/2012 | |
| WO | 2012164074 | 12/2012 | |
| WO | 2014194270 | 12/2014 | |
| WO | WO-2014194270 A1 * | 12/2014 | ......... A61K 31/7064 |
| WO | 2017156508 | 9/2017 | |
| WO | 2017165619 | 9/2017 | |

OTHER PUBLICATIONS

Wolff, Manfred E. "Burger's Medicinal Chemistry, 5ed, Part I", John Wiley & Sons, 1995, pp. 975-977. (Year: 1995).*
Banker, G.S. et al, "Modern Pharmaceutics, 3ed.", Marcel Dekker, New York, 1996, p. 596 (Year: 1996).*
International Application No. PCT/US2017/021983; International Preliminary Report on Patentability, dated Sep. 11, 2018; 7 pages.
International Application No. PCT/US2017/021983; International Search Report and Written Opinion of the International Searching Authority, dated Jul. 18, 2017; 15 pages.
International Application No. PCT/US2017/023764; International Preliminary Report on Patentability, dated Sep. 25, 2018; 6 pages.
International Application No. PCT/US2017/023764; International Search Report and Written Opinion of the International Searching Authority, dated Jun. 20, 2017; 8 pages.
Pang, et al., "FimH Antagonists: Structure-Activity and Structure-Property Relationships for Biphenyl α-D-Mannopyranosides," ChemMedChem 2012, vol. 7, pp. 1404-1422, p. 1408.
U.S. Appl. No. 16/084,177; Application as filed, dated Sep. 11, 2018; 133 pages.
Abdel-Megeid, F. et al., "Preparation and Some Reactions of 0-Glucosyl Derivatives of 2-Thioxo-1,3,4-Oxadiazoles and 2-Thioxo-1,3,4-Thiadiazoles and Their 2-Oxo Analogues", Carbohydrate Res., 59(1):95-102, (1977).

(Continued)

*Primary Examiner* — Traviss C McIntosh, III
(74) *Attorney, Agent, or Firm* — Dennis A. Bennett; Brock D. Levin

(57) ABSTRACT

The present invention relates to mannoside derivative compounds useful as inhibitors of FimH and methods for the treatment or prevention of urinary tract infection.

7 Claims, 2 Drawing Sheets

(56) References Cited

OTHER PUBLICATIONS

Abgottspon, D. et al., "Development of an Aggregation Assay to Screen FimH Antagonists", J Microb Methods, 82(3):249-55, (2010).
Abgottspon, D. et al., "In Vivo Evaluation of FimH Antagonists—A Novel Class of Antimicrobials for the Treatment of Urinary Tract Infection", Chimia, 66(4):166-9, (2012).
Bognar, R. et al., "N-Glycosyl Derivatives: Part III. The Subsequent Installation of the Aglycone. Synthesis of N-Glycosyl Derivatives of 2-Amino-Thiazole, 2-Amino-1 ,3,4-Thiadiazole and 5-Amino-1 ,2,3,4-Thiatriazols", Carbohy Res., 5:320-328, (1967).
Bouckaert, J. et al., "Receptor Binding Studies Disclose a Novel Class of High-Affinity Inhibitors of the *Escherichia coli* FimH Adhesion", Mol Microbiol., 55(2):441-55, (2005).
Cusumano, C. et al., "Treatment and Prevention of Urinary Tract Infection with Orally Active FimH Inhibitors", Sci Transl Med., 3(109):109ra115, (2011).
Durka, M. et al., "The Functional Valency of Dodecamannosylated Fullerenes with *Escherichia coli* FimH-Towards Novel Oacterial Antiadhesives", Chem Commun., 47(4):1321-3, (2011).
Firon, N. et al., "Aromatic Alpha-Glycosides of Mannose Are Powerful Inhibitors of the Adherence of Type 1 Fimbriated *Escherichia coli* to Yeast and Intestinal Epitherlial Cells", Infect Immun., 55(2):472-6, (1987).
Firon, N. et al., "Interaction of Mannose-Containing Oligosaccharides With the Fimbrial Lectin of *Escherichia coli*", Biochem and Biophys Res Commun., 105(4):1426-32, (1982).
Furneaux, R. et al., "New Mannotriosides and Trimannosides as Potential Ligands for Mannose-Specific Binding Oroteins", Can J Chem., 80:964-72, (2002).
Gouin, S. et al., "Synthetic Multimeric Heptyl Mannosides as Potent Antiadhesives of Uropathogenic *Escherichia coli*", Chem Med Chem., 4(5):749-55, (2009).
Grabosch, C. et al., "Squaric Acid Monoamide Mannosides as Ligands for the Bacterial Lectin FimH: Covalent nhibition or Not?", Chem Bio Chem., 12(7):1066-74, (2011).
Guiton, P. et al., "Combinatorial Small-Molecule Therapy Prevents Uropathogenic *Escherichia coli* Catheter-Associated Urinary Tract Infections in Mice", Antimicrob Agents Chemother., 56(9):4738-45, (2012).
Han, Z. et al., "Lead Optimization Studies on FimH Antagonists: Discovery of Potent and Orally Bioavailable Ortho-Substituted Biphenyl Mannosides", J Med Chem., 55(8):3945-59, (2012).
Han, Z. et al., "Structure-Based Drug Design and Optimization of Mannoside Bacterial FimH Antagonists", J Med Chem., 43(12):4779-92, (2010).
Hartmann, M. et al., "The Bacterial Lectin FimH, a Target for Drug Discovery—Carbohydrate Inhibitors of Type 1 Fimbriae-Mediated Bacterial Adhesion", Eur J Org Chem., 2011(20-21):1-28, (2011).
Haskins, W. et al., "Relations Between Rotatory Power and Structure in the Sugar Group; Some 2'-Naphthyl L-Thioglycopyranosides and their Acetates", J Am Chem Soc., 69(7):1668-72, (1947).
Hung, C. et al., "Structural Basis of Tropism of *Escherichia coli* to the Bladder During Urinary Tract Infection", Mol Microb., 44(4):903-15, (2002).
International Application No. PCT/US2010/053848; International Search Report and Written Opinion of the International Searching Authority, dated Dec. 23, 2010; 8 pages.
International Application No. PCT/US2012/024169; Intenational Search Report and Written Opinion and Written Opinion of the International Searching Authority, dated May 29, 2012; 7 pages.
International Application No. PCT/US2014/040355; Intenational Search Report and Written Opinion of the International Searching Authority, dated Sep. 22, 2014; 11 pages.
Irani, R. et al., "Stannic Chloride Promoted Synthesis of Mannosides", Indian J Chem., Sect. B: Org. Chem. Incl. Med. Chem. 30(5):519-21, (1991), (abstract only).
Jiang, X. et al., "Antiadhesion Therapy for Urinary Tract Infections—A Balanced PK/PD Profile Proved to Be Key for Success", J Med Chem., 55(10):4700-13, (2012).
Klein, T. et al., "FimH Antagonists for the Oral Treatment of Urinary Tract Infections: From Design and Synthesis to in Vitro and in Vivo Evaluation", J Med Chem., 53(24):8627-41, (2010).
Kostakioti, M. et al., "Distinguishing the Contribution of Type 1 Pili from That of other QseB-Misregulated Factors When QseC Is Absent during Urinary Tract Infection", Infect Immun., 80(8):2826-34, (2012).
Lindhorst, T. et al., "Inhibition of the Type 1 Fimbriae-Mediated Adhesion of *Escherichia coli* to Erythrocytes by Multiantennary [alpha]-mannosyl Clusters: The Effect of Multivalency", Glycoconj J., 15(6):605-13, (1998).
Mydock-McGrane, L. et al., "Antivirulence C-Mannosides as Antibiotic-Sparing, Oral Therapeutics for Urinary Tract Infections", J Med Chem., 59(20):9390-408, (2016).
Nagahori, N. et al., "Inhibition of Adhesion of Type 1 Fimbriated *Escherichia coli* to Highly Mannosylated Ligands", ChemBioChem, 3(9):836-44, (2002).
Qian, X. et al., "Arrays of Self-Assembled Monolayers for Studying Inhibition of Bacterial Adhesion", Anal Chem., 74(8):1805-10, (2002).
Rabbani, S. et al., "Expression of the Carbohydrate Recognition Domain of FimH and Development of a Competitive Binding Assay", Anal Biochem., 407(2):188-95, (2010).
Sattigeri, J. et al., "Synthesis and Evaluation of Thiomannosides, Potent and Orally Active FimH Inhibitors", Bioorg Med Chem Lett., 28(17):2993-7, (2018).
Scharenberg, M. et al., "Target Selectivity of FimH Antagonists", J Med Chem., 55(22):9810-6, (2012).
Scharenberg, M. et al., "A Flow Cytometry-Based Assay for Screening FimH Antagonists", Assay Drug Dev Technol., 9(5):455-65, (2011).
Schwardt, O. et al., "Design, Synthesis and Biological Evaluation of Mannosyl Triazoles as FimH Antagonists", Bioorg Med Chem., 19(21):6454-73, (2011).
Shuman, D. et al., "Synthesis and Biological Activity of Certain 8-Mercaptopurine and 6-Mercaptopyrimidine S-Nucleosides", J Med Chem., 12(4):653-7, (1969).
Sperling, O. et al., "Evaluation of the Carbohydrate Recognition Domain of the Bacterial Adhesion FimH: Design, Synthesis and Binding Properties of Mannoside Ligands", Org Biomol Chem., 4(21):3913-22, (2006).
Stoll, Van A. et al., "The Furocoumarin and the Beta-D-Glucosido-Furocumarinsaure from the Seeds of *coronilla* Species", Helvetica Chimica Acta, 33(211-2):1637-47, (1950), (with English abstract).
Taile, V. et al., "Synthesis and Biological Evaluation of Novel 2□(4□O□ β□D□glucosidoxyphenyl)□ 4,5-Disubstituted Imidazoles", J Heterocyclic Chem., 47(4):903-7, (2010).
Touaibia, M. et al., "Glycodendrimers as Anti-Adhesion Drugs Against Type 1 Fimbriated *E. coli* Uropathogenic Infections", Mini Rev Med Chem., 7(12):1270-83, (2007).
Touaibia, M. et al., "Mannosylated G(0) Dendrimers with Nanomolar Affinities to *Escherichia coli* FimH", ChemMedChem., 2(8):1190-1201, (2007).
Touaibia, M. et al., "Tri- and Hexavalent Mannoside Clusters as Potential Inhibitors of Type 1 Fimbriated Bacteria Using Pentaerythritol and Triazole Linkages", Chem Commun., (4):380-2, (2007).
U.S. Appl. No. 13/453,991; Notice of Allowance, dated Jul. 14, 2014; 4 pages.
U.S. Appl. No. 13/453,991; Notice of Allowance, dated Sep. 4, 2014; 4 pages.
U.S. Appl. No. 13/453,991; Office Action, dated Mar. 6, 2014; 9 pages.
U.S. Appl. No. 13/453,991; Office Action, dated Nov. 20, 2013; 12 pages.
U.S. Appl. No. 14/570,322; Notice of Allowance, dated Sep. 9, 2016; 7 pages.
U.S. Appl. No. 14/570,322; Office Action, dated May 20, 2016; 8 pages.
U.S. Appl. No. 14/894,927; Notice of Allowance, dated Aug. 16, 2017; 5 pages.
U.S. Appl. No. 14/894,927; Notice of Allowance, dated Dec. 8, 2017; 7 pages.

(56) References Cited

OTHER PUBLICATIONS

U.S. Appl. No. 14/894,927; Office Action, dated Mar. 3, 2017; 10 pages.
U.S. Appl. No. 15/373,260; Notice of Allowance, dated Jul. 2, 2018; 4 pages.
U.S. Appl. No. 15/373,260; Notice of Allowance, dated Nov. 21, 2018; 7 pages.
U.S. Appl. No. 15/373,260; Notice of Allowance, dated Oct. 23, 2018; 7 pages.
U.S. Appl. No. 15/373,260; Office Action, dated Feb. 26, 2018; 5 pages.
U.S. Appl. No. 15/915,490; Office Action, dated Aug. 29, 2019; 12 pages.
U.S. Appl. No. 16/353,824; Office Action, dated Nov. 6, 2019; 7 pages.
Walter, M. et al., "A Modular System for the Preparation of Diazirine-Labeled Mannose Derivatives Using Thiourea Bridging", Synthesis, 6:952-8, (2006).
Wellens, A. et al., "Intervening with Urinary Tract Infections Using Anti-Adhesives Based on the Crystal Structure of the FimH-Oligomannose-3 Complex", PLoS ONE, 3(4):e2040, (2008).

* cited by examiner

MANNOSE-DERIVED ANTAGONISTS OF FIMH USEFUL FOR TREATING DISEASE

This application claims priority to U.S. provisional application No. 62/312,017 filed Mar. 23, 2016, the disclosure of which is incorporated by reference herein in its entirety.

Disclosed herein are new O-mannoside compounds and compositions and their application as pharmaceuticals for the treatment of disease. Methods of inhibition of FimH activity in a human or animal subject are also provided for the treatment diseases such as urinary tract infection.

Urinary tract infection (UTI) caused by uropathogenic *Escherichia coli* (UPEC) is one of the most common infectious diseases in women. The morbidity and economic impact are enormous, with over $2.5 billion spent annually on treatment. Further, recurrent infections are a significant problem despite appropriate antibiotic therapy of the initial infection case. The high rates of recurrence, and the large numbers of women that end up in urology clinics due to their chronic recurrent UTIs, highlights the need for a better understanding of the pathogenic mechanisms involved in this disease and the development of new and better therapies.

Gram-negative bacteria such as UPEC are the causative agents of a wide variety of acute and chronic infectious diseases. Many of these infections are initiated by a critical interaction between host ligands (frequently polysaccharide moieties) and bacterial adhesins (frequently expressed at the distal tip of polymeric pilus fibers assembled by the chaperone/usher pathway). The mannose binding FimH adhesin of type 1 pili is critical for the colonization and invasion into the bladder epithelium. After invasion, UPEC are able to rapidly multiply inside superficial umbrella cells of the bladder forming biofilm-like intracellular bacterial communities (IBCs). Upon maturation, bacteria disperse from the IBC, spread to neighboring cells, and form next generation IBCs. This is the mechanism by which UPEC rapidly amplify in numbers in the urinary tract and cause disease.

Type 1 pili are largely composed of repeating FimA protein subunits which form a helically wound cylinder that comprises the thick pilus rod. Following the pilus rod the distal flexible tip fibrillum is composed of one copy of FimF, FimG, and finally the tip adhesin FimH. The tip protein FimH is comprised of two domains, a pilin domain (FimHP), which allows it to incorporate into the pilus, and an adhesin lectin domain (FimHL) that contains a conserved mannose binding pocket, which mediates binding to mannose. It is this interaction with mannosylated host proteins that is believed to mediate attachment to host cells and result in both acute and chronic disease in both urinary tract infections (UTIs) and Crohn's disease. The X-ray crystal structure of FimH bound to mannose showed that mannose is bound in a negatively charged pocket on FimH. The mannose binding site is highly conserved as it is invariant in 300 fimH genes sequenced from clinical UPEC strains. Thus, FimH is the critical node of the entire UPEC pathogenic cascade.

To elucidate the molecular details of UPEC (uropathogenic *E. coli*) pathogenesis, several murine models of infection have been established which recapitulate many of the clinical manifestations often seen in humans. These models include acute UPEC infections, chronic and/or recurrent infections, and catheter-associated UTI. In all of these models the adhesin FimH has been shown to play an integral role in pathogenesis and is required to cause disease, highlighting it as an excellent therapeutic target. The fundamental interaction between FimH is believed to occur with the host mannosylated uroplakins that coat the luminal surface of the bladder. This initial binding facilitates colonization of the bladder epithelium and invasion of the bacteria into the uroepilthelial cells. Once internalized, a single bacterium that escapes into the host cell cytoplasm can rapidly replicate and progress to form a biofilm-like intracellular bacterial community (IBC). Once these communities reach maturation they are able disperse and escape from the cell, filamenting to evade neutrophil phagocytosis. These filamentous bacteria can then go on to infect neighboring cells, reinitiating IBC formation and the pathogenic cycle. Importantly, evidence of IBCs and bacterial filaments has been observed in the urine of women suffering with an acute UTI, supporting the validity of the mouse model in recapitulating human disease.

In contrast to UTI, which is primarily mediated by a bacterial pathogen, the disease manifested in patients suffering from idiopathic inflammatory bowel disease (IBD), such as Crohn's disease (CD) and ulcerative colitis (UC), is the result of a complex interplay between a genetically susceptible host, a dysfunctional immune system, and a microbial component. Examination of biopsied tissue from patients suffering from CD and UC has highlighted an increase in the abundance of *E. coli* associated with gut mucosa. Analysis of these bacteria has resulted in discovery of a distinct pathotype known as adherent and invasive *E. coli* (AIEC). Identification of AIEC and their putative role in CD and UC has led to a number of follow up studies by several independent groups examining the intestinal microbiota in patients with IBD. This work has provided substantial evidence for the overgrowth of AIEC in ileal CD patients, with less convincing data for other IBD subtypes, including UC, colonic CD, and ileocolonic CD. Analysis of ileal enterocytes isolated from CD patients identified abnormal expression of the host receptor carcinoembryonic antigen-related cell adhesion molecule 6 (CEACAM6), which is highly mannosylated and been demonstrated to facilitate binding of AIEC to these cells via type 1 pili. Interestingly, adherence and invasion of AIEC into intestinal epithelial cells leads to increased expression of the receptor CECAM6, suggesting AIEC are able to promote their own colonization of the ileum in CD patients. Utilization of a transgenic mouse expressing human CEA family gene cluster, including CECAM6, results in increased colonization of AIEC, which recapitulates many of the clinical symptoms of CD including severe colitis, weight loss, and in this model decreased survival. Furthermore, these symptoms can be completely abolished through the administration of an anti-CECAM6 antibody or through the genetic deletion of FimH in the bacterial strain. Demonstrating a direct link between the recognition of CECAM6 by FimH and disease progression.

The X-ray crystal structure of FimH bound to a-D-mannose showed that mannose is bound in a negatively charged pocket of the FimH lectin domain (FimHL). The mannose binding site is highly conserved as it is invariant in over 300 fimH genes sequenced from clinical UPEC strains. Thus, FimH is the critical node of the entire UPEC pathogenic cascade in UTI.

Recurrence is a serious problem for many women. Women who present with an initial episode of acute UTI have a 25-44% chance of developing a second and a 3% chance of experiencing three episodes within six months of the initial UTI. Recurrence occurs despite appropriate antibiotic treatment and clearance of the initial infection from the urine. A large percentage of recurrent UTI are caused by the same strain of bacteria as the initial infection. One study followed 58 women and found that 68% of recurrences were caused by the same initial index strain of UPEC as determined by restriction fragment length polymorphism (RFLP) analysis. In a separate study, 50% of recurrent strains isolated from female college students appeared genotypically identical to the bacterial strain corresponding to the initial UTI. Another long-term prospective study demonstrated that the same strain of UPEC can cause a recurrent UTI up to 3 years later. The high frequency of same-strain recurrences supports the notion that a UPEC reservoir can exist in the affected individual. The inventors have shown that a quiescent intracellular reservoir (QIR) can form in the bladder tissue itself after acute infection and persist even after antibiotic therapy and urine cultures become sterile. Thus, reactivation of bacteria in QIRs may also be a contributing factor in recurrent UTIs.

Therefore, there is a need for effective treatments that can treat urinary tract infections and prevent the formation of quiescent intracellular reservoirs that are the source of so many recurrent infections.

Novel compounds and pharmaceutical compositions, certain of which have been found to inhibit FimH have been discovered, together with methods of synthesizing and using the compounds including methods for the treatment of FimH-mediated diseases in a patient by administering the compounds.

In certain embodiments of the present invention, compounds have structural Formula I:

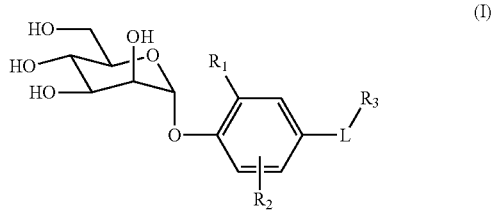

(I)

or a salt, ester, or prodrug thereof, wherein:

$R_1$ is chosen from $CH_3$, cyclopropyl, CN, $CF_3$, $OCH_3$, OAc, halogen, $NH_2$, $NHR_4$;

$R_2$ is chosen from H, $NO_2$, $NH_2$, $NHR_4$;

L is absent, or O, S, $NR_x$;

$R_3$ is an aryl, heterocyclyl, or heteroaryl group, any of which may be optionally substituted with cycloalkyl, heterocycloalkyl, halogen, oxo, $OR_{12}$, $SR_{12}$, $NHR_{12}$, CN, COOH, $CO_2$alkyl, $NO_2$, NHCO-alkyl, $SO_2C_{1-4}$alkyl, $SO_2$cycloalkyl, $SO_2NR_7R_8$, $CONR_7R_8$, and $C_{1-4}$alkyl, or an aryl or heteroaryl group optionally substituted with one or more of the following:

halogen, CN, COOH, $NH_2$, $CF_3$, $NO_2$, and $C_{1-4}$alkyl;

each $R_4$ is independently chosen from alkyl optionally substituted with OH, alkoxy, $NH_2$, NHalkyl, cycloalkyl, heterocyclyl, aryl, or heteroaryl;

each $R_7$ and $R_{12}$ is independently chosen from H, aryl, heteroaryl, alkyl optionally substituted with cycloalkyl, heterocycloalkyl, halogen, oxo, $OR_{12}$, $SR_{12}$, $NHR_{12}$, CN, COOH, $CO_2$alkyl, $NO_2$, NHCO-alkyl, $SO_2C_{1-4}$alkyl, $SO_2$cycloalkyl, $SO_2NR_7R_8$, $CONR_7R_8$, and $C_{1-4}$alkyl, or an aryl or heteroaryl group optionally substituted with one or more of the following:

halogen, CN, COOH, $NH_2$, $CF_3$, $NO_2$, and $C_{1-4}$alkyl;

$R_8$ is chosen from $C_{2-8}$alkyl, aryl, heterocycloalkyl, heteroaryl, and alkylNHCOalkyl-Cyanine5.5;

or $R_7$ and $R_8$ together form a heterocycloalkyl ring optionally substituted with alkyl; and $R_x$ is H, alkyl optionally substituted with OH, $NH_2$, $CO_2H$, $CONH_2$, $CO_2Me$, CN, $N_3$, alkoxy, $SO_2$alkyl, $SO_2NH_2$, COalkyl, and $CONH_2$.

Certain compounds disclosed herein may possess useful FimH inhibiting activity, and may be used in the treatment or prophylaxis of a disease or condition in which FimH plays an active role. Thus, in broad aspect, certain embodiments also provide pharmaceutical compositions comprising one or more compounds disclosed herein together with a pharmaceutically acceptable carrier, as well as methods of making and using the compounds and compositions. Certain embodiments provide methods for inhibiting FimH. Other embodiments provide methods for treating a FimH-mediated disorder in a patient in need of such treatment, comprising administering to said patient a therapeutically effective amount of a compound or composition according to the present invention. Also provided is the use of certain compounds disclosed herein for use in the manufacture of a medicament for the treatment of a disease or condition ameliorated by the inhibition of FimH.

In certain embodiments, the compounds have structural Formula II:

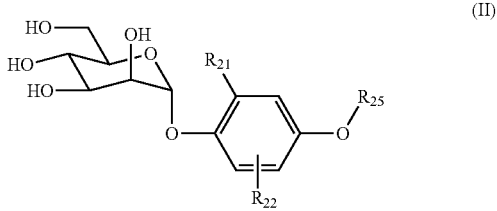

(II)

or a salt, ester, or prodrug thereof, wherein:

$R_{21}$ is chosen from $CH_3$, cyclopropyl, CN, $CF_3$, $OCH_3$, OAc, halogen, $NH_2$, $NHR_{24}$;

$R_{22}$ is chosen from H, $NO_2$, $NH_2$, $NHR_{24}$;

each $R_{24}$ is independently chosen from alkyl optionally substituted with OH, alkoxy, $NH_2$, NHalkyl, cycloalkyl, heterocyclyl, aryl, or heteroaryl;

and $R_{25}$ is an aryl or heteroaryl group optionally substituted with one or more of the following:

halogen, CN, COOH, $NH_2$, $NO_2$, NHCO-alkyl, NHalkyl, $SO_2C_{1-4}$alkyl, and $C_{1-4}$alkyl.

In certain embodiments, the compounds have structural Formula III:

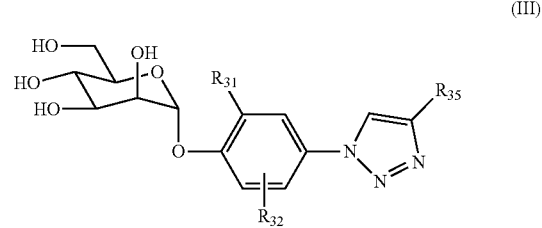

(III)

or a salt, ester, or prodrug thereof, wherein:

$R_{31}$ is chosen from $CH_3$, $CF_3$, $OCH_3$, OAc, halogen, $NH_2$, $NHR_{34}$;

$R_{32}$ is chosen from H, $NO_2$, $NH_2$, $NHR_{34}$;

each $R_{34}$ is independently chosen from alkyl, aryl, and heteroaryl;

and R$_{35}$ is an alkyl, cycloalkyl, heterocycloalkyl, aryl or heteroaryl group optionally substituted with one or more of the following:

halogen, CN, COOH, NH$_2$, NO$_2$, and C$_{1-4}$alkyl.

In certain embodiments, the compounds have structural Formula IV:

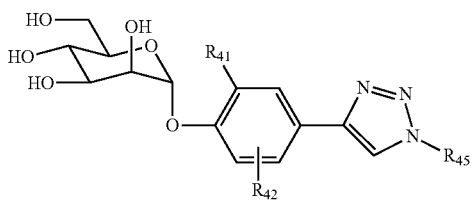

or a salt, ester, or prodrug thereof, wherein:

R$_{41}$ is chosen from CH$_3$, CF$_3$, OCH$_3$, OAc, halogen, NH$_2$, NHR$_{44}$;

R$_{42}$ is chosen from H, alkyl, NO$_2$, NH$_2$, NHR$_{44}$;

each R$_{44}$ is independently chosen from alkyl, aryl, and heteroaryl;

and R$_{45}$ is an alkyl, cycloalkyl, heterocycloalkyl, aryl or heteroaryl group optionally substituted with one or more of the following:

halogen, CN, COOH, NH$_2$, NO$_2$, and C$_{1-4}$alkyl.

In certain embodiments, the compounds have structural Formula V:

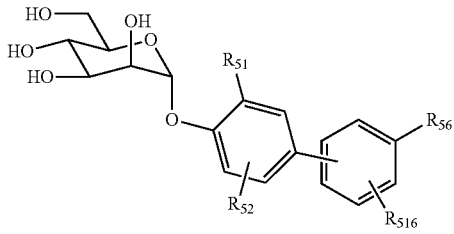

or a salt, ester, or prodrug thereof, wherein:

R$_{51}$ is chosen from CH$_3$, CF$_3$, OCH$_3$, OAc, halogen, NH$_2$, NHR$_{54}$;

R$_{52}$ is chosen from H, NO$_2$, NH$_2$, NHR$_{54}$, and alkyl;

each R$_{54}$ is independently chosen from alkyl, COR$_{510}$, SO$_2$R$_{511}$, aryl, and heteroaryl;

R$_{56}$ is chosen from CN, CO$_2$alkyl, halogen, aryl, heteroaryl, SO$_2$alkyl, SO$_2$cycloalkyl, SO$_2$NR$_{57}$R$_{58}$, and CONR$_{57}$R$_{58}$;

each R$_{57}$ and R$_{512}$ is independently chosen from H, alkyl optionally substituted with halogen, CN, COOH, NH$_2$, NO$_2$, and C$_{1-4}$alkyl, aryl, and heteroaryl;

R$_{58}$ is chosen from C$_{2-8}$alkyl, aryl, heterocycloalkyl, heteroaryl, and alkylNHCOalkyl-Cyanine5.5;

or

R$_{57}$ and R$_{58}$ together form a heterocycloalkyl ring;

R$_{510}$ and R$_{511}$ are each independently selected from alkyl, cycloalkyl, heterocycloalkyl, aryl, and heteroaryl;

R$_{516}$ is chosen from H, OR$_{512}$, SR$_{512}$, NHR$_{512}$, COOR$_{517}$ and CONR$_{518}$R$_{519}$, and each of R$_{517}$, R$_{518}$, and R$_{519}$ is independently chosen from H, cycloalkyl, aryl, heteroaryl, and heterocycloalkyl and alkyl optionally substituted with halogen, CN, COOH, NH$_2$, NO$_2$, and C$_{1-4}$alkyl, wherein the compound is not:
3'-chloro-4'-((2R,3S,4S,5S,6R)-3,4,5-trihydroxy-6-(hydroxymethyl)tetrahydro-2H-pyran-2-yloxy)biphenyl-4-carbonitrile,
3'-methyl-N-(pyridin-3-yl)-4'-((2R,3S,4S,5S,6R)-3,4,5-trihydroxy-6-(hydroxymethyl)tetrahydro-2H-pyran-2-yloxy)biphenyl-3-carboxamide,
3'-methyl-N-(pyridin-4-yl)-4'-((2R,3S,4S,5S,6R)-3,4,5-trihydroxy-6-(hydroxymethyl)tetrahydro-2H-pyran-2-yloxy)biphenyl-3-carboxamide,
methyl 3'-methoxy-4'-((2R,3S,4S,5S,6R)-3,4,5-trihydroxy-6-(hydroxymethyl)tetrahydro-2H-pyran-2-yloxy)biphenyl-4-carboxylate,
methyl 3'-methyl-4'-((2R,3S,4S,5S,6R)-3,4,5-trihydroxy-6-(hydroxymethyl)tetrahydro-2H-pyran-2-yloxy)biphenyl-4-carboxylate,
methyl 3'-fluoro-4'-((2R,3S,4S,5S,6R)-3,4,5-trihydroxy-6-(hydroxymethyl)tetrahydro-2H-pyran-2-yloxy)biphenyl-4-carboxylate,
3'-fluoro-N$^3$,N$^5$-dimethyl-4'-((2R,3S,4S,5S,6R)-3,4,5-trihydroxy-6-(hydroxymethyl)tetrahydro-2H-pyran-2-yloxy)biphenyl-3,5-dicarboxamide,
3'-methoxy-N$^3$,N$^5$-dimethyl-4'-((2R,3S,4S,5S,6R)-3,4,5-trihydroxy-6-(hydroxymethyl)tetrahydro-2H-pyran-2-yloxy)biphenyl-3,5-dicarboxamide,
3'-chloro-N$^3$,N$^5$-dimethyl-4'-((2R,3S,4S,5S,6R)-3,4,5-trihydroxy-6-(hydroxymethyl)tetrahydro-2H-pyran-2-yloxy)biphenyl-3,5-dicarboxamide,
N,3'-dimethyl-4'-((2R,3S,4S,5S,6R)-3,4,5-trihydroxy-6-(hydroxymethyl)tetrahydro-2H-pyran-2-yloxy)biphenyl-3-carboxamide,
3'-chloro-N-methyl-4'-((2R,3S,4S,5S,6R)-3,4,5-trihydroxy-6-(hydroxymethyl)tetrahydro-2H-pyran-2-yloxy)biphenyl-3-carboxamide,
methyl 3'-methoxy-4'-((2R,3S,4S,5S,6R)-3,4,5-trihydroxy-6-(hydroxymethyl)tetrahydro-2H-pyran-2-yloxy)biphenyl-3-carboxylate,
methyl 3'-fluoro-4'-((2R,3S,4S,5S,6R)-3,4,5-trihydroxy-6-(hydroxymethyl)tetrahydro-2H-pyran-2-yloxy)biphenyl-3-carboxylate,
methyl 3'-methyl-4'-((2R,3S,4S,5S,6R)-3,4,5-trihydroxy-6-(hydroxymethyl)tetrahydro-2H-pyran-2-yloxy)biphenyl-3-carboxylate,
N$^3$,N$^5$,3'-trimethyl-4'-((2R,3S,4S,5S,6R)-3,4,5-trihydroxy-6-(hydroxymethyl)tetrahydro-2H-pyran-2-yloxy)biphenyl-3,5-dicarboxamide,
(3'-chloro-4'-((2R,3S,4S,5S,6R)-3,4,5-trihydroxy-6-(hydroxymethyl)tetrahydro-2H-pyran-2-yloxy)biphenyl-4-yl)(morpholino)methanone,
(2R,3S,4S,5S,6R)-2-(3-chloro-4'-(1H-tetrazol-5-yl)biphenyl-4-yloxy)-6-(hydroxymethyl)tetrahydro-2H-pyran-3,4,5-triol,
methyl 3'-chloro-4'-((2R,3S,4S,5S,6R)-3,4,5-trihydroxy-6-(hydroxymethyl)tetrahydro-2H-pyran-2-yloxy)biphenyl-3-carboxylate,
methyl 3'-chloro-4'-((2R,3S,4S,5S,6R)-3,4,5-trihydroxy-6-(hydroxymethyl)tetrahydro-2H-pyran-2-yloxy)biphenyl-4-carboxylate,
methyl 3'-(trifluoromethyl)-4'-((2R,3S,4S,5S,6R)-3,4,5-trihydroxy-6-(hydroxymethyl)tetrahydro-2H-pyran-2-yloxy)biphenyl-4-carboxylate,
methyl 3'-(trifluoromethyl)-4'-((2R,3S,4S,5S,6R)-3,4,5-trihydroxy-6-(hydroxymethyl)tetrahydro-2H-pyran-2-yloxy)biphenyl-3-carboxylate,
N-methyl-3'-(trifluoromethyl)-4'-((2R,3S,4S,5S,6R)-3,4,5-trihydroxy-6-(hydroxymethyl)tetrahydro-2H-pyran-2-yloxy)biphenyl-3-carboxamide, N³,N⁵-dimethyl-3'-(trifluoromethyl)-4'-((2R,3S,4S,5S,6R)-3,4,5-trihydroxy-6-(hydroxymethyl)tetrahydro-2H-pyran-2-yloxy)biphenyl-3,5-dicarboxamide.

In certain embodiments, the compounds have structural Formula VI:

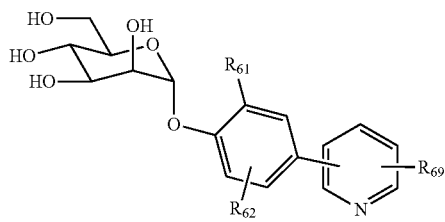

(VI)

or a salt, ester, or prodrug thereof, wherein:

$R_{61}$ is chosen from $CH_3$, $CF_3$, $OCH_3$, OAc, halogen, $NH_2$, $NHR_{64}$;

$R_{62}$ is chosen from H, $NO_2$, $NH_2$, $NHR_{64}$;

each $R_{64}$ is independently chosen from alkyl, aryl, and heteroaryl;

$R_{69}$ is chosen from COOH, COOalkyl, halogen, or alkyl, cycloalkyl, heterocycloalkyl, aryl or heteroaryl optionally substituted with halo, heteroaryl optionally substituted with halo, and $CONR_{610}R_{611}$;

$R_{610}$ is chosen from H, alkyl, aryl, and heteroaryl;

$R_{611}$ is chosen from $C_{2-8}$alkyl, aryl, and heteroaryl;

or $R_{610}$ and $R_{611}$ together form a cycloalkyl or heterocycloalkyl ring.

In certain embodiments, the compounds have structural Formula VII:

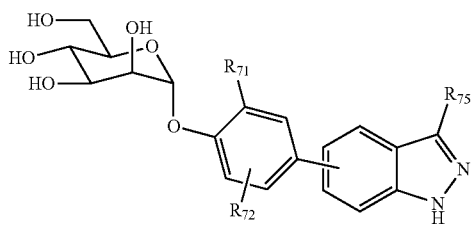

(VII)

or a salt, ester, or prodrug thereof, wherein:

$R_{71}$ is chosen from $CH_3$, $CF_3$, $OCH_3$, OAc, halogen, $NH_2$, $NHR_{74}$;

$R_{72}$ is chosen from H, $NO_2$, $NH_2$, $NHR_{74}$;

each $R_{74}$ is independently chosen from alkyl, aryl, and heteroaryl;

and $R_{75}$ is amino, alkyl, or an aryl or heteroaryl group optionally substituted with one or more of the following:

halogen, CN, COOH, $NH_2$, $NO_2$, and $C_{1-4}$alkyl.

In certain embodiments, the compounds have structural Formula VIII:

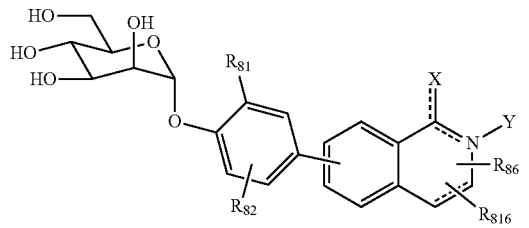

(VIII)

or a salt, ester, or prodrug thereof, wherein:

" ---- " represents a single or double bond;

$R_{81}$ is chosen from $CH_3$, $CF_3$, $OCH_3$, OAc, halogen, $NH_2$, $NHR_{84}$;

$R_{82}$ is chosen from H, $NO_2$, $NH_2$, $NHR_{84}$;

each $R_{84}$ is independently chosen from alkyl, aryl, and heteroaryl;

X is chosen from H, =O, —OH, $OR_{812}$; —$NH_2$, and —$NHR_{812}$;

Y is chosen from absent, alkyl, H, and $R_{813}$;

$R_{86}$ is chosen from H, CN, COOalkyl, halogen, aryl, heteroaryl, $SO_2$alkyl, $SO_2$cycloalkyl, $SO_2NR_{87}R_{88}$, and $CONR_{87}R_{88}$;

each $R_{87}$ and $R_{814}$ is independently chosen from H, aryl, heteroaryl, and alkyl optionally substituted with halogen, CN, COOH, $NH_2$, $CF_3$, $NO_2$, and $C_{1-4}$alkyl;

$R_{88}$ is chosen from $C_{2-8}$alkyl, aryl, heterocycloalkyl, and heteroaryl;

or $R_{87}$ and $R_{88}$ together form a heterocycloalkyl ring;

$R_{816}$ is chosen from H, $OR_{814}$, $SR_{814}$, $NHR_{814}$, $COOR_{817}$ and $CONR_{818}R_{819}$, and each of $R_{817}$, $R_{818}$, and $R_{819}$ is independently chosen from H, cycloalkyl, aryl, heteroaryl, heterocycloalkyl and alkyl optionally substituted with halogen, CN, COOH, $NH_2$, $CF_3$, $NO_2$, and $C_{1-4}$alkyl;

$R_{812}$ is an aryl or heteroaryl group optionally substituted with one or more of the following:

halogen, CN, COOH, $NO_2$, and $C_{1-4}$alkyl.

and $R_{813}$ is an aryl or heteroaryl group optionally substituted with one or more of the following:

halogen, CN, COOH, $NO_2$, and $C_{1-4}$alkyl;

wherein the compound is not 7-(3-methyl-4-((2R,3S,4S,5S,6R)-3,4,5-trihydroxy-6-(hydroxymethyl)tetrahydro-2H-pyran-2-yloxy)phenyl)isoquinolin-1(2H)-one.

In certain embodiments, the compounds have structural Formula IX:

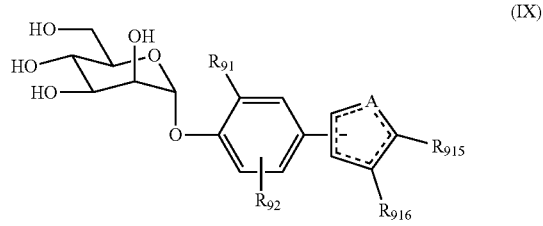

(IX)

or a salt, ester, or prodrug thereof, wherein:

" ---- " represents a single or double bond;

A is chosen from S, O, $NR_{917}$;

$R_{91}$ is chosen from $CH_3$, $CF_3$, $OCH_3$, OAc, halogen, $NH_2$, $NHR_{94}$;

$R_{92}$ is chosen from H, $NO_2$, $NH_2$, $NHR_{94}$;

each $R_{94}$ is independently chosen from alkyl, aryl, and heteroaryl;

each $R_{915}$ and $R_{916}$ is independently chosen from H, cycloalkyl, aryl, heteroaryl, heterocycloalkyl and alkyl optionally substituted with halogen, CN, COOH, $NH_2$, $CF_3$, $NO_2$, and $C_{1-4}$alkyl;

or $R_{915}$ and $R_{916}$ together form a cycloalkyl, aryl, heterocycloalkyl or heteroaryl ring, optionally substituted with one or more of the following:

oxo, halogen, CN, COOH, $NH_2$, $CF_3$, $NO_2$, and $C_{1-4}$alkyl; and $R_{917}$ is chosen from absent, H, and alkyl;

wherein the compound is not:

1-(3-chloro-4-((2R,3S,4S,5S,6R)-3,4,5-trihydroxy-6-(hydroxymethyl)tetrahydro-2H-pyran-2-yloxy)phenyl)-1H-indole-5-carboxylic acid, 1-(3-chloro-4-((2R,3S,4S,5S,6R)-3,4,5-trihydroxy-6-(hydroxymethyl)tetrahydro-2H-pyran-2-yloxy)phenyl)-1H-pyrrolo[2,3-b]pyridine-5-carbonitrile, (2R,3S,4S,5S,6R)-2-(2-chloro-4-(5-chloro-1H-pyrrolo[2,3-b]pyridin-1-yl)phenoxy)-6-(hydroxymethyl)tetrahydro-2H-pyran-3,4,5-triol, (2R,3S,4S,5S,6R)-2-(hydroxymethyl)-6-(2-methoxy-4-(5-nitro-1H-indol-1-yl)phenoxy)tetrahydro-2H-pyran-3,4,5-triol, (2R,3S,4S,5S,6R)-2-(2-fluoro-4-(5-nitro-1H-indol-1-yl)phenoxy)-6-(hydroxymethyl)tetrahydro-2H-pyran-3,4,5-triol, (2R,3S,4S,5S,6R)-2-(2-fluoro-4-(1H-indol-1-yl)phenoxy)-6-(hydroxymethyl)tetrahydro-2H-pyran-3,4,5-triol, (2R,3S,4S,5S,6R)-2-(2-chloro-4-(5-(trifluoromethyl)-1H-indol-1-yl)phenoxy)-6-(hydroxymethyl)tetrahydro-2H-pyran-3,4,5-triol, 1-(3-chloro-4-((2R,3S,4S,5S,6R)-3,4,5-trihydroxy-6-(hydroxymethyl)tetrahydro-2H-pyran-2-yloxy)phenyl)-1H-indole-6-carboxylic acid, (2R,3S,4S,5S,6R)-2-(2-chloro-4-(1H-indol-1-yl)phenoxy)-6-(hydroxymethyl)tetrahydro-2H-pyran-3,4,5-triol, (2R,3S,4S,5S,6R)-2-(2-chloro-4-(5-nitro-1H-indol-1-yephenoxy)-6-(hydroxymethyl)tetrahydro-2H-pyran-3,4,5-triol.

Further, the present invention relates to imaging compositions comprising a radiolabeled compound having Formula V as described herein and a method of detecting an infectious agent or pathogen comprising administering to a subject an imaging composition comprising the radiolabeled compound; employing a nuclear imaging technique for monitoring or visualizing a distribution of the radiolabeled compound within the body or within a portion thereof; and correlating the distribution of the radiolabeled compound to the existence of an infectious agent or pathogen having FimH.

The compounds of the present invention can also be used in various nuclear imaging techniques when labeled with a suitable radionuclide. Accordingly, an imaging composition in accordance with the present invention comprises a radiolabeled compound having Formula V, wherein the labeled compound comprises a radioisotope selected from the group consisting of $^{11}C$, $^{13}N$, $^{15}O$, $^{18}F$, $^{75}Br$, $^{124}I$, $^{125}I$, and $^{131}I$. Methods known in the art for radiolabeling the compounds of the present invention may be used.

Imaging methods in accordance with the present invention include a method of detecting an infectious agent having FimH comprising:

administering to a subject a radiolabeled compound having Formula V;

employing a nuclear imaging technique for monitoring or visualizing a distribution of the radiolabeled compound within the body or within a portion thereof; and correlating the distribution of the radiolabeled compound to the existence of an infectious agent having FimH.

In various embodiments, the nuclear imaging technique is positron emission tomography (PET) or photon emission computed tomography (SPECT).

In an embodiment, said labeled compound comprises a fluorophore selected from the group consisting of fluroscein (or variants thereof) or a cyanine dye chosen from Cy3 or Cy5.

Also provided are embodiments wherein any embodiment above may be combined with any one or more of these embodiments, provided the combination is not mutually exclusive.

As used herein, two embodiments are "mutually exclusive" when one is defined to be something which is different than the other. For example, an embodiment wherein two groups combine to form a cycloalkyl is mutually exclusive with an embodiment in which one group is ethyl the other group is hydrogen. Similarly, an embodiment wherein one group is $CH_2$ is mutually exclusive with an embodiment wherein the same group is NH.

Also provided is a compound chosen from the Examples disclosed herein.

The present invention also relates to a method of inhibiting at least one FimH function comprising the step of contacting FimH with a compound as described herein. The cell phenotype, cell proliferation, activity of FimH, change in biochemical output produced by active FimH, expression of FimH, or binding of FimH with a natural binding partner may be monitored. Such methods may be modes of treatment of disease, biological assays, cellular assays, biochemical assays, or the like.

Also provided herein is a method of treatment or prevention of a FimH-mediated disease comprising the administration of a therapeutically effective amount of a compound as disclosed herein, or a salt thereof, to a patient in need thereof.

In an embodiment, said disease is an antibiotic-resistant bacterial infection.

In certain embodiments, said disease is chosen from urinary tract infection.

In certain embodiments, said disease is chosen from Crohn's Disease.

In certain embodiments, said disease is chosen from Inflammatory Bowel Disease.

In an embodiment, said urinary tract infection is chronic.

In an embodiment, said urinary tract infection is recurrent.

Also provided herein is a compound as disclosed herein for use as a medicament.

Also provided herein is a compound as disclosed herein for use as a medicament for the treatment of a FimH-mediated disease.

Also provided is a compound as disclosed herein for use in the manufacture of a medicament for the treatment of a FimH-mediated disease.

Also provided herein is a method of inhibition of FimH function comprising contacting FimH with a compound as disclosed herein, or a salt thereof.

In certain embodiments, the FimH-mediated disease is chosen from urinary tract infection.

In certain embodiments, the FimH-mediated disease is chosen from Crohn's Disease.

In certain embodiments, the FimH-mediated disease is chosen from Inflammatory Bowel Disease Also provided is a method of inhibition of FimH-mediated function in a subject comprising the administration of a therapeutically effective amount of a compound as disclosed herein.

Also provided is a pharmaceutical composition comprising a compound as disclosed herein, together with a pharmaceutically acceptable carrier.

In certain embodiments, the pharmaceutical composition is formulated for oral (PO) administration.

In certain embodiments, the oral pharmaceutical composition is chosen from a tablet and a capsule.

Also provided is a method of treatment of a FimH-mediated disease comprising the administration of:
a. a therapeutically effective amount of a compound of Formula (I) according to claim 1; and
b. another therapeutic agent.

TERMS

Figure 1:
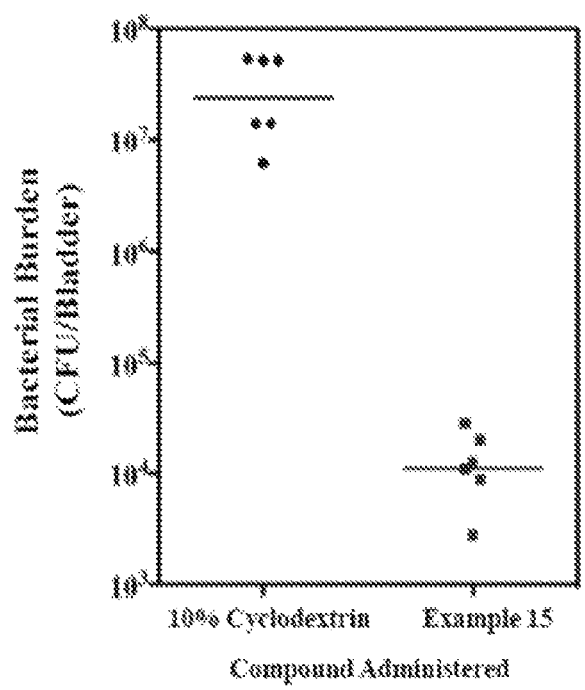
FIG. 1 provides the bacterial burden as described in the in vivo assay for example 15, compared to the control (cyclodextrin).

As used herein, the terms below have the meanings indicated.

When ranges of values are disclosed, and the notation "from $n_1$ ... to $n_2$" or "between $n_1$ ... and $n_2$" is used, where $n_1$ and $n_2$ are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 µM (micromolar)," which is intended to include 1 µM, 3 µM, and everything in between to any number of significant figures (e.g., 1.255 µM, 2.1 µM, 2.9999 µM, etc.).

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

The term "acyl," as used herein, alone or in combination, refers to a carbonyl attached to an alkenyl, alkyl, aryl, cycloalkyl, heteroaryl, heterocycle, or any other moiety were the atom attached to the carbonyl is carbon. An "acetyl" group refers to a —C(O)CH$_3$ group. An "alkylcarbonyl" or "alkanoyl" group refers to an alkyl group attached to the parent molecular moiety through a carbonyl group. Examples of such groups include methylcarbonyl and ethylcarbonyl. Examples of acyl groups include formyl, alkanoyl and aroyl.

The term "alkenyl," as used herein, alone or in combination, refers to a straight-chain or branched-chain hydrocarbon radical having one or more double bonds and containing from 2 to 20 carbon atoms. In certain embodiments, said alkenyl will comprise from 2 to 6 carbon atoms. The term "alkenylene" refers to a carbon-carbon double bond system attached at two or more positions such as ethenylene [(—CH═CH—), (—C::C—)]. Examples of suitable alkenyl radicals include ethenyl, propenyl, 2-methylpropenyl, 1,4-butadienyl and the like. Unless otherwise specified, the term "alkenyl" may include "alkenylene" groups.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to 20 carbon atoms. In certain embodiments, said alkyl will comprise from 1 to 10 carbon atoms. In further embodiments, said alkyl will comprise from 1 to 8 carbon atoms. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—CH$_2$—). Unless otherwise specified, the term "alkyl" may include "alkylene" groups.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "alkylidene," as used herein, alone or in combination, refers to an alkenyl group in which one carbon atom of the carbon-carbon double bond belongs to the moiety to which the alkenyl group is attached.

The term "alkylthio," as used herein, alone or in combination, refers to an alkyl thioether (R—S—) radical wherein the term alkyl is as defined above and wherein the sulfur may be singly or doubly oxidized. Examples of suitable alkyl thioether radicals include methylthio, ethylthio, n-propylthio, isopropylthio, n-butylthio, iso-butylthio, sec-butylthio, tert-butylthio, methanesulfonyl, ethanesulfinyl, and the like.

The term "alkynyl," as used herein, alone or in combination, refers to a straight-chain or branched chain hydrocarbon radical having one or more triple bonds and containing from 2 to 20 carbon atoms. In certain embodiments, said alkynyl comprises from 2 to 6 carbon atoms. In further embodiments, said alkynyl comprises from 2 to 4 carbon atoms. The term "alkynylene" refers to a carbon-carbon triple bond attached at two positions such as ethynylene (—C:::C—, —C≡C—). Examples of alkynyl radicals include ethynyl, propynyl, hydroxypropynyl, butyn-1-yl, butyn-2-yl, pentyn-1-yl, 3-methylbutyn-1-yl, hexyn-2-yl, and the like. Unless otherwise specified, the term "alkynyl" may include "alkynylene" groups.

The terms "amido" and "carbamoyl," as used herein, alone or in combination, refer to an amino group as described below attached to the parent molecular moiety through a carbonyl group, or vice versa. The term "C-amido" as used herein, alone or in combination, refers to a —C(O)N(RR') group with R and R' as defined herein or as defined by the specifically enumerated "R" groups designated. The term "N-amido" as used herein, alone or in combination, refers to a R'(O)N(R')— group, with R and R' as defined herein or as defined by the specifically enumerated "R" groups designated. The term "acylamino" as used herein, alone or in combination, embraces an acyl group attached to the parent moiety through an amino group. An example of an "acylamino" group is acetylamino ($CH_3C(O)NH$—).

The term "amino," as used herein, alone or in combination, refers to —NRR', wherein R and R' are independently chosen from hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which may be optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "arylalkenyl" or "aralkenyl," as used herein, alone or in combination, refers to an aryl group attached to the parent molecular moiety through an alkenyl group.

The term "arylalkoxy" or "aralkoxy," as used herein, alone or in combination, refers to an aryl group attached to the parent molecular moiety through an alkoxy group.

The term "arylalkyl" or "aralkyl," as used herein, alone or in combination, refers to an aryl group attached to the parent molecular moiety through an alkyl group.

The term "arylalkynyl" or "aralkynyl," as used herein, alone or in combination, refers to an aryl group attached to the parent molecular moiety through an alkynyl group.

The term "arylalkanoyl" or "aralkanoyl" or "aroyl," as used herein, alone or in combination, refers to an acyl radical derived from an aryl-substituted alkanecarboxylic acid such as benzoyl, napthoyl, phenylacetyl, 3-phenylpropionyl (hydrocinnamoyl), 4-phenylbutyryl, (2-naphthyl)acetyl, 4-chlorohydrocinnamoyl, and the like.

The term aryloxy as used herein, alone or in combination, refers to an aryl group attached to the parent molecular moiety through an oxy.

The terms "benzo" and "benz," as used herein, alone or in combination, refer to the divalent radical $C_6H_4$= derived from benzene. Examples include benzothiophene and benzimidazole.

The term "carbamate," as used herein, alone or in combination, refers to an ester of carbamic acid (—NHCOO—) which may be attached to the parent molecular moiety from either the nitrogen or acid end, and which may be optionally substituted as defined herein.

The term "O-carbamyl" as used herein, alone or in combination, refers to a —OC (O)NRR', group-with R and R' as defined herein.

The term "N-carbamyl" as used herein, alone or in combination, refers to a ROC (O)NR'— group, with R and R' as defined herein.

The term "carbonyl," as used herein, when alone includes formyl [—C(O)H] and in combination is a —C(O)— group.

The term "carboxyl" or "carboxy," as used herein, refers to —C(O)OH or the corresponding "carboxylate" anion, such as is in a carboxylic acid salt. An "O-carboxy" group refers to a RC(O)O— group, where R is as defined herein. A "C-carboxy" group refers to a —C(O)OR groups where R is as defined herein.

The term "cyano," as used herein, alone or in combination, refers to —CN.

The term "cycloalkyl," or, alternatively, "carbocycle," as used herein, alone or in combination, refers to a saturated or partially saturated monocyclic, bicyclic or tricyclic alkyl group wherein each cyclic moiety contains from 3 to 12 carbon atom ring members and which may optionally be a benzo fused ring system which is optionally substituted as defined herein. In certain embodiments, said cycloalkyl will comprise from 5 to 7 carbon atoms. Examples of such cycloalkyl groups include cyclopropyl, cyclobutyl, cyclopentyl, cyclohexyl, cycloheptyl, tetrahydronapthyl, indanyl, octahydronaphthyl, 2,3-dihydro-1H-indenyl, adamantyl and the like. "Bicyclic" and "tricyclic" as used herein are intended to include both fused ring systems, such as decahydronaphthalene, octahydronaphthalene as well as the multicyclic (multicentered) saturated or partially unsaturated type. The latter type of isomer is exemplified in general by, bicyclo[1,1,1]pentane, camphor, adamantane, and bicyclo[3,2,1]octane.

The term "ester," as used herein, alone or in combination, refers to a carboxy group bridging two moieties linked at carbon atoms.

The term "ether," as used herein, alone or in combination, refers to an oxy group bridging two moieties linked at carbon atoms.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro, or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloroethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—$CF_2$—), chloromethylene (—CHCl—) and the like.

The term "heteroalkyl," as used herein, alone or in combination, refers to a stable straight or branched chain, or combinations thereof, fully saturated or containing from 1 to 3 degrees of unsaturation, consisting of the stated number of carbon atoms and from one to three heteroatoms chosen from N, O, and S, and wherein the N and S atoms may optionally be oxidized and the N heteroatom may optionally be quaternized. The heteroatom (s) may be placed at any interior position of the heteroalkyl group. Up to two heteroatoms may be consecutive, such as, for example, —$CH_2$—NH—$OCH_3$.

The term "heteroaryl," as used herein, alone or in combination, refers to a 3 to 15 membered unsaturated heteromonocyclic ring, or a fused monocyclic, bicyclic, or tricyclic ring system in which at least one of the fused rings is aromatic, which contains at least one atom chosen from N, O, and S. In certain embodiments, said heteroaryl will comprise from 1 to 4 heteroatoms as ring members. In further embodiments, said heteroaryl will comprise from 1 to 2 heteroatoms as ring members. In certain embodiments, said heteroaryl will comprise from 5 to 7 atoms. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include pyrrolyl, pyrrolinyl, imidazolyl, pyrazolyl, pyridyl, pyrimidinyl, pyrazinyl, pyridazinyl, triazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Exemplary tricyclic heterocyclic groups include carbazolyl, benzidolyl, phenanthrolinyl, dibenzofuranyl, acridinyl, phenanthridinyl, xanthenyl and the like.

The terms "heterocycloalkyl" and, interchangeably, "heterocycle," as used herein, alone or in combination, each refer to a saturated, partially unsaturated, or fully unsaturated (but nonaromatic) monocyclic, bicyclic, or tricyclic heterocyclic group containing at least one heteroatom as a ring member, wherein each said heteroatom may be independently chosen from nitrogen, oxygen, and sulfur. In certain embodiments, said hetercycloalkyl will comprise from 1 to 4 heteroatoms as ring members. In further embodiments, said hetercycloalkyl will comprise from 1 to 2 heteroatoms as ring members. In certain embodiments, said hetercycloalkyl will comprise from 3 to 8 ring members in each ring. In further embodiments, said hetercycloalkyl will comprise from 3 to 7 ring members in each ring. In yet further embodiments, said hetercycloalkyl will comprise from 5 to 6 ring members in each ring. "Heterocycloalkyl" and "heterocycle" are intended to include sulfones, sulfoxides, N-oxides of tertiary nitrogen ring members, and carbocyclic fused and benzo fused ring systems; additionally, both terms also include systems where a heterocycle ring is fused to an aryl group, as defined herein, or an additional heterocycle group. Examples of heterocycle groups include aziridinyl, azetidinyl, 1,3-benzodioxolyl, dihydroisoindolyl, dihydroisoquinolinyl, dihydrocinnolinyl, dihydrobenzodioxinyl, dihydro[1,3]oxazolo[4,5-b]pyridinyl, benzothiazolyl, dihydroindolyl, dihydropyridinyl, 1,3-dioxanyl, 1,4-dioxanyl, 1,3-dioxolanyl, isoindolinyl, morpholinyl, piperazinyl, pyrrolidinyl, tetrahydropyridinyl, piperidinyl, thiomorpholinyl, and the like. The heterocycle groups may be optionally substituted unless specifically prohibited.

The term "hydrazinyl" as used herein, alone or in combination, refers to two amino groups joined by a single bond, i.e., —N—N—.

The term "hydroxy," as used herein, alone or in combination, refers to —OH.

The term "hydroxyalkyl," as used herein, alone or in combination, refers to a hydroxy group attached to the parent molecular moiety through an alkyl group.

The term "imino," as used herein, alone or in combination, refers to =N—.

The term "iminohydroxy," as used herein, alone or in combination, refers to =N (OH) and =N—O—.

The phrase "in the main chain" refers to the longest contiguous or adjacent chain of carbon atoms starting at the point of attachment of a group to the compounds of any one of the formulas disclosed herein.

The term "independently" means that where more than one substituent is selected from a number of possible substituents, those substituents may be the same or different.

The term "isocyanato" refers to a —NCO group.

The term "isothiocyanato" refers to a —NCS group.

The phrase "linear chain of atoms" refers to the longest straight chain of atoms independently selected from carbon, nitrogen, oxygen and sulfur.

The term "lower," as used herein, alone or in a combination, where not otherwise specifically defined, means containing from 1 to and including 6 carbon atoms (i.e., $C_1$-$C_6$ alkyl).

The term "lower aryl," as used herein, alone or in combination, means phenyl or naphthyl, either of which may be optionally substituted as provided.

The term "lower heteroaryl," as used herein, alone or in combination, means either 1) monocyclic heteroaryl comprising five or six ring members, of which between one and four said members may be heteroatoms chosen from N, O, and S, or 2) bicyclic heteroaryl, wherein each of the fused rings comprises five or six ring members, comprising between them one to four heteroatoms chosen from N, O, and S.

The term "lower cycloalkyl," as used herein, alone or in combination, means a monocyclic cycloalkyl having between three and six ring members (i.e., $C_3$-$C_6$ cycloalkyl). Lower cycloalkyls may be unsaturated. Examples of lower cycloalkyl include cyclopropyl, cyclobutyl, cyclopentyl, and cyclohexyl.

The term "lower heterocycloalkyl," as used herein, alone or in combination, means a monocyclic heterocycloalkyl having between three and six ring members, of which between one and four may be heteroatoms chosen from N, O, and S (i.e., $C_3$-$C_6$ heterocycloalkyl). Examples of lower heterocycloalkyls include pyrrolidinyl, imidazolidinyl, pyrazolidinyl, piperidinyl, piperazinyl, and morpholinyl. Lower heterocycloalkyls may be unsaturated.

The term "lower amino," as used herein, alone or in combination, refers to —NRR', wherein R and R' are independently chosen from hydrogen and lower alkyl, either of which may be optionally substituted.

The term "mercaptyl" as used herein, alone or in combination, refers to an RS— group, where R is as defined herein.

The term "nitro," as used herein, alone or in combination, refers to —NO$_2$.

The terms "oxy" or "oxa," as used herein, alone or in combination, refer to —O—.

The term "oxo," as used herein, alone or in combination, refers to =O.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The terms "sulfonate," "sulfonic acid," and "sulfonic," as used herein, alone or in combination, refer the —SO$_3$H group and its anion as the sulfonic acid is used in salt formation.

The term "sulfanyl," as used herein, alone or in combination, refers to —S—.

The term "sulfinyl," as used herein, alone or in combination, refers to —S(O)—.

The term "sulfonyl," as used herein, alone or in combination, refers to —S(O)$_2$—.

The term "N-sulfonamido" refers to a RS(=O)$_2$NR'— group with R and R' as defined herein.

The term "S-sulfonamido" refers to a —S(=O)$_2$NRR', group, with R and R' as defined herein.

The terms "thia" and "thio," as used herein, alone or in combination, refer to a —S— group or an ether wherein the oxygen is replaced with sulfur. The oxidized derivatives of the thio group, namely sulfinyl and sulfonyl, are included in the definition of thia and thio.

The term "thiol," as used herein, alone or in combination, refers to an —SH group.

The term "thiocarbonyl," as used herein, when alone includes thioformyl —C(S)H and in combination is a —C(S)— group.

The term "N-thiocarbamyl" refers to an ROC(S)NR'— group, with R and R' as defined herein.

The term "O-thiocarbamyl" refers to a —OC(S)NRR', group with R and R' as defined herein.

The term "thiocyanato" refers to a —CNS group.

The term "trihalomethanesulfonamido" refers to a X$_3$CS(O)$_2$NR— group with X is a halogen and R as defined herein.

The term "trihalomethanesulfonyl" refers to a X$_3$CS(O)$_2$— group where X is a halogen.

The term "trihalomethoxy" refers to a X$_3$CO— group where X is a halogen.

The term "trisubstituted silyl," as used herein, alone or in combination, refers to a silicone group substituted at its three free valences with groups as listed herein under the definition of substituted amino Examples include trimethysilyl, tert-butyldimethylsilyl, triphenylsilyl and the like.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

When a group is defined to be "null," what is meant is that said group is absent.

The term "optionally substituted" means the anteceding group may be substituted or unsubstituted. When substituted, the substituents of an "optionally substituted" group may include, without limitation, one or more substituents independently selected from the following groups or a particular designated set of groups, alone or in combination: lower alkyl, lower alkenyl, lower alkynyl, lower alkanoyl, lower heteroalkyl, lower heterocycloalkyl, lower haloalkyl, lower haloalkenyl, lower haloalkynyl, lower perhaloalkyl, lower perhaloalkoxy, lower cycloalkyl, phenyl, aryl, aryloxy, lower alkoxy, lower haloalkoxy, oxo, lower acyloxy, carbonyl, carboxyl, lower alkylcarbonyl, lower carboxyester, lower carboxamido, cyano, hydrogen, halogen, hydroxy, amino, lower alkylamino, arylamino, amido, nitro, thiol, lower alkylthio, lower haloalkylthio, lower perhaloalkylthio, arylthio, sulfonate, sulfonic acid, trisubstituted silyl, N$_3$, SH, SCH$_3$, C(O)CH$_3$, CO$_2$CH$_3$, CO$_2$H, pyridinyl, thiophene, furanyl, lower carbamate, and lower urea. Where structurally feasible, two substituents may be joined together to form a fused five-, six-, or seven-membered carbocyclic or heterocyclic ring consisting of zero to three heteroatoms, for example forming methylenedioxy or ethylenedioxy. An optionally substituted group may be unsubstituted (e.g., —CH$_2$CH$_3$), fully substituted (e.g., —CF$_2$CF$_3$), monosubstituted (e.g., —CH$_2$CH$_2$F) or substituted at a level anywhere in-between fully substituted and monosubstituted (e.g., —CH$_2$CF$_3$). Where substituents are recited without qualification as to substitution, both substituted and unsubstituted forms are encompassed. Where a substituent is qualified as "substituted," the substituted form is specifically intended. Additionally, different sets of optional substituents to a particular moiety may be defined as needed; in these cases, the optional substitution will be as defined, often immediately following the phrase, "optionally substituted with."

The term R or the term R', appearing by itself and without a number designation, unless otherwise defined, refers to a moiety chosen from hydrogen, alkyl, cycloalkyl, heteroalkyl, aryl, heteroaryl and heterocycloalkyl, any of which may be optionally substituted. Such R and R' groups should be understood to be optionally substituted as defined herein. Whether an R group has a number designation or not, every R group, including R, R' and R" where n=(1, 2, 3, . . . n), every substituent, and every term should be understood to be independent of every other in terms of selection from a group. Should any variable, substituent, or term (e.g. aryl, heterocycle, R, etc.) occur more than one time in a formula or generic structure, its definition at each occurrence is independent of the definition at every other occurrence. Those of skill in the art will further recognize that certain groups may be attached to a parent molecule or may occupy a position in a chain of elements from either end as written. For example, an unsymmetrical group such as —C(O)N(R)— may be attached to the parent moiety at either the carbon or the nitrogen.

Asymmetric centers exist in the compounds disclosed herein. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds disclosed herein can exist in unsolvated as well as solvated forms with pharmaceutically acceptable solvents such as water, ethanol, and the like. In general, the solvated forms are considered equivalent to the unsolvated forms.

The compounds according to Formulas (I) to (IX), respectively, or a pharmaceutically acceptable salt thereof of the present invention may contain one or more asymmetric center (also referred to as a chiral center) and may, therefore, exist as individual enantiomers, diastereomers, or other stereoisomeric forms, or as mixtures thereof. Chiral centers, such as chiral carbon atoms, may also be present in a substituent such as an alkyl group. Where the stereochemistry of a chiral center present in Formulas (I) to (IX), respectively, or a pharmaceutically acceptable salt thereof, or in any chemical structure illustrated herein, is not specified the structure is intended to encompass all individual stereoisomers and all mixtures thereof. Thus, compounds according to Formulas (I) to (IX), respectively, or a pharmaceutically acceptable salt thereof, containing one or more chiral center may be used as racemic mixtures, enantiomerically enriched mixtures, or as enantiomerically pure individual stereoisomers.

Individual stereoisomers of a compound according to Formulas (I) to (IX), respectively, or a pharmaceutically acceptable salt thereof, which contain one or more asymmetric center may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. The skilled artisan will appreciate that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation. When a disclosed compound or its salt is named or depicted by structure, it is to be understood that the compound or salt, including solvates (particularly, hydrates) thereof, may exist in crystalline forms, non-crystalline forms or a mixture thereof. The compound or salt, or solvates (particularly, hydrates) thereof, may also exhibit polymorphism (i.e. the capacity to occur in different crystalline forms). These different crystalline forms are typically known as "polymorphs." It is to be understood that when named or depicted by structure, the disclosed compound, or solvates (particularly, hydrates) thereof, also include all polymorphs thereof. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. One of ordinary skill in the art will appreciate that different polymorphs may be produced, for example, by changing or adjusting the conditions used in crystallizing/recrystallizing the compound.

Because of their potential use in medicine, the salts of the compounds of Formulas (I) to (XIII), respectively, are preferably pharmaceutically acceptable salts. Suitable pharmaceutically acceptable salts include those described by Berge, Bighley and Monkhouse J. Pharm. Sci (1977) 66, pp 1-19.

When a compound of the invention is a base (contain a basic moiety), a desired salt form may be prepared by any suitable method known in the art, including treatment of the free base with an inorganic acid, such as hydrochloric acid, hydrobromic acid, sulfuric acid, nitric acid, phosphoric acid, and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, pyranosidyl acid, such as glucuronic acid or galacturonic acid, alpha-hydroxy acid, such as citric acid or tartaric acid, amino acid, such as aspartic acid or glutamic acid, aromatic acid, such as benzoic acid or cinnamic acid, sulfonic acid, such as p-toluenesulfonic acid, methanesulfonic acid, ethanesulfonic acid or the like. Examples of pharmaceutically acceptable salts include sulfates, pyrosulfates, bisulfates, sulfites, bisulfites, phosphates, chlorides, bromides, iodides, acetates, propionates, decanoates, caprylates, acrylates, formates, isobutyrates, caproates, heptanoates, propiolates, oxalates, malonates succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, phenylacetates, phenylpropionates, phenylbutrates, citrates, lactates, g-hydroxybutyrates, glycollates, tartrates mandelates, and sulfonates, such as xylenesulfonates, methanesulfonates, propanesulfonates, naphthalene-1-sulfonates and naphthalene-2-sulfonates.

If an inventive basic compound is isolated as a salt, the corresponding free base form of that compound may be prepared by any suitable method known to the art, including treatment of the salt with an inorganic or organic base, suitably an inorganic or organic base having a higher pKa than the free base form of the compound.

When a compound of the invention is an acid (contains an acidic moiety), a desired salt may be prepared by any suitable method known to the art, including treatment of the free acid with an inorganic or organic base, such as an amine (primary, secondary, or tertiary), an alkali metal or alkaline earth metal hydroxide, or the like. Illustrative examples of suitable salts include organic salts derived from amino acids such as glycine and arginine, ammonia, primary, secondary, and tertiary amines, and cyclic amines, such as ethylene diamine, dicyclohexylamine, ethanolamine, piperidine, morpholine, and piperazine, as well as inorganic salts derived from sodium, calcium, potassium, magnesium, manganese, iron, copper, zinc, aluminum, and lithium.

Certain of the compounds of this invention may form salts with one or more equivalents of an acid (if the compound contains a basic moiety) or a base (if the compound contains an acidic moiety). The present invention includes within its scope all possible stoichiometric and non-stoichiometric salt forms.

Because the compounds of this invention may contain both acid and base moieties, pharmaceutically acceptable salts may be prepared by treating these compounds with an alkaline reagent or an acid reagent, respectively. Accordingly, this invention also provides for the conversion of one pharmaceutically acceptable salt of a compound of this invention, e.g., a hydrochloride salt, into another pharmaceutically acceptable salt of a compound of this invention, e.g., a sodium salt or a disodium salt.

Carboxylate functional groups of compounds of the present invention have coordinated mono or di-valent cations, where such cations may include, but are not limited to alkali metals, which may include, but are not limited to lithium (Li), sodium (Na), potassium, or mixtures thereof and the like.

Quarternary amine functional groups of compounds of the present invention, which are positively charged species, also may have coordinated anions, where such anions may include, but are not limited to halogens, which may include, but are not limited to chlorides, fluorides, bromides, iodides and the like.

Compounds of Formulas (I) to (IX) of the present invention, also may form a zwitterion(s) (formerly called a dipolar ion), which is a neutral molecule with a positive and a negative electrical charge (i.e., not dipoles) at different locations within that molecule. Zwitterions are sometimes also called inner salts.

For solvates of the compounds of the invention, or salts thereof, that are in crystalline form, the skilled artisan will appreciate that pharmaceutically-acceptable solvates may be formed wherein solvent molecules are incorporated into the crystalline lattice during crystallization. Solvates may involve nonaqueous solvents such as ethanol, isopropanol, DMSO, acetic acid, ethanolamine, and ethyl acetate, or they may involve water as the solvent that is incorporated into the crystalline lattice. Solvates wherein water is the solvent that is incorporated into the crystalline lattice are typically referred to as "hydrates." Hydrates include stoichiometric hydrates as well as compositions containing variable amounts of water. The invention includes all such solvates.

The invention also includes various deuterated forms of the compounds of Formulas (I) to (IX), respectively, or a pharmaceutically acceptable salt thereof. Each available hydrogen atom attached to a carbon atom may be independently replaced with a deuterium atom. A person of ordinary skill in the art will know how to synthesize deuterated forms of the compounds of Formulas (I) to (IX), respectively, or a pharmaceutically acceptable salt thereof of the present invention. For example, deuterated materials, such as alkyl groups may be prepared by conventional techniques (see for example: methyl-d3-amine available from Aldrich Chemical Co., Milwaukee, Wis., Cat. No. 489,689-2).

The subject invention also includes isotopically-labeled compounds which are identical to those recited in Formulas (I) to (IX), respectively, or a pharmaceutically acceptable salt thereof but for the fact that one or more atoms are replaced by an atom having an atomic mass or mass number different from the atomic mass or mass number most commonly found in nature. Examples of isotopes that can be incorporated into compounds of the invention include isotopes of hydrogen, carbon, nitrogen, oxygen, fluorine, iodine and chlorine such as $^{3}H$, $^{11}C$, $^{14}C$, $^{18}F$, $^{123}I$ or $^{125}I$.

Compounds of the present invention and pharmaceutically acceptable salts of said compounds that contain the aforementioned isotopes and/or other isotopes of other atoms are within the scope of the present invention. Isotopically labeled compounds of the present invention, for example those into which radioactive isotopes such as $^{3}H$ or $^{14}C$ have been incorporated, are useful in drug and/or substrate tissue distribution assays. Tritiated, ie. $^{3}H$, and carbon-14, ie. $^{14}C$, isotopes are particularly preferred for their ease of preparation and detectability. $^{11}C$ and $^{18}F$ isotopes are particularly useful in PET (positron emission tomography).

Because the compounds of the present invention are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions.

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "disease" as used herein is intended to be generally synonymous, and is used interchangeably with, the terms "disorder," "syndrome," and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "combination therapy" means the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate capsules for each active ingredient. In addition, such administration also encompasses use of each type of therapeutic agent in a sequential manner. In either case, the treatment regimen will provide beneficial effects of the drug combination in treating the conditions or disorders described herein.

"FimH inhibitor" or "FimH antagonist", is used herein to refer to a compound that exhibits an HAI (hemagglutination inhibition) titer or $EC_{>90}$ with respect to FimH function/activity of no more than about 100 µM and more typically not more than about 50 µM, as measured in the FimH hemagglutination HAI assay described generally herein. "HAI or $EC_{>90}$" is that concentration of the FimH inhibitor/antagonist which reduces the bacterial agglutination of guinea pig red blood cells by greater than 90%. Certain compounds disclosed herein have been discovered to exhibit inhibition of this FimH function/activity. In certain embodiments, compounds will exhibit an $EC_{>90}$ with respect to FimH of no more than about 10 µM; in further embodiments, compounds will exhibit an $EC_{>90}$ with respect to FimH of no more than about 1 µM; in yet further embodiments, compounds will exhibit an $EC_{>90}$ with respect to FimH of not more than about 1 µM; in yet further embodiments, compounds will exhibit an $EC_{>90}$ with respect to FimH of not more than about 250 nM; in yet further embodiments, compounds will exhibit an $EC_{>90}$ with respect to FimH of not more than about 100 nM in yet further embodiments, compounds will exhibit an $EC_{>90}$ with respect to FimH of not more than about 50 nM in yet further embodiments, compounds will exhibit an $EC_{>90}$ with respect to FimH of not more than about 10 nM, as measured in the FimH assay described herein.

The phrase "therapeutically effective" is intended to qualify the amount of active ingredients used in the treatment of a disease or disorder or on the effecting of a clinical endpoint.

The term "therapeutically acceptable" refers to those compounds (or salts, prodrugs, tautomers, zwitterionic forms, etc.) which are suitable for use in contact with the tissues of patients without undue toxicity, irritation, and allergic response, are commensurate with a reasonable benefit/risk ratio, and are effective for their intended use.

As used herein, "treat" in reference to a condition means: (1) to ameliorate or prevent the condition or one or more of the biological manifestations of the condition, (2) to interfere with (a) one or more points in the biological cascade that leads to or is responsible for the condition or (b) one or more of the biological manifestations of the condition, (3) to alleviate one or more of the symptoms or effects associated with the condition, or (4) to slow the progression of the condition or one or more of the biological manifestations of the condition.

As used herein, reference to "treatment" of a patient is intended to include prophylaxis. Treatment may also be preemptive in nature, i.e., it may include prevention of disease. Prevention of a disease may involve complete protection from disease, for example as in the case of prevention of infection with a pathogen, or may involve prevention of disease progression. For example, prevention of a disease may not mean complete foreclosure of any effect related to the diseases at any level, but instead may mean prevention of the symptoms of a disease to a clinically significant or detectable level. Prevention of diseases may also mean prevention of progression of a disease to a later stage of the disease.

The term "patient" is generally synonymous with the term "subject" and includes all mammals including humans. Examples of patients include humans, livestock such as cows, goats, sheep, pigs, and rabbits, and companion animals such as dogs, cats, rabbits, and horses. Preferably, the patient is a human.

The term "prodrug" refers to a compound that is made more active in vivo. Certain compounds disclosed herein may also exist as prodrugs, as described in *Hydrolysis in Drug and Prodrug Metabolism: Chemistry, Biochemistry, and Enzymology* (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they may be easier to administer than the compound, or parent drug. They may, for instance, be bioavailable by oral administration whereas the parent drug is not. The prodrug may also have improved solubility in pharmaceutical compositions over the parent drug. A wide variety of prodrug derivatives are known in the art, such as those that rely on hydrolytic cleavage or oxidative activation of the prodrug. An example, without limitation, of a prodrug would be a compound which is administered as an ester (the "prodrug"), but then is metabolically hydrolyzed to the carboxylic acid, the active entity. Additional examples include peptidyl derivatives of a compound. Examples of prodrugs suitable for compounds disclosed herein are optionally substituted acetyl, amide, and phosphate groups, wherein said groups are attached to one or more of the hydroxyl groups on the molecule.

The compounds disclosed herein can exist as therapeutically acceptable salts. The present invention includes compounds listed above in the form of salts, including acid addition salts. Suitable salts include those formed with both organic and inorganic acids. Such acid addition salts will normally be pharmaceutically acceptable. However, salts of non-pharmaceutically acceptable salts may be of utility in the preparation and purification of the compound in question. Basic addition salts may also be formed and be pharmaceutically acceptable. For a more complete discussion of the preparation and selection of salts, refer to *Pharmaceutical Salts: Properties, Selection, and Use* (Stahl, P. Heinrich. Wiley-VCHA, Zurich, Switzerland, 2002).

The term "therapeutically acceptable salt," as used herein, represents salts or zwitterionic forms of the compounds disclosed herein which are water or oil-soluble or dispersible and therapeutically acceptable as defined herein. The salts can be prepared during the final isolation and purification of the compounds or separately by reacting the appropriate compound in the form of the free base with a suitable acid. Representative acid addition salts include acetate, adipate, alginate, L-ascorbate, aspartate, benzoate, benzenesulfonate (besylate), bisulfate, butyrate, camphorate, camphorsulfonate, citrate, digluconate, formate, fumarate, gentisate, glutarate, glycerophosphate, glycolate, hemisulfate, heptanoate, hexanoate, hippurate, hydrochloride, hydrobromide, hydroiodide, 2-hydroxyethansulfonate (isethionate), lactate, maleate, malonate, DL-mandelate, mesitylenesulfonate, methanesulfonate, naphthylenesulfonate, nicotinate, 2-naphthalenesulfonate, oxalate, pamoate, pectinate, persulfate, 3-phenylproprionate, phosphonate, picrate, pivalate, propionate, pyroglutamate, succinate, sulfonate, tartrate, L-tartrate, trichloroacetate, trifluoroacetate, phosphate, glutamate, bicarbonate, para-toluenesulfonate (p-tosylate), and undecanoate. Also, basic groups in the compounds disclosed herein can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. Examples of acids which can be employed to form therapeutically acceptable addition salts include inorganic acids such as hydrochloric, hydrobromic, sulfuric, and phosphoric, and organic acids such as oxalic, maleic, succinic, and citric. Salts can also be formed by coordination of the compounds with an alkali metal or alkaline earth ion. Hence, the present invention contemplates sodium, potassium, magnesium, and calcium salts of the compounds disclosed herein, and the like.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine. The cations of therapeutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

While it may be possible for the compounds of the subject invention to be administered as the raw chemical, it is also possible to present them as a pharmaceutical formulation. Accordingly, provided herein are pharmaceutical formulations which comprise one or more of certain compounds disclosed herein, or one or more pharmaceutically acceptable salts, esters, prodrugs, amides, or solvates thereof, together with one or more pharmaceutically acceptable carriers thereof and optionally one or more other therapeutic ingredients. The carrier (s) must be "acceptable" in the sense of being compatible with the other ingredients of the formulation and not deleterious to the recipient thereof. Proper formulation is dependent upon the route of administration chosen. Any of the well-known techniques, carriers, and excipients may be used as suitable and as understood in the art. The pharmaceutical compositions disclosed herein may be manufactured in any manner known in the art, e.g., by means of conventional mixing, dissolving, granulating, dragee-making, levigating, emulsifying, encapsulating, entrapping or compression processes.

The formulations include those suitable for oral, parenteral (including subcutaneous, intradermal, intramuscular, intravenous, intraarticular, and intramedullary), intraperitoneal, transmucosal, transdermal, rectal, inhalation, intranasal, and topical (including dermal, buccal, sublingual and intraocular) administration although the most suitable route may depend upon for example the condition and disorder of the recipient. The formulations may conveniently be presented in unit dosage form and may be prepared by any of the methods well known in the art of pharmacy. Typically, these methods include the step of bringing into association a compound of the invention or a pharmaceutically acceptable salt, ester, amide, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

As used herein, the term "compound(s) of the invention" means a compound of Formulas (I) to (XIII), respectively (as defined above) in any form, i.e., any salt or non-salt form (e.g., as a free acid or base form, or as a pharmaceutically acceptable salt thereof) and any physical form thereof (e.g., including non-solid forms (e.g., liquid or semi-solid forms), and solid forms (e.g., amorphous or crystalline forms, specific polymorphic forms, solvates, including hydrates (e.g., mono-, di- and hemi-hydrates)), and mixtures of various forms.

The present invention relates to a compound of Formulas (I) to (XIII), which definition referred herein includes, but are not limited to the following related sub-generic Formulas (II) and (XIII).

The alternative definitions for the various groups and substituent groups of Formulas (I) to (XIII), respectively, or a pharmaceutically acceptable salt thereof, provided throughout the specification are intended to particularly describe each compound species disclosed herein, individually, as well as groups of one or more compound species. The scope of this invention includes any combination of these group and substituent group definitions.

The alternative definitions for the various groups and substituent groups of Formulas (I) to (XIII), respectively, or a pharmaceutically acceptable salt thereof, provided throughout the specification are intended to particularly describe each compound species disclosed herein, individually, as well as groups of one or more compound species. The scope of this invention includes any combination of these group and substituent group definitions.

Formulations of the compounds disclosed herein suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

Pharmaceutical preparations which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The formulations may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Formulations for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner Such compositions may comprise the active ingredient in a flavored basis such as sucrose and acacia or tragacanth.

The compounds may also be formulated in rectal compositions such as suppositories or retention enemas, e.g., containing conventional suppository bases such as cocoa butter, polyethylene glycol, or other glycerides.

Certain compounds disclosed herein may be administered topically, that is by non-systemic administration. This includes the application of a compound disclosed herein externally to the epidermis or the buccal cavity and the instillation of such a compound into the rectum, lung, vaginal cavity, ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient for topical administration may comprise, for example, from 0.001% to 10% w/w (by weight) of the formulation. In certain embodiments, the active ingredient may comprise as much as 10% w/w. In other embodiments, it may comprise less than 5% w/w. In certain embodiments, the active ingredient may comprise from 2% w/w to 5% w/w. In other embodiments, it may comprise from 0.1% to 1% w/w of the formulation.

For administration by inhalation, compounds may be conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, the compounds according to the invention may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Preferred unit dosage formulations are those containing an effective dose, as herein below recited, or an appropriate fraction thereof, of the active ingredient.

It should be understood that in addition to the ingredients particularly mentioned above, the formulations described above may include other agents conventional in the art having regard to the type of formulation in question, for example those suitable for oral administration may include flavoring agents.

Compounds may be administered orally or via injection at a dose of from 0.1 to 500 mg/kg per day. The dose range for adult humans is generally from 5 mg to 2 g/day. Tablets or other forms of presentation provided in discrete units may conveniently contain an amount of one or more compounds which is effective at such dosage or as a multiple of the same, for instance, units containing 5 mg to 500 mg, usually around 10 mg to 200 mg.

The amount of active ingredient that may be combined with the carrier materials to produce a single dosage form will vary depending upon the host treated and the particular mode of administration.

The compounds can be administered in various modes, e.g. orally, topically, or by injection. The precise amount of compound administered to a patient will be the responsibility of the attendant physician. The specific dose level for any particular patient will depend upon a variety of factors including the activity of the specific compound employed, the age, body weight, general health, sex, diets, time of administration, route of administration, rate of excretion, drug combination, the precise disorder being treated, and the severity of the indication or condition being treated. Also, the route of administration may vary depending on the condition and its severity.

In certain instances, it may be appropriate to administer at least one of the compounds described herein (or a pharmaceutically acceptable salt, ester, or prodrug thereof) in combination with another therapeutic agent. By way of example only, if one of the side effects experienced by a patient upon receiving one of the compounds herein is hypertension, then it may be appropriate to administer an anti-hypertensive agent in combination with the initial therapeutic agent. Or, by way of example only, the therapeutic effectiveness of one of the compounds described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit of experienced by a patient may be increased by administering one of the compounds described herein with another therapeutic agent (which also includes a therapeutic regimen) that also has therapeutic benefit. By way of example only, in a treatment for urinary tract infection involving administration of one of the compounds described herein, increased therapeutic benefit may result by also providing the patient with another therapeutic agent for urinary tract infection. In any case, regardless of the disease, disorder or condition being treated, the overall benefit experienced by the patient may simply be additive of the two therapeutic agents or the patient may experience a synergistic benefit.

In any case, the multiple therapeutic agents (at least one of which is a compound disclosed herein) may be administered in any order or even simultaneously. If simultaneously, the multiple therapeutic agents may be provided in a single, unified form, or in multiple forms (by way of example only, either as a single pill or as two separate pills). One of the therapeutic agents may be given in multiple doses, or both may be given as multiple doses. If not simultaneous, the timing between the multiple doses may be any duration of time ranging from a few minutes to four weeks.

Thus, in another aspect, certain embodiments provide methods for treating FimH-mediated disorders in a human or animal subject in need of such treatment comprising administering to said subject an amount of a compound disclosed herein effective to reduce or prevent said disorder in the subject, in combination with at least one additional agent for the treatment of said disorder that is known in the art. In a related aspect, certain embodiments provide therapeutic compositions comprising at least one compound disclosed herein in combination with one or more additional agents for the treatment of FimH-mediated disorders.

Specific diseases to be treated by the compounds, compositions, and methods disclosed herein include bacterial infections, Crohn's Disease, and irritable bowel syndrome (IBS). In certain embodiments, the bacterial infection is a urinary tract infection.

Besides being useful for human treatment, certain compounds and formulations disclosed herein may also be useful for veterinary treatment of companion animals, exotic animals and farm animals, including mammals, and the like. More preferred animals include horses, dogs, and cats.

It is noted that each compound herein can be properly named in multiple ways. For example, 3-(5-methyl-2-nitro-4-((2R,3S,4S,5S,6R)-3,4,5-trihydroxy-6-(hydroxymethyl) tetrahydro-2H-pyran-2-yloxy)phenoxy)benzonitrile and 3-[4-(α-D-mannopyranosyloxy)-5-methyl-2-nitrophenoxy] benzonitrile are two ways to describe Example 1. These names are equivalent and can be used interchangeably to correctly describe the identical structure.

LIST OF ABBREVIATIONS

Ac=acetyl; Ac$_2$O=acetic anhydride; Bn=benzyl; BnBr=benzyl bromide; OsO$_4$=osmium tetraoxide; BCl$_3$=boron trichloride; NaIO$_4$=sodium periodate; CuSO$_4$=copper sulfate; n-BuiLi=n-butyl lithium; Cy=cyclohexyl; dba=dibenzylideneacetone; DCI=4,5-dicyanoimidazole; DDTT=3-((dimethylaminomethylidene) amino)-3H-1,2,4-dithiazole-5-thione; DMA=N,N-dimethylacetamide; DMAP=4-Dimethylaminopyridine; DMOCP=2-chloro-5,5-dimethyl-2-oxo-1,3,2-dioxaphosphorinane; DMP=Dess-Martin periodinane; DMTr=dimethoxytrityl= (4-methoxyphenyl)$_2$ (phenyl)methyl; Piv=pivaloyl=(CH$_3$)$_3$C—C (=O)—; NaOH=sodium hydroxide; NaH=sodium hydride; M=molar; nM=nanomolar; μM=micromolar mL=milliliter; h=hour; min.=minute; HCl=hydrogen chloride; H$_2$O=water; MS=mass spectrometry; LCMS=Liquid chromatography/mass spectrometry; ES+=electrospray positive ionization; $^1$H-NMR=proton nuclear magnetic resonance; $^{13}$C-NMR=carbon-13 nuclear magnetic resonance; $^{31}$P-NMR=phosphorous-31 nuclear magnetic resonance; MHz=megahertz; H=hydrogen; RT=rt=room temperature; ° C.=Celsius; Br$_2$=bromine; NaHSO$_3$=sodium bisulfite; NMP=N-Methyl-2-pyrrolidone; NMM=N-methyl morpholine; NMO=N-methyl morpholine N-oxide; MW=microwave; KF=potassium fluoride; Pd (dppf)Cl$_2$=[1, 1'-bis (diphenylphosphino)ferrocene]palladium (II) dichloride; PE=petroleum ether; EtOAc=EA=EtOAc; CDCl$_3$=deuterated chloroform; DMSO-d$_6$=dimethyl sulfoxide deuterated-6; CD$_3$CN=deuterated acetonitrile; LTBA=lithium tri (tert-butoxy)aluminium hydride=LiAlH (Ot-Bu)$_3$; MeOH=methanol; NaOMe=sodium methoxide; D$_2$O=deuterated water; prep-HPLC=preparative high pressure liquid chromatography, also known as preparative high performance liquid chromatography; DMSO=dimethyl sulfoxide; MeCN=CH$_3$CN=acetonitrile; CH$_3$I=methyl iodide; NH$_3$=ammonia; NH$_4$OH=ammonium hydroxide; NIS=N-iodosuccinimide; DMF=N,N-dimethylformamide; K$_3$PO$_4$=potassium phosphate, tribasic; N$_2$=nitrogen; Py=pyridine; THF=tetrahydrofuran; Cs$_2$CO$_3$=cesium carbonate; Na$_2$CO$_3$=sodium carbonate; NaHCO$_3$=sodium bicarbonate; Na$_2$SO$_4$=sodium sulfate; TEA=triethylamine; TBSCl=tert-butyldimethylsilyl chloride; TMSCl=trimethylsilyl chloride; TMS=trimethylsilyl; TMSOTf=trimethylsilyl triflate; TFA=trifluoroacetic acid; DCM=CH$_2$Cl$_2$=dichloromethane; Hunig's base=DIPEA=iPr$_2$NEt=N,N-diisopropylethylamine; K$_2$CO$_3$=potassium carbonate; KOAc=potassium acetate; μl=microliter; g=gram; mg=milligram.

General Synthetic Methods for Preparing Compounds

Starting materials, reagents, and solvents were purchased from commercial vendors unless otherwise noted. In general, anhydrous solvents are used for carrying out all reactions. $^1$H NMR spectra were measured on a Varian 300 MHz NMR instrument or Varian 400 MHz NMR instrument equipped with an auto sampler. The chemical shifts were reported as δ ppm relative to TMS using residual solvent peak as the reference unless otherwise noted. The following abbreviations were used to express the peak multiplicities: s=singlet; d=doublet; t=triplet; q=quartet; m=multiplet; br=broad. High-performance liquid chromatography (HPLC) was carried out on GILSON GX-281 using Waters C18 5 μM, 4.6*50 mm and Waters Prep C18 5 μM, 19*150 mm reverse phase columns, eluted with a gradient system of 5:95 to 95:5 acetonitrile:water with a buffer consisting of 0.05-0.1% TFA. Mass spectroscopy (MS) was performed on HPLC/MSD using a gradient system of 5:95 to 95:5 acetonitrile:water with a buffer consisting of 0.05-0.1% TFA on a C18 or C8 reverse-phase column and electrospray ionization (ESI) for detection. All reactions were monitored by thin layer chromatography (TLC) carried out on either Merck silica gel plates (0.25 mm thick, 60F254) or Millipore Silica gel aluminum sheets (60F254) and visualized by using UV (254 nm) or dyes such as KMnO$_4$, p-Anisaldehyde and CAM (Hannesian's Stain). Silica gel chromatography was carried out on a Teledyne ISCO CombiFlash purification system using pre-packed silica gel columns (12 g-330 g sizes). All compounds used for biological assays are greater than 95% purity based on NMR and HPLC by absorbance at 220 nm and 254 nm wavelengths.

The following general schemes shown below are used for synthesis of the compounds described in the Examples. Nucleophilic aromatic substitution between a hydroxyl group and halogen is utilized to provide diaryl ether products. Other methods utilize a Pd-mediated 'Suzuki' cross-coupling between an appropriately functionalized aryl or heteroaryl mannoside (bromide, boronic acid or boronate ester), and an arene or heteroarene with appropriate complementary functionality (bromide, boronic acid or boronate ester). Other Examples detailed within this application are obtained via a copper-mediated triazole forming 'Click' chemistry reaction between an appropriately functionalized aryl or heteroaryl mannoside azide and an alkyne.

General Synthetic Schemes for Examples

The following schemes can be used to practice the present invention.

Scheme Ia

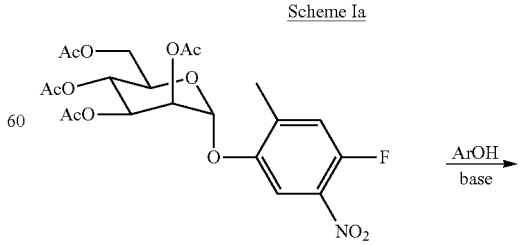

103

Scheme Ib

Example 1 can be synthesized using the general synthetic procedure set forth in Scheme Ia. Intermediate 103 is activated towards nucleophilic aromatic substitution due to the presence of the nitro group. Condensation between 103 and a phenol or other aryl alcohol in the presence of base gives the diaryl ether product.

An alternate synthesis is envisoned as shown in Scheme Ib. The alternate sense of the substitution reaction is employed, with a phenolic mannoside reacting, in the presence of base, with a suitably activated aryl fluoride, such as 2-fluoronitrobenzene, shown.

Scheme IIa

Scheme IIb

Examples 2, 3, 4, 5, and 6 can be synthesized using the general synthetic procedure set forth in Scheme IIa. The click reaction between azide-substituted mannoside 104 and an acetylene gives a triazole.

An alternative general synthetic procedure is envisioned in Scheme IIb. In this synthesis, the sense of the click reaction is reversed. An acetylene-substituted arylmannoside is allowed to react with an aryl azide to give the indicated triazole product.

Scheme III

Examples 7, 8, 9, and 10 can be synthesized using the following general synthetic procedure set forth in Scheme III. The previously reported carboxylic acid 105 is activated towards nucleophilic acyl substitution using any of a number of well-known techniques, and is then reacted with an amine to give the amide product as shown.

Scheme IVa

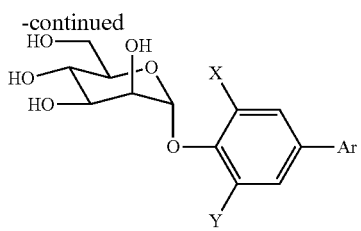

Examples 11, 12, 13, 14, 15, 16, 17, and 27 can be synthesized using the general synthetic procedure set forth in Scheme IVa. Suzuki chemistry is employed to couple mannoside boronic ester 102 with an aryl bromide. Following the Suzuki coupling, the acetates are removed under basic conditions.

Example 18 can be synthesized using the general synthetic procedure set forth in Scheme IVb. In this synthesis, the sense of the Suzuki coupling is reversed, with the modified mannose 101 being coupled with an arylboronic ester.

A representative procedure for the Suzuki coupling is elaborated below. $Cs_2CO_3$ (0.52 mmol) is activated by adding it to a round bottom flask, which is then heated to 250° C. under vacuum for 2 min, and then allowed to cool to rt under vacuum for an additional 10 min, after which time an $N_2$ atmosphere is continuously maintained. Next, the desired mannosyl bromide (or boronate) derivative (0.18 mmol) is dissolved into dioxane (5 mL) and added dropwise, followed by the addition of the desired boronate (or bromide if mannosyl boronate was used) derivative (0.35 mmol) and $H_2O$ (1 mL). After allowing the reaction to stir for 5 min at rt, $Pd(PPh_3)_4$ (0.026 mmol) is added, and the reaction flask is evacuated under high vacuum and repressurized with $N_2$ three times. The flask is then placed in an oil bath that has been preheated to 80° C., and allowed to stir for the time specified (typically 1.5 to 4 h). The reaction is then cooled to rt, and solvents are evaporated under reduced pressure. The crude reaction residue is then redissolved into $CH_2Cl_2$ (typically a colorless solid byproduct remains insoluble), and partially purified by column chromatography.

Scheme IVb

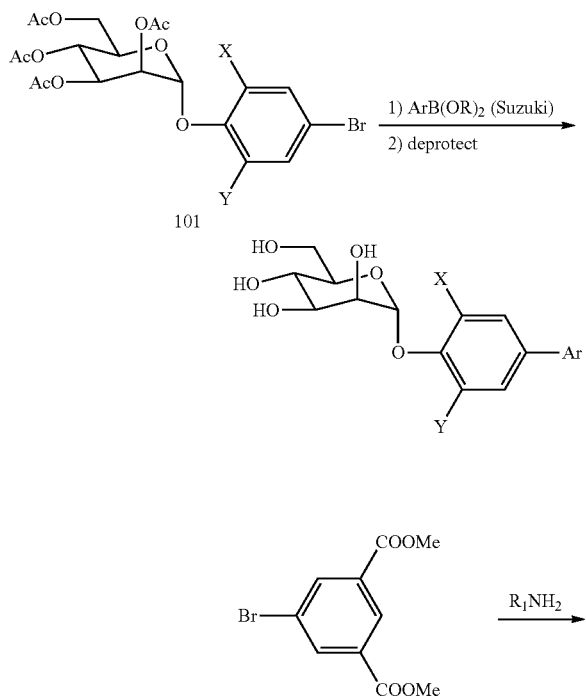

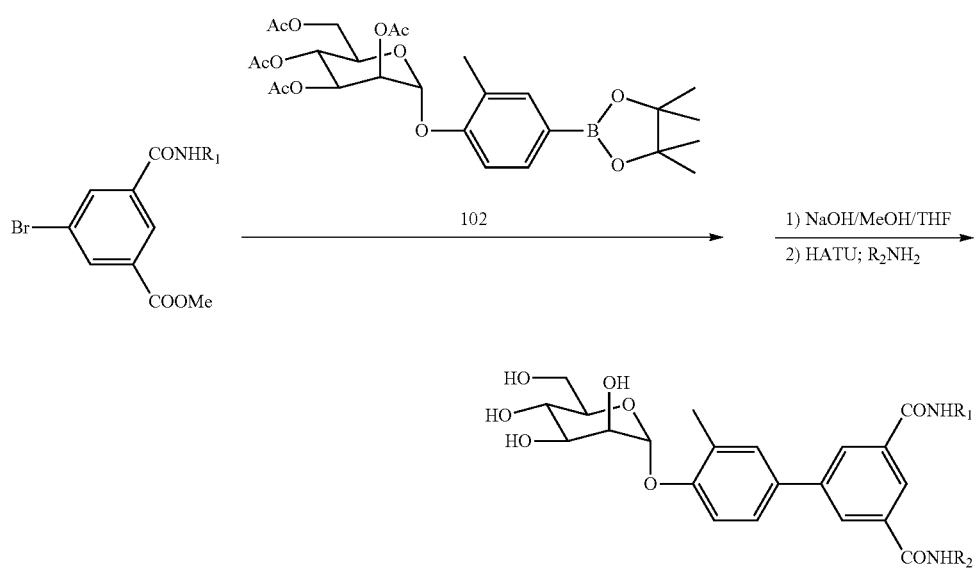

Examples 22 and 26 can be synthesized using the general synthetic procedure set forth in Scheme V. Commercially available diester 106 is converted to a monoamide by reaction with $R_1NH_2$, which is used directly in a Suzuki coupling with the arylboronic ester 102. The unreacted ester moiety and the acetate protecting groups are cleaved under basic conditions. The free acid is then coupled with $R_2NH_2$ under standard amide formation conditions to give the differentially substituted amide product.

Acetate deprotection protocol: Unless specified otherwise, acetate protecting groups are removed by dissolving the partially purified mannoside from the Suzuki reaction into MeOH (3-5 mL), and cooling to 0° C. [1M] Sodium methoxide in MeOH is added dropwise until a pH of 9-10 is achieved. After 5 min, the ice bath is removed, and the reaction is stirred for the time specified. Upon completion, the reaction is neutralized with $H^+$ exchange resin (DOWEX 50WX4-100). The resin is removed by filtration, and the filtrate is concentrated in vacuo. The resulting residue is purified by HPLC (C18, 15*150 mm column; eluent: acetonitrile/water (0.05% TFA).

O-Mannoside Building Block Synthesis

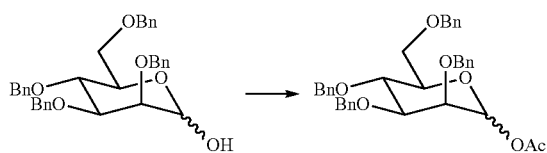 [SMILES: OC1OC(COCc2ccccc2)C(OCc2ccccc2)C(OCc2ccccc2)C1OCc1ccccc1 ; CC(=O)OC1OC(COCc2ccccc2)C(OCc2ccccc2)C(OCc2ccccc2)C1OCc1ccccc1]

Acetyl 2,3,4,6-tetra-O-benzyl-α-D-mannopyranoside Commercially available 2,3,4,6-tetra-O-benzyl-α-D-mannopyranoside (8.9 g, 16.46 mmol) and DMAP (101 mg, 0.823 mmol) were dissolved into dry pyridine (50 mL). The reaction was cooled to 0° C., and $Ac_2O$ (2.33 mL, 24.69 mmol) was added dropwise. After 15 min, the reaction was brought to rt, and stirred for 16 h. Upon completion, the reaction was cooled to 0° C., and quenched with MeOH (1 mL). The pyridine was removed in vacuo, and the residue was then redissolved in $CH_2Cl_2$, (50 mL) and washed successively with water (20 mL), 1 N aq. HCl (2×20 mL), water (20 mL), saturated aq. $NaHCO_3$ (20 mL×2), brine (20 mL), dried over $Na_2SO_4$, and concentrated in vacuo. Purification by column chromatography on silica gel (EtOAc—hexanes gradient) gave the desired compound in 95% yield.

Analytical data matches reported (R. Meuwly, A. Vasella. *Helv. Chim. Acta.* 1986, 69, 25-34.)

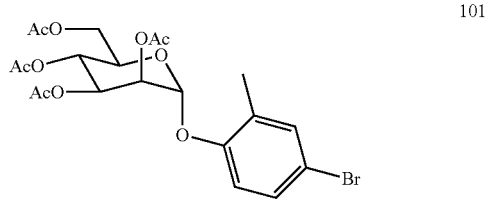 [SMILES: CC(=O)OCC1OC(Oc2ccc(Br)cc2C)C(OC(C)=O)C(OC(C)=O)C1OC(C)=O]

101

4-Bromo-2-methylphenyl 2,3,4,6-tetra-O-acetyl-a-D-mannopyranoside (101)

Under N2 atmosphere at rt, $BF_3$—$OEt_2$ (3.41 g, 24 mmol) was added dropwise into a solution of a-D-mannose pentaacetate (3.12 g, 8 mmol) and 4-bromo-2-methylphenol (2.99 g, 16 mmol) in dry $CH_2Cl_2$ (100 mL). After a few minutes the mixture was heated to reflux, and stirred for 45 h. The reaction was then cooled to rt, and washed with $H_2O$ (2×50 mL). The $CH_2Cl_2$ layer was collected, dried over $Na_2SO_4$, and concentrated in vacuo. The residue was purified by column chromatography on silica gel (ethyl acetate—dichloromethane gradient elution) to afford compound 101 in 77% yield.

$^1$H NMR (300 MHz, $CDCl_3$) δ ppm 7.18-7.38 (m, 2H), 6.97 (d, J=8.79 Hz, 1H), 5.50-5.59 (m, 1H), 5.43-5.50 (m, 2H), 5.32-5.42 (m, 1H), 4.28 (dd, J=5.63, 12.50 Hz, 1H), 3.99-4.15 (m, 2H), 2.27 (s, 3H), 2.20 (s, 3H), 2.02-2.11 (three singlets, 9H). MS (ESI): found: [M+Na]$^+$, 539.0.

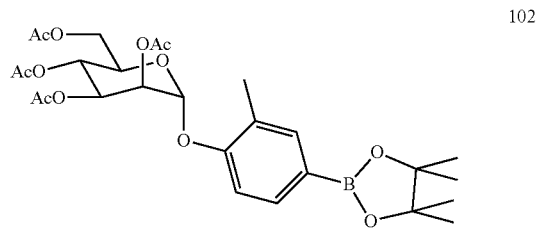 [SMILES: CC(=O)OCC1OC(Oc2ccc(B3OC(C)(C)C(C)(C)O3)cc2C)C(OC(C)=O)C(OC(C)=O)C1OC(C)=O]

102

2-Methyl-4-[4',4',5',5'-tetramethyl-1',3',2'-dioxaborolan-2'-yl]phenyl 2,3,4,6-tetra-O-acetyl-α-D-mannopyranoside (102)

Mannosyl bromide 101 (2.869 g, 5.55 mmol) was reacted in dry DMSO (50 mL) with bis(pinacolato)diboron (1.690 g, 6.66 mmol) in the presence of KOAc (2.177 g, 22.18 mmol) and Pd(dppf)Cl$_2$ (0.244 g, 0.33 mmol) at 80° C. for 2.5 h. Upon reaction completion, the crude reaction mixture was evaporated under reduced pressure, redissolved into EtOAc (40 mL) and $H_2O$ (100 mL) was added. The reaction mixture was then extracted with EtOAc (3×40 mL). The organic fractions were then combined, dried over $Na_2SO_4$, and concentrated in vacuo. The residue was purified by column chromatography on silica gel (ethyl acetate-dichloromethane gradient elution) to afford compound 102 in 79% yield.

Formula: $C_{27}H_{37}BO_{12}$ Exact Mass: 564.24 Molecular Weight: 564.39

$^1$H NMR (400 MHz, chloroform-d) δ ppm 7.55-7.67 (m, 2H) 7.09 (d, J=8.2 Hz, 1H) 5.54-5.60 (m, 2H) 5.48 (dd, J=3.3, 1.8 Hz, 1H) 5.39 (t, J=12.0 Hz, 1H) 4.27-4.33 (m, 1H) 4.03-4.09 (m, 2H) 2.30 (s, 3H) 2.21 (s, 3H) 2.06 (s, 3H) 2.05 (d, J=2.3 Hz, 6H) 1.34 (s, 12H); ESI-MS [M+Na]$^+$ calcd for $C_{27}H_{37}BO_{12}Na^+$ 587.23, found 587.4.

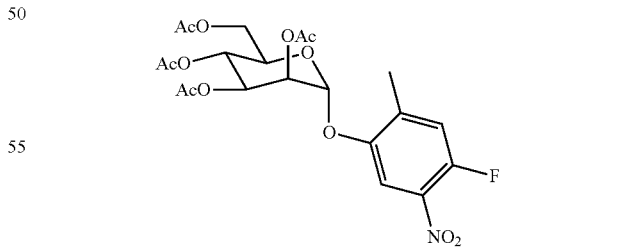

4-Fluoro-2-methyl-5-nitrophenyl 2,3,4,6-tetra-O-acetyl-α-D-mannopyranoside (103) α-D-mannose pentaacetate (0.40 g, 1.02 mmol) was dissolved in dry $CH_2Cl_2$ (10 mL) at rt under $N_2$. $Et_3N$ (0.16 mL, 1.13 mmol) was added, followed by 4-fluoro-2-methyl-4-nitrophenol (0.35 g, 2.05 mmol). $BF_3$—$OEt_2$ (0.39 mL, 3.06 mmol) was added dropwise to the reaction over 5 min, after 30 min, the temperature was raised to 40° C., and the reaction was stirred for 2 d. Upon completion, the crude reaction mixture was diluted with CH$_2$Cl$_2$ (20 mL) and washed sequentially with H$_2$O (10 mL), saturated aq. NaHCO$_3$ (10 mL) and brine (10 mL). The organic layer was then dried over Na$_2$SO$_4$, and concentrated in vacuo. The residue was purified by column chromatography on silica gel (EtOAc—hexanes gradient elution) to afford the compound in 88% yield.

Formula: C$_{21}$H$_{24}$FNO$_{12}$ Exact Mass: 501.13 Molecular Weight: 501.41

$^1$H NMR (400 MHz, chloroform-d) δ ppm 7.89 (d, J=6.3 Hz, 1H) 7.13 (d, J=11.0 Hz, 1H) 5.49-5.54 (m, 2H) 5.45-5.47 (m, 1H) 5.36 (t, J=10.0 Hz, 1H) 4.25-4.31 (m, 1H) 4.04-4.13 (m, 2H) 2.38 (s, 3H) 2.21 (s, 3H) 2.07 (s, 3H) 2.05 (d, J=2.7 Hz, 6H); ESI-MS [M+Na]$^+$ calcd for C$_{21}$H$_{24}$FNO$_{12}$Na$^+$ 524.12, found 524.3.

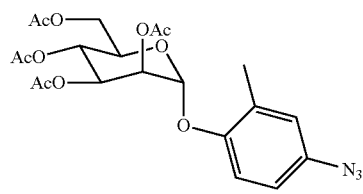 [SMILES: CC(=O)OCC1OC(Oc2ccc(N=[N+]=[N-])cc2C)C(OC(C)=O)C(OC(C)=O)C1OC(C)=O]

4-azido-2-methylphenyl 2,3,4,6-tetra-O-acetyl-α-D-mannopyranoside (104)

Following a reported literature protocol (Markiewicz, J. T.; Wiest, O. Helquist, P. *J. Org. Chem.* 2010, 75(5), 4887), 101 (1.0 g, 1.93 mmol) was dissolved in EtOH (7 mL) and H$_2$O (3 mL) under N$_2$. N,N'-dimethylethylenediamine (DMEDA) (38 μL, 0.348 mmol) was added, followed by NaN$_3$ (250 mg, 3.87 mmol), CuI (36.8 mg, 0.19 mmol), and sodium L-ascorbate (23 mg, 0.116 mmol). The reaction was refluxed for 2 h, and then cooled to rt, diluted with EtOAc (2 mL), and quenched by the addition of saturated aq. NH$_4$Cl (3 mL). The biphasic mixture was stirred 1 h at rt This biphasic mixture was stirred at room temperature for 1 h. The solution was then filtered through a pad of Celite, which was subsequently washed with EtOAc (20 mL) and water (5 mL). The filtrate was transferred to a separatory funnel, the phases were separated, and the aqueous phase was extracted with EtOAc (3×10 mL). The organic fractions were then combined and washed with saturated aq. NaHCO$_3$, (15 mL) and brine (2×15 mL), dried over Na$_2$SO$_4$, and concentrated in vacuo. As both unreacted starting material 101 and product 104 had the same retention time on TLC (in both EtOAc:Hexane and EtOAc:DCM), the residue was only able to be partially purified after a single purification by column chromatography on silica gel (EtOAc—hexanes gradient elution), wherein the fractions coming out first were mostly unreacted 101, and the fractions coming out later contained mostly product 104. As a result, 104 was obtained as a partially impure material in 56% yield.

Formula: C$_{21}$H$_{25}$N$_3$O$_{10}$ Exact Mass: 479.15 Molecular Weight: 479.44

ESI-MS [M+Na]$^+$ calcd for C$_{21}$H$_{25}$N$_3$O$_{10}$Na$^+$ 502.14, found 502.3.

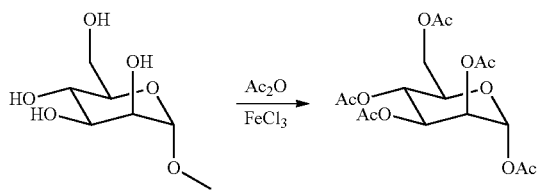

1,2,3,4,6-Penta-O-acetyl-α-D-mannopyranose A solution of methyl α-D-mannopyranoside (15 g, 77.2 mmol) and FeCl$_3$ (1.2 g, 77.2 mmol) in Ac$_2$O (90 mL) was stirred at room temperature for 3 h. The reaction was quenched by H$_2$O, extracted with EtOAc (3×50 mL), the combined organic phase was washed with water (50 mL) and brine (50 mL), dried over anhydrous Na$_2$SO$_4$ and filtered. The filtrate was concentrated under reduced pressure. The residue was purified by silica gel chromatography, eluting with ethyl acetate in petroleum ether (0-30%) to afford the title product (28.1 g, 93% yield) as a yellow oil.

ESI-MS [M+Na]$^+$ calcd for (C$_{16}$H$_{22}$O$_{11}$Na$^+$) 413.12; found: 413.05.

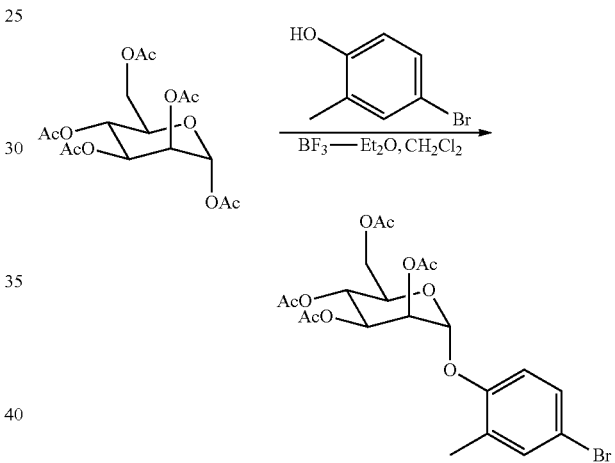

4-Bromo-2-methylphenyl-2,3,4,6-tetra-O-acetyl-α-D-mannopyranoside To the solution of the product from the previous step (10 g, 25.6 mmol), 2-methyl-4-bromine-phenol (4.0 g, 21.3 mmol) in CH$_2$Cl$_2$ (30 mL) was added dropwise BF$_3$.OEt$_2$ (15 g, 106.5 mmol) at 0° C. under N$_2$. The reaction was allowed to warm to room temperature and stirred for 3 h, and then quenched by the addition of water (20 mL) at 0° C., and extracted with CH$_2$Cl$_2$ (3×20 mL). The combined organic phase was washed with brine (20 mL), dried over anhydrous sodium sulfate and concentrated under vacuum. The crude was purified by flash silica gel column chromatography to obtain the title compound as yellow oil.

ESI-MS [M+Na]$^+$ calcd for (C$_{21}$H$_{25}$BrO$_{10}$Na$^+$) 539.06; found 539.0, 541.0.

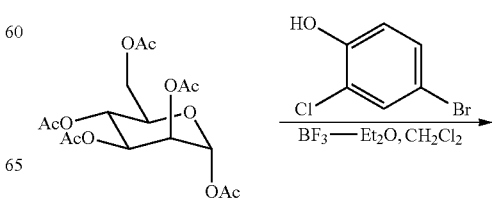

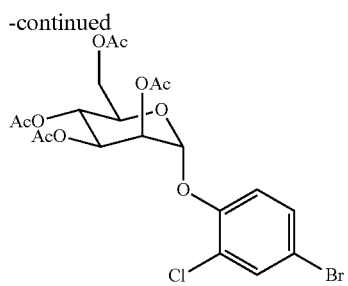

4-Bromo-2-chlorophenyl 2,3,4,6-tetra-O-acetyl-α-D-mannopyranoside (108)

The procedure of Han et al. was followed (Han, Z.; Pinkner, J. S.; Ford, B.; Chorell, E.; Crowley, J. M.; Cusumano, C. K.; Campbell, S.; Henderson, J. P.; Hultgren, S. J.; Janetka, J. W, *J. Med. Chem.* 2012, 55(8), 3945-3959.). To a solution of α-D-mannose pentaacetate (3.12 g, 8 mmol) and 4-bromo-2-chlorophenol (2.99 g, 16 mmol) in 100 mL of anhydrous $CH_2Cl_2$ under an $N_2$ atmosphere at room temperature was added dropwise $BF_3 \cdot OEt_2$ (3.41 g, 24 mmol). After a few minutes, the mixture was heated to reflux and stirred for 45 h. The reaction was then quenched with water, and extracted with $CH_2Cl_2$. The $CH_2Cl_2$ layer was collected, dried over $Na_2SO_4$, and concentrated in vacuo. The residue was purified by column chromatography on silica gel (EtOAc—hexanes gradient elution) to afford the title compound in 46% yield.

$^1$H NMR (300 MHz, $CDCl_3$) δ ppm 7.55 (d, J=2.47 Hz, 1H), 7.33 (dd, J=2.47, 8.79 Hz, 1H), 7.06 (d, J=8.79 Hz, 1H), 5.58 (dd, J=3.02, 10.16 Hz, 1H), 5.52 (s, 1H), 5.49-5.54 (m, 1H), 5.33-5.42 (m, 1H), 4.22-4.32 (m, 1H), 4.04-4.17 (m, 2H), 2.21 (s, 3H), 2.07 (s, 3H), 2.05 (s, 3H), 2.04 (s, 3H). MS (ESI): found [M+Na]$^+$, 561.0

The invention is further illustrated by the following examples.

Example 1

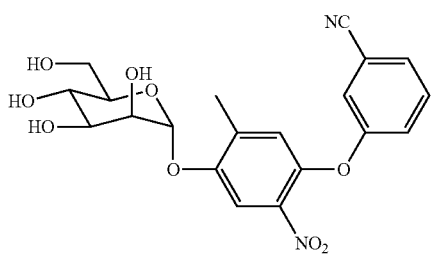

3-[4-(α-D-mannopyranosyloxy)-5-methyl-2-nitrophenoxy]benzonitrile (1)

Compound 103 (30 mg, 0.06 mmol) was dissolved into dry DMF (2 mL) under $N_2$, followed by the addition of 3-hydroxybenzonitrile (14 mg, 0.12 mmol) and $Cs_2CO_3$ (59 mg, 0.179 mmol). After 24 h at 40° C., $H_2O$ (10 mL) was added, and the reaction mixture was extracted with 1:1 EtOAc:$Et_2O$ (3×5 mL). The organic fractions were then combined and washed with saturated aq. $NaHCO_3$, (15 mL) and brine (2×15 mL), dried over $Na_2SO_4$, and concentrated in vacuo. As minor mono- and di-deprotection of the acetates also occurred (as detected by LCMS), the crude product was directly deprotected with sodium methoxide in MeOH, using the acetate deprotection protocol, and purified by HPLC (C18, 15*150 mm column; eluent: acetonitrile/water (0.05% TFA) to give the product in 46% yield.

Formula: $C_{20}H_{20}N_2O_9$ Exact Mass: 432.12 Molecular Weight: 432.39

$^1$H NMR (400 MHz, methanol-$d_4$) δ ppm 7.93 (s, 1H) 7.48-7.55 (m, 1H) 7.43-7.47 (m, 1H) 7.21-7.29 (m, 2H) 7.14 (s, 1H) 5.62 (s, 1H) 4.08-4.10 (m, 1H) 3.92 (dd, J=9.4, 3.5 Hz, 1H) 3.67-3.85 (m, 3H) 3.50-3.58 (m, 1H) 2.31 (s, 3H); ESI-MS [M+H]$^+$ calcd for $C_{20}H_{20}N_2O_9H^+$ 433.12 found 433.3.

Example 2

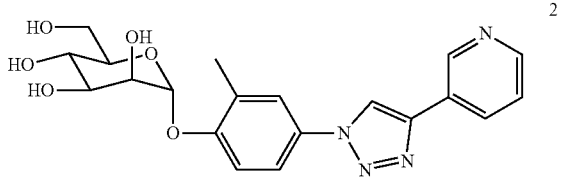 [SMILES: Cc1cc(-n2cc(-c3ccccc3)nn2)ccc1OC1OC(CO)C(O)C(O)C1O]

2-methyl-4-[4-(pyridin-3-yl)-1H-1,2,3-triazol-1-yl]phenyl α-D-mannopyranoside (2)

Intermediate 104 was converted into 2 via a two-step procedure: deprotection followed by the click-reaction. First, the acetate protecting groups were removed by dissolving azide 104 (130 mg, 0.271 mmol) into MeOH (3-5 mL), and cooling to 0° C. [1M] Sodium methoxide in MeOH was added dropwise until a pH of 9-10 was achieved. After 5 min, the ice bath was removed, and the reaction was stirred for 30 min Upon completion, the reaction was neutralized with H$^+$ exchange resin (DOWEX 50WX4-100). The resin was filtered, and the filtrate was concentrated in vacuo to afford crude 4-azido-2-methylphenyl-α-D-mannopyranoside, which was used directly in the next step.

The product from the preceding step (113 mg) was dissolved into THF (2 mL), and 3-ethynylpyridine (86 mg, 0.83 mmol) was added. Sodium ascorbate (13.2 mg, 0.069 mmol) dissolved into $H_2O$ (0.5 mL) was added dropwise, followed by the dropwise addition of $CuSO_4 \cdot 5H_2O$ (8.4 mg, 0.32 mmol) dissolved into $H_2O$ (0.5 mL) and the reaction was stirred for 2.5 h at 50° C. Upon completion, the solvents were evaporated under reduced pressure, and the residue was partially purified by column chromatography on silica gel (methanol—DCM gradient elution). Further purification was completed by HPLC (C18, 15*150 mm column; eluent: acetonitrile/water (0.05% TFA), to give the product in 52% yield.

Formula: $C_{20}H_{22}N_4O_6$ Exact Mass: 414.15 Molecular Weight: 414.41

$^1$H NMR (400 MHz, methanol-$d_4$) δ ppm 9.25 (s, 1H) 9.07 (d, J=0.8 Hz, 1H) 8.60-8.77 (m, 2H) 7.87 (dd, J=8.0, 5.7 Hz, 1H) 7.59-7.77 (m, 2H) 7.45 (d, J=8.6 Hz, 1H) 5.61 (s, 1H) 4.07-4.12 (m, 1H) 3.92-4.00 (m, 1H) 3.77 (br. s., 3H) 3.54-3.63 (m, 1H) 2.36 (s, 3H); ESI-MS [M+H]$^+$ calcd for $C_{20}H_{22}N_4O_6H^+$ 415.16 found 415.3.

Example 3

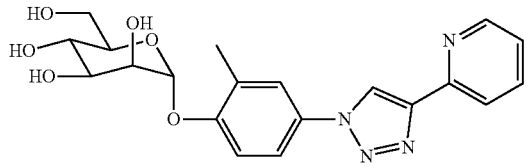

2-methyl-4-[4-(pyridin-2-yl)-1H-1,2,3-triazol-1-yl]phenyl α-D-mannopyranoside (3) was obtained in 17% yield following the same two-step deprotection/click procedure used to make 2, employing 2-ethynylpyridine.

Formula: $C_{20}H_{22}N_4O_6$ Exact Mass: 414.15 Molecular Weight: 414.41

$^1$H NMR (400 MHz, methanol-$d_4$) δ ppm 8.99 (s, 1H) 8.59-8.73 (m, 1H) 8.20-8.28 (m, 1H) 8.14 (td, J=7.8, 1.6 Hz, 1H) 7.74 (d, J=2.3 Hz, 1H) 7.68 (dd, J=8.8, 2.5 Hz, 1H) 7.51-7.60 (m, 1H) 7.45 (d, J=8.6 Hz, 1H) 5.62 (s, 1H) 4.08-4.12 (m, 1H) 3.97 (dd, J=9.4, 2.7 Hz, 1H) 3.69-3.83 (m, 3H) 3.54-3.61 (m, 1H) 2.36 (s, 3H); ESI-MS [M+H]$^+$ calcd for $C_{20}H_{22}N_4O_6H^+$ 415.16 found 415.3.

Example 4

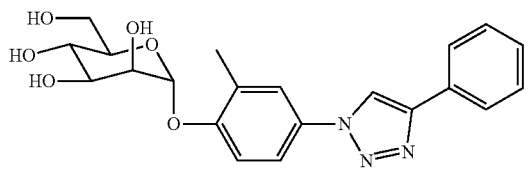

2-methyl-4-[4-(phenyl)-1H-1,2,3-triazol-1-yl]phenyl α-D-mannopyranoside (4) was obtained in 26% yield following the same two-step deprotection/click procedure used to make 2, employing phenylacetylene.

Formula: $C_{21}H_{23}N_3O_6$ Exact Mass: 413.16 Molecular Weight: 413.42

$^1$H NMR (400 MHz, methanol-$d_4$) δ ppm 8.80 (br. s., 1H) 7.91 (t, J=5.7 Hz, 2H) 7.70-7.75 (m, 1H) 7.62-7.70 (m, 1H) 7.34-7.51 (m, 4H) 5.60 (d, J=3.9 Hz, 1H) 4.10 (br. s., 1H) 3.94-4.01 (m, 1H) 3.70-3.84 (m, 3H) 3.55-3.63 (m, 1H) 2.36 (br. s., 3H); ESI-MS [M+H]$^+$ calcd for $C_{21}H_{23}N_3O_6H^+$ 414.17 found 414.3.

Example 5

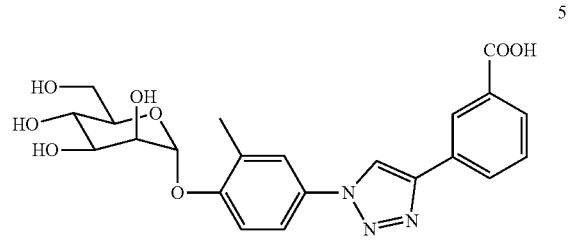 [SMILES: Cc1cc(-n2cc(-c3cccc(C(=O)O)c3)nn2)ccc1OC1OC(CO)C(O)C(O)C1O]

2-methyl-4-[4-(3-carboxyphenyl)-1H-1,2,3-triazol-1-yl] phenyl α-D-mannopyranoside (5) was obtained in 68% yield following the same two-step deprotection/click procedure used to make 2, employing 3-ethynylbenzoic acid.

Formula: $C_{22}H_{23}N_3O_8$ Exact Mass: 457.15 Molecular Weight: 457.43

$^1$H NMR (400 MHz, dimethylsulfoxide-$d_6$) δ ppm 9.35 (s, 1H) 8.53 (s, 1H) 8.19 (d, J=7.8 Hz, 1H) 7.95 (d, J=7.4 Hz, 1H) 7.82 (br. s., 1H) 7.74 (d, J=8.6 Hz, 1H) 7.64 (t, J=7.6 Hz, 1H) 7.39 (d, J=9.0 Hz, 1H) 5.51 (s, 1H) 3.93 (br. s., 1H) 3.76 (dd, J=9.0, 2.7 Hz, 1H) 3.63 (d, J=11.3 Hz, 1H) 3.45-3.58 (m, 2H) 3.37-3.44 (m, 1H) 2.30 (s, 3H); ESI-MS [M+H]$^+$ calcd for $C_{22}H_{23}N_3O_8H^+$ 458.16 found 458.3.

Example 6

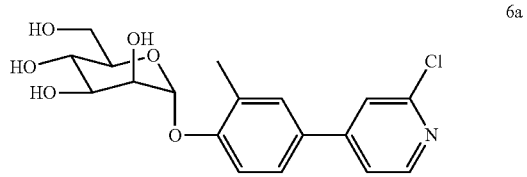

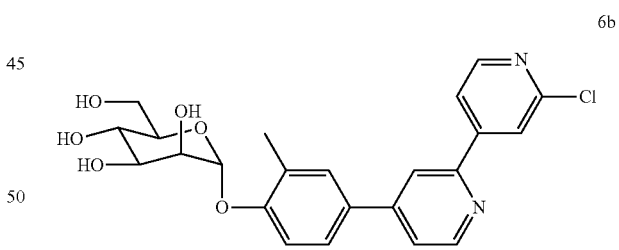

4-(2'-chloropyrid-4'-yl)-2-methylphenyl α-D-mannopyranoside (6a) and 4-[2'-(2''-chloropyrid-4''-yl)-pyrid-4'-yl]-2-methylphenyl α-D-mannopyranoside (6b)

Using an alternate Suzuki coupling protocol (Brown, R. E. et al., U.S. patent application Ser. No. 10/545,877), mannosyl bromide (101) (150 mg, 0.29 mmol) and commercially available 2-chloro-4-(4,4,5,5-tetramethyl-[1,3,2] dioxaborolan-2-yl)-pyridine (104 mg, 0.43 mmol) were dissolved into dry dioxane (2.0 mL) under Na. H$_2$O (1 mL) was added, followed by saturated aq. Na$_2$CO$_3$ (0.9 mL). Pd(dppf) Cl$_2$ (10.6 mg, 0.014 mmol) was added, and the reaction flask was evacuated under high vacuum and repressurized with Na three times. The flask was then placed in an oil bath preheated to 100° C., and allowed to stir for 16 h. The reaction was then cooled to rt, and the reaction was neutralized with 1N aq. HCl, and the solvents were evaporated under reduced pressure. The crude reaction residue was then redissolved into MeOH (5 mL) and filtered through a PTFE 40-micron filter into a reaction flask. The flask was cooled to 0° C., and 1M sodium methoxide in MeOH was added until a pH of 9-10 was achieved. After 5 min, the reaction was brought to rt and stirred an additional 30 min. At this time, two products were identified by LCMS, expected product 6a, and mannoside product containing the self-coupled heterocycle 6b. The resulting residue was separated and purified by HPLC (C18, 15*150 mm column; eluent: acetonitrile/water (0.05% TFA) to give 6a in 38% yield and 6b in 8% yield.

6a:

Formula: $C_{18}H_{20}ClNO_6$ Exact Mass: 381.10 Molecular Weight: 381.81

$^1$H NMR (400 MHz, methanol-$d_4$) δ ppm 8.34 (d, J=4.7 Hz, 1H) 7.71 (s, 1H) 7.51-7.66 (m, 3H) 7.36 (d, J=8.2 Hz, 1H) 5.60 (s, 1H) 4.04-4.10 (m, 1H) 3.92-4.00 (m, 1H) 3.66-3.83 (m, 3H) 3.50-3.59 (m, 1H) 2.32 (s, 3H).

ESI-MS [M+H]$^+$ calcd for $C_{18}H_{20}ClNO_6H^+$ 382.11 found 382.3.

6b:

Formula: $C_{23}H_{23}ClN_2O_6$ Exact Mass: 458.12 Molecular Weight: 458.89

$^1$H NMR (400 MHz, methanol-$d_4$) δ ppm 8.69 (d, J=5.1 Hz, 1H) 8.49 (d, J=5.1 Hz, 1H) 8.22 (s, 1H) 8.17 (d, J=0.8 Hz, 1H) 8.06 (dd, J=5.3, 1.4 Hz, 1H) 7.64-7.76 (m, 3H) 7.38 (d, J=8.6 Hz, 1H) 5.61 (s, 1H) 4.08 (br. s, 1H) 3.97 (dd, J=9.4, 3.1 Hz, 1H) 3.70-3.81 (m, 3H) 3.54-3.61 (m, 1H) 2.34 (s, 3H).

ESI-MS [M+H]$^+$ calcd for $C_{23}H_{23}ClN_2O_6H^+$ 459.13 found 459.3.

Example 7

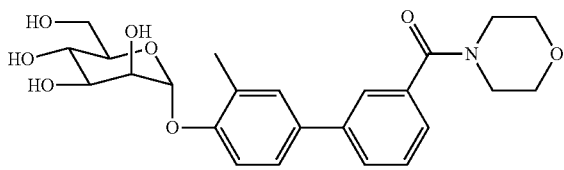

3-methyl-3'-(morpholin-4-ylcarbonyl)biphenyl-4-yl α-D-mannopyranoside (7) Previously reported compound 4'-(α-D-mannopyranosyloxy)-3'-methyl-1,1'biphenyl-3-carboxylic acid (30 mg, 0.077 mmol) and 1-[bis(dimethylamino)methylene]-1H-1,2,3-triazolo[4,5-b]pyridinium 3-oxide hexafluorophosphate (HATU) (58 mg, 0.15 mmol) were dissolved into dry DMF (3 mL) under $N_2$, and the reaction was stirred for 10 min at 0° C. Morpholine (20 μL, 0.23 mmol) and diisipropylethylamine (DIPEA) (40 μL, 0.23 mmol) were added, and the reaction was allowed to gradually warm to rt, and was stirred 24 h at rt. The solvent was evaporated under reduced pressure, and the residue was purified by HPLC (C18, 15*150 mm column; eluent: acetonitrile/water (0.05% TFA), to give the product in 51% yield.

Formula: $C_{24}H_{29}NO_8$ Exact Mass: 459.19 Molecular Weight: 459.49.

ESI-MS [M+H]$^+$ calcd for $C_{24}H_{29}NO_8H^+$ 460.20 found 460.4.

Example 8

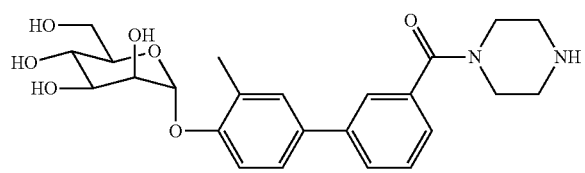

3-methyl-3'-(piperazin-1-ylcarbonyl)biphenyl-4-yl α-D-mannopyranoside (8) was synthesized following the same protocol used in the synthesis of 7, starting from the same precursor 4'-(α-D-mannopyranosyloxy)-3'-methyl-[1,1'biphenyl]-3-carboxylic acid (50 mg, 0.128 mmol), and coupling instead with piperazine (68.36 mg, 0.79 mmol). As the reaction was sluggish, a large excess of piparazine was used, and the reaction time was extended to 48 h at rt, after which the solvent was evaporated under reduced pressure, and the residue was purified by HPLC (C18, 15*150 mm column; eluent: acetonitrile/water (0.05% TFA), to give the product in 25% yield.

Formula: $C_{24}H_{30}N_2O_7$ Exact Mass: 458.21 Molecular Weight: 458.50

ESI-MS [M+H]$^+$ calcd for $C_{24}H_{30}N_2O_7H^+$ 459.21 found 459.4.

Example 9

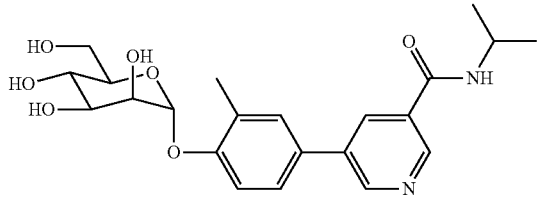

5-[4'-(α-D-mannopyranosyloxy)-3'-methylphenyl]-N-isopropyl-3-pyridinecarboxamide (9) Synthesized from 24 and 2-aminopropane, using the same coupling procedure as for 7.

Formula: $C_{22}H_{28}N_2O_7$ Exact Mass: 432.19 Molecular Weight: 432.47

ESI-MS $[M+H]^+$ calcd for $C_{22}H_{28}N_2O_7H^+$ 433.20 found 433.4.

Example 10

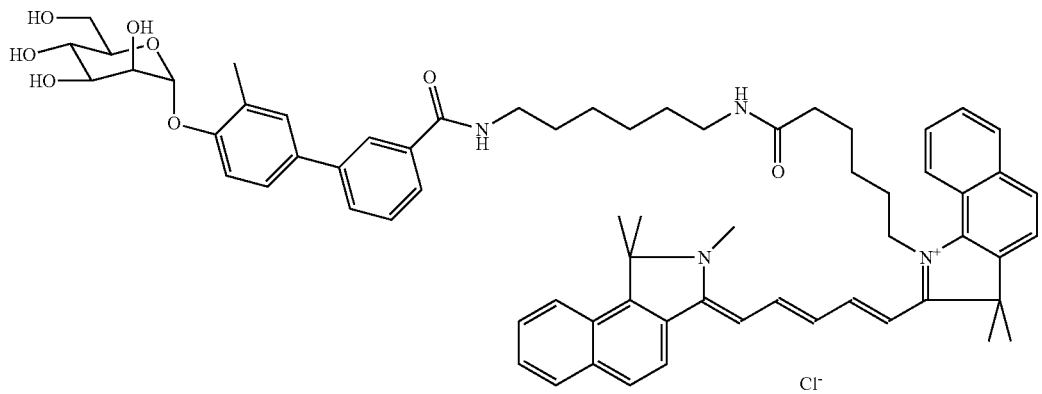

N-(Cyanine5.5)-4'-(α-D-mannopyranosyl)-3'-methyl-[1,1'biphenyl]-3-carboxamide chloride (10) 23 was made following the coupling procedure for 7, utilizing 4'-(α-D-mannopyranosyloxy)-3'-methyl-[1,1'biphenyl]-3-carboxylic acid (loc. cit.) (12.4 mg, 0.032 mmol) and HATU (12.2 mg, 0.032 mmol) in dry DMF (2 mL), followed by commercially available Cyanine5.5amine (Lumiprobe, #7000) (20 mg, 0.027 mmol) and DIPEA (28 µL, 0.16 mmol), to give the product in 69% yield.

Formula: $C_{66}H_{77}N_4O_8^+$ Exact Mass: 1053.57 Molecular Weight: 1054.34

ESI-MS $[M]^+$ calcd for $C_{66}H_{77}N_4O_8^+$ 1053.57 found 1053.9.

Example 11

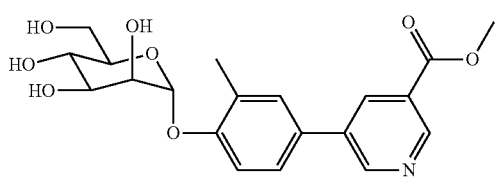

5-[4'-(α-D-mannopyranosyloxy)-3'-methylphenyl]-3-pyridinecarboxylic acid methyl ester (11) Mannosyl boronate ester (102) and commercially available 5-bromo-3-pyridinecarboxylic acid methyl ester were reacted via the standard Suzuki coupling procedure (1.5 h at 80° C.), followed by the acetate deprotection protocol (2 h at rt), to give the product in 34% yield.

Formula: $C_{20}H_{23}NO_8$ Exact Mass: 405.14 Molecular Weight: 405.40

$^1$H NMR (400 MHz, methanol-$d_4$) δ ppm 9.01 (d, J=2.0 Hz, 1H) 8.94 (d, J=2.3 Hz, 1H) 8.52 (t, J=2.2 Hz, 1H) 7.46-7.53 (m, 2H) 7.35 (d, J=8.2 Hz, 1H) 5.56 (s, 1H) 4.03-4.07 (m, 1H) 3.96 (s, 3H) 3.91-3.95 (m, 1H) 3.67-3.79 (m, 3H) 3.52-3.58 (m, 1H) 2.31 (s, 3H).

ESI-MS $[M+H]^+$ calcd for $C_{20}H_{23}NO_8H^+$ 406.15 found 406.3.

Example 12

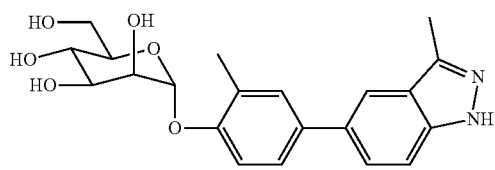

3-Methyl-5-[4'-(α-D-mannopyranosyloxy) 3'-methylphenyl]-1H-indazole (12) Mannosyl boronate ester (102) and commercially available 5-bromo-3-methyl-1H-indazole were reacted via the standard Suzuki coupling procedure (1.5 h at 80° C.), followed by the acetate deprotection protocol (2 h at rt), to give the product in 41% yield.

Formula: $C_{21}H_{24}N_2O_6$ Exact Mass: 400.16 Molecular Weight: 400.43

$^1$H NMR (400 MHz, methanol-$d_4$) δ ppm 7.85 (s, 1H) 7.65 (d, J=8.6 Hz, 1H) 7.41-7.52 (m, 3H) 7.29 (d, J=8.6 Hz, 1H) 5.54 (s, 1H) 4.08 (br. s., 1H) 3.98 (dd, J=9.4, 3.1 Hz, 1H) 3.71-3.82 (m, 3H) 3.60-3.66 (m, 1H) 2.60 (s, 3H) 2.32 (s, 3H); ESI-MS $[M+H]^+$ calcd for $C_{21}H_{24}N_2O_6H^+$ 401.17 found 401.3.

Example 13

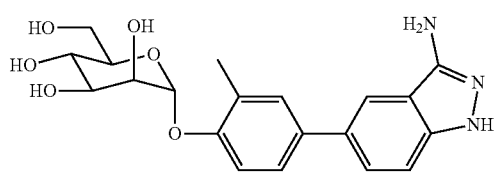

5-[4'-(α-D-mannopyranosyloxy)-3'-methylphenyl]-1H-indazol-3-amine (13)

Mannosyl boronate ester (102) and commercially available 5-bromo-1H-indazol-3-amine were reacted via the standard Suzuki coupling procedure (1.5 h at 80° C.), followed by the acetate deprotection protocol (2 h at rt), to give the product in 4% yield.

Formula: $C_{20}H_{23}N_3O_6$ Exact Mass: 401.16 Molecular Weight: 401.41

$^1$H NMR (400 MHz, methanol-$d_4$) δ ppm 8.07-8.09 (m, 1H) 7.86 (dd, J=9.0, 1.6 Hz, 1H) 7.42-7.48 (m, 3H) 7.31 (d, J=8.6 Hz, 1H) 5.55 (d, J=1.6 Hz, 1H) 4.07-4.09 (m, 1H) 3.97 (dd, J=9.4, 3.5 Hz, 1H) 3.71-3.82 (m, 3H) 3.58-3.64 (m, 1H) 2.32 (s, 3H); ESI-MS [M+H]$^+$ calcd for $C_{20}H_{23}N_3O_6H^+$ 402.17 found 402.4.

Example 14

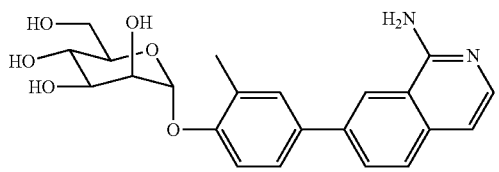

7-[4'-(α-D-mannopyranosyloxy)-3'-methylphenyl]-isoquinolin-1-amine (14)

Mannosyl boronate ester (102) and commercially available 7-bromoisoquinolin-1-amine were reacted via the standard Suzuki coupling procedure (1.5 h at 80° C.), followed by the acetate deprotection protocol (2 h at rt), to give the product in 36% yield.

Formula: $C_{22}H_{24}N_2O_6$ Exact Mass: 412.16 Molecular Weight: 412.44

$^1$H NMR (400 MHz, methanol-$d_4$) δ ppm 8.64 (s, 1H) 8.21 (d, J=8.6 Hz, 1H) 7.93 (d, J=8.6 Hz, 1H) 7.64 (s, 1H) 7.59 (d, J=8.6 Hz, 1H) 7.52 (d, J=7.0 Hz, 1H) 7.36 (d, J=8.2 Hz, 1H) 7.21 (d, J=6.7 Hz, 1H) 5.60 (s, 1H) 4.10 (br. s., 1H) 3.98 (dd, J=9.4, 3.1 Hz, 1H) 3.72-3.83 (m, 3H) 3.57-3.64 (m, 1H) 2.34 (s, 3H); ESI-MS [M+H]$^+$ calcd for $C_{22}H_{24}N_2O_6H^+$ 413.17 found 413.4.

Example 15

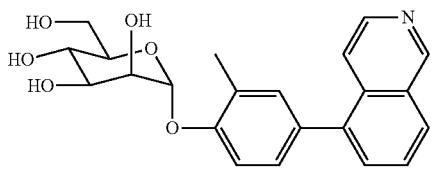

5-[4'-(α-D-mannopyranosyloxy)-3'-methylphenyl]-isoquinoline (15)

Mannosyl boronate ester (102) and commercially available 5-bromoisoquinoline were reacted via the standard Suzuki coupling procedure (1.5 h at 80° C.), followed by the acetate deprotection protocol (3 h at rt), to give the product in 39% yield.

Formula: $C_{22}H_{23}NO_6$ Exact Mass: 397.15 Molecular Weight: 397.42

$^1$H NMR (400 MHz, methanol-$d_4$) δ ppm 9.75 (s, 1H) 8.50 (d, J=7.0 Hz, 1H) 8.45 (d, J=8.2 Hz, 1H) 8.32 (d, J=6.7 Hz, 1H) 8.09-8.14 (m, 1H) 8.02-8.08 (m, 1H) 7.44 (d, J=8.2 Hz, 1H) 7.30-7.37 (m, 2H) 5.63 (d, J=1.6 Hz, 1H) 4.09-4.12 (m, 1H) 3.99 (dd, J=9.4, 3.5 Hz, 1H) 3.71-3.85 (m, 3H) 3.59-3.65 (m, 1H) 2.35 (s, 3H); ESI-MS [M+H]$^+$ calcd for $C_{22}H_{23}NO_6H^+$ 398.16 found 398.4.

Example 16

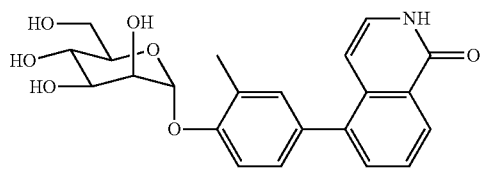

5-[4'-(α-D-mannopyranosyloxy)-3'-methylphenyl]-1(2H)-isoquinolinone (16)

Mannosyl boronate ester (102) and commercially available 5-bromo-1(2H)-isoquinolinone were reacted via the standard Suzuki coupling procedure (1.5 h at 80° C.), followed by the acetate deprotection protocol (2 h at rt), to give the product in 10% yield.

Formula: $C_{22}H_{23}NO_7$ Exact Mass: 413.15 Molecular Weight: 413.42

$^1$H NMR (400 MHz, methanol-$d_4$) δ ppm 8.32 (d, J=7.8 Hz, 1H) 7.58-7.64 (m, 1H) 7.50-7.57 (m, 1H) 7.34 (d, J=8.2 Hz, 1H) 7.15-7.22 (m, 2H) 7.12 (d, J=7.0 Hz, 1H) 6.63 (d, J=7.4 Hz, 1H) 5.59 (s, 1H) 4.10 (br. s., 1H) 3.96-4.02 (m, 1H) 3.72-3.85 (m, 3H) 3.61-3.68 (m, 1H) 2.31 (s, 3H); ESI-MS [M+H]$^+$ calcd for $C_{22}H_{23}NO_7H^+$ 414.16 found 414.4.

Example 17

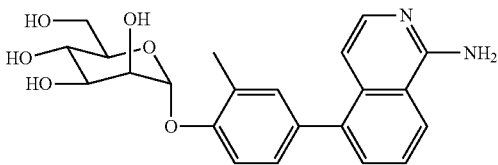

5-[4'-(α-D-mannopyranosyloxy)-3'-methylphenyl]-isoquinolin-1-amine (17)

Mannosyl boronate ester (102) and commercially available 5-bromoisoquinolin-1-amine were reacted via the standard Suzuki coupling procedure (1.5 h at 80° C.), followed by the acetate deprotection protocol (2 h at rt), to give the product in 30% yield.

Formula: $C_{22}H_{24}N_2O_6$ Exact Mass: 412.16 Molecular Weight: 412.44

$^1$H NMR (400 MHz, methanol-$d_4$) δ ppm 8.39-8.46 (m, 1H) 7.84 (dd, J=19.2, 7.0 Hz, 2H) 7.49-7.55 (m, 1H) 7.36-7.43 (m, 1H) 7.11-7.27 (m, 3H) 5.63 (d, J=4.3 Hz, 1H) 4.14 (br. s., 1H) 3.98-4.06 (m, 1H) 3.74-3.88 (m, 3H) 3.60-3.71 (m, 1H) 2.33 (d, J=5.5 Hz, 3H); ESI-MS [M+H]$^+$ calcd for $C_{22}H_{24}N_2O_6H^+$ 413.17 found 413.4.

Example 18

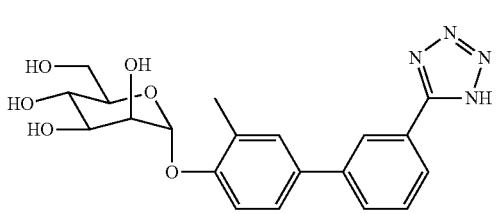

3-Methyl-3'-(2H-tetrazol-5-yl)[1,1'-biphenyl]-4-yl α-D-mannopyranoside (18)

Mannosyl bromide (101) and commercially available B-[3-(2H-tetrazol-5-yl)phenyl] boronic acid were reacted via the standard Suzuki coupling procedure (1.5 h at 80° C., then 1 h at 100° C.), followed by the acetate deprotection protocol (30 min at rt), to give the product in 3% yield.

Formula: $C_{20}H_{22}N_4O_6$ Exact Mass: 414.15 Molecular Weight: 414.41

$^1$H NMR (400 MHz, methanol-$d_4$) δ ppm 8.25 (s, 1H) 7.95 (d, J=7.8 Hz, 1H) 7.80 (d, J=7.8 Hz, 1H) 7.60-7.65 (m, 1H) 7.46-7.54 (m, 2H) 7.33 (d, J=8.2 Hz, 1H) 5.57 (s, 1H) 4.07-4.10 (m, 1H) 3.98 (dd, J=9.2, 2.9 Hz, 1H) 3.70-3.82 (m, 3H) 3.57-3.64 (m, 1H) 2.33 (s, 3H); ESI-MS [M+H]$^+$ calcd for $C_{20}H_{22}N_4O_6H^+$ 415.16 found 415.3, (829.6 2M+H).

Example 19

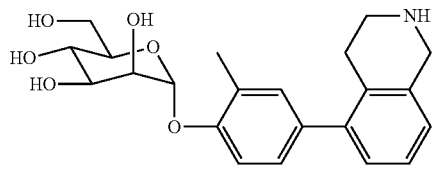

1,2,3,4-Tetrahydro-5-[4'-(α-D-mannopyranosyloxy)-3'-methylphenyl]-isoquinoline (19) 5-[4'-(α-D-mannopyranosyloxy)-3'-methylphenyl]-isoquinoline (Han, Z. et al, *J. Med. Chem.* 2012, 55(8), 3945-3959.) (10 mg, 0.052 mmol) was dissolved into MeOH (3 mL), and 10% wt. Pd/C (10 mg) was added. The reaction was then stirred under 1 atm of H$_2$ for 5 h, whereupon the reaction was filtered, and the filtrate was concentrated in vacuo, giving 19 as the major product. The resulting residue was purified by HPLC (C18, 15*150 mm column; eluent: acetonitrile/water (0.05% TFA), to give 15 in 42% yield Formula: $C_{21}H_{25}NO_6$ Exact Mass: 387.17 Molecular Weight: 387.43

ESI-MS [M+H]$^+$ calcd for $C_{21}H_{25}NO_6H^+$ 388.18 found 388.4.

Example 20

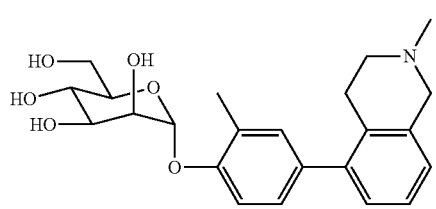

1,2,3,4-Tetrahydro-5-[4'-(α-D-mannopyranosyloxy)-3'-methylphenyl]-N-methylisoquinoline (20) 5-[4'-(α-D-mannopyranosyloxy)-3'-methylphenyl]-isoquinoline (Han, Z. et al, *J. Med. Chem.* 2012, 55(8), 3945-3959.) (10 mg, 0.052 mmol) was dissolved into MeOH (3 mL), and 10% wt. Pd/C (10 mg) was added. The reaction was then stirred under 1 atm of H$_2$ for 48 h, whereupon the reaction was filtered, and the filtrate was concentrated in vacuo, giving the title compound as the major product. The resulting residue was purified by HPLC (C18, 15*150 mm column; eluent: acetonitrile/water (0.05% TFA), to give the product in 42% yield Formula: $C_{22}H_{27}NO_6$ Exact Mass: 401.18 Molecular Weight: 401.45

ESI-MS [M+H]$^+$ calcd for $C_{22}H_{27}NO_6H^+$ 402.19 found 402.4.

Example 21

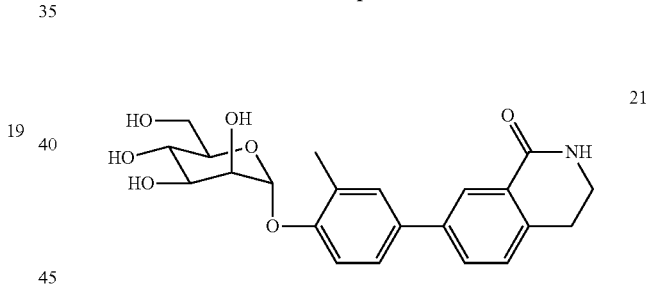

3,4-Dihydro-7-[4'-(α-D-mannopyranosyloxy)-3'-methylphenyl]-1(2H)-iso-quinolinone (21) 7-[4'-(α-D-mannopyranosyloxy)-3'-methylphenyl]-isoquinolin-1-one (Han, Z. et al, *J. Med. Chem.* 2012, 55(8), 3945-3959.) (30 mg, 0.073 mmol) was dissolved into MeOH (3 mL), and 10% wt. Pd/C (30 mg) was added. The reaction was then stirred under 1 atm of H$_2$ for 16 h, whereupon the reaction was filtered, and the filtrate was concentrated in vacuo. The resulting residue was purified by HPLC (C18, 15*150 mm column; eluent: acetonitrile/water (0.05% TFA), to give the product in 99% yield.

Formula: $C_{22}H_{25}NO_7$ Exact Mass: 415.16 Molecular Weight: 415.44

$^1$H NMR (400 MHz, methanol-$d_4$) δ ppm 8.14 (s, 1H) 7.70 (d, J=7.8 Hz, 1H) 7.40-7.47 (m, 2H) 7.31 (dd, J=19.4, 8.0 Hz, 2H) 5.55 (s, 1H) 4.08 (br. s., 1H) 3.97 (d, J=9.4 Hz, 1H) 3.72-3.81 (m, 3H) 3.57-3.65 (m, 1H) 3.49-3.55 (m, 2H) 2.96-3.03 (m, 2H) 2.30 (s, 3H); ESI-MS [M+H]$^+$ calcd for $C_{22}H_{25}NO_7H^+$ 416.17 found 416.4, (831.6 2M+1).

Example 22

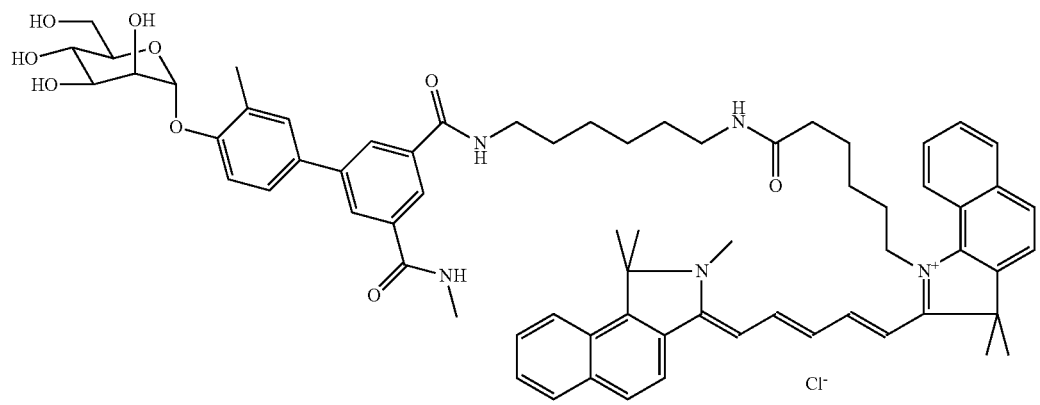

N³-(Cyanine5.5)-4'-(α-D-mannopyranosyl)-N⁵,3'-dimethyl-[1,1'biphenyl]-3,5-dicarboxamide chloride (22) Into a flask containing EtOH (5 mL) was dissolved commercially available 5-bromo-1,3-benzenedicarboxylic acid 1,3-dimethyl ester (300 mg, 1.10 mmol). MeNH$_2$ (33% wt. in EtOH; 0.132 mL, 1.10 mmol), and the reaction was allowed to stir for 16 h at rt. Upon completion, the reaction contents were evaporated, and the crude benzamide intermediate was taken forward (220 mg, 0.80 mmol) and reacted with boronate ester 102 (225 mg, 0.40 mmol) via the standard Suzuki protocol, to give intermediate 4'-(α-D-mannopyranosyl)-N,3'-dimethyl-5-[(methylamino)carbonyl]-[1,1'biphenyl]-3-carboxylic acid methyl ester (160 mg 0.254 mmol). Saponification was then carried out by dissolving the residue in methanol (2 mL) and THF (2 mL) and adding 1M NaOH (2 mL) and stirring overnight at rt. The resultant carboxylic acid was then neutralized with saturated aq. 1M HCl, and concentrated in vacuo. Once dry, the crude carboxylic acid was coupled to Cyanine5.5amine (211 mg, 0.279 mmol) following the same coupling procedure and reagent ratios as detailed in the synthesis of 7, to give the product in an overall yield of 3% (starting from 5-bromo-1,3-benzenedicarboxylic acid 1,3-dimethyl ester)

Formula: $C_{68}H_{80}N_5O_9^+$ Exact Mass: 1110.60 Molecular Weight: 1111.39

ESI-MS [M]$^+$ calcd for $C_{68}H_{80}N_5O_9^+$ 1110.60 found 1110.8.

Example 23

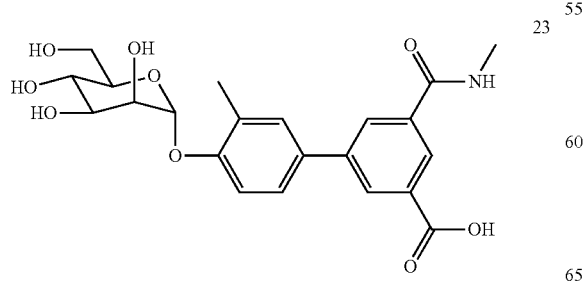

4'-(α-D-mannopyranosyloxy)-3'-methyl-5-[(methylamino)carbonyl]-[1,1'biphenyl]-3-carboxylic acid (23) Into a flask containing EtOH (5 mL) was dissolved commercially available 5-bromo-1,3-benzenedicarboxylic acid 1,3-dimethyl ester (300 mg, 1.10 mmol). MeNH$_2$ (33% wt. in EtOH; 0.132 mL, 1.10 mmol), and the reaction was allowed to stir for 16 h at rt. Upon completion, the reaction contents were evaporated, and the crude benzamide intermediate was produced as a mixture of N-methyl 5-bromo-3-carbomethoxy-benzenecarboxamide and N-methyl 5-bromo-3-carboethoxy-benzenecarboxamide (220 mg, 0.80 mmol). The mixture was reacted with boronate ester 102 (225 mg, 0.40 mmol) via the standard Suzuki protocol, to give intermediate 4'-(α-D-mannopyranosyloxy)-3'-methyl-5-[(methylamino)carbonyl]-[1,1'biphenyl]-3-carboxylic acid methyl ester (160 mg 0.254 mmol). Saponification was then carried out by dissolving the residue in methanol (2 mL) and THF (2 mL) and adding 1M NaOH (2 mL) and stirring overnight at rt. The resultant carboxylic acid was then neutralized with saturated aq. 1M HCl, and concentrated in vacuo to give the title product. $^1$H NMR (400 MHz, dimethylsulfoxide-d$_6$) δ ppm 8.68-8.74 (m, 1H) 8.35 (s, 1H) 8.29 (s, 1H) 8.25 (s, 1H) 7.59 (s, 1H) 7.55 (d, J=8.6 Hz, 1H) 7.29 (d, J=8.6 Hz, 1H) 5.47 (s, 1H) 5.04 (d, J=3.5 Hz, 1H) 4.84 (d, J=5.1 Hz, 1H) 4.75 (br. s., 1H) 4.45 (t, J=5.7 Hz, 1H) 3.90 (br. s., 1H) 3.72-3.78 (m, 1H) 3.58-3.65 (m, 1H) 3.44-3.57 (m, 2H) 3.37-3.44 (m, 2H) 2.83 (d, J=4.7 Hz, 3H) 2.28 (s, 3H), ESI-MS [M+H]$^+$ calcd for C$_{22}$H$_{25}$NO$_9$ 448.16 found 448.3.

Formula: C$_{22}$H$_{25}$NO$_9$ Exact Mass: 447.15, Molecular Weight: 447.44,

Example 24

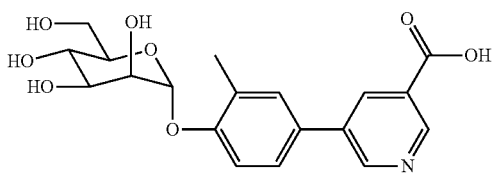

5-[4'-(α-D-mannopyranosyloxy)-3'-methylphenyl]-3-pyridinecarboxylic acid (24) 11 (15 mg, 0.037 mmol) was dissolved in MeOH (2 mL), followed by the addition of 0.2M aq. NaOH (2 mL). The reaction was stirred for 3 h and then neutralized with H$^+$ exchange resin (DOWEX 50WX4-100). The resin was removed by filtration, and the filtrate was concentrated in vacuo. The resulting compound was lyophilized to give the pure compound in 18% yield.

Formula: C$_{19}$H$_{21}$NO$_8$ Exact Mass: 391.13 Molecular Weight: 391.37

$^1$H NMR (400 MHz, methanol-d$_4$) δ ppm 8.97-9.07 (m, 1H) 8.85-8.93 (m, 1H) 8.50-8.57 (m, 1H) 7.47-7.56 (m, 2H) 7.37 (d, J=8.2 Hz, 1H) 5.58 (s, 1H) 4.05-4.09 (m, 1H) 3.94-3.99 (m, 1H) 3.72-3.80 (m, 3H) 3.50-3.61 (m, 1H) 2.33 (s, 3H); ESI-MS [M+H]$^+$ calcd for C$_{19}$H$_{21}$NO$_8$H$^+$ 392.13 found 392.3.

Example 25

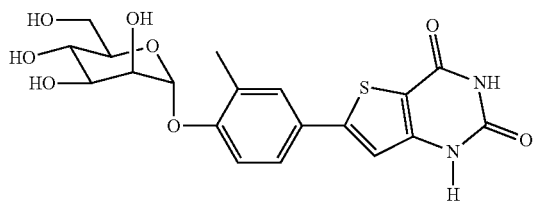

6-[4'-(α-D-mannopyranosyloxy)-3'-methylphenyl]-thieno[3,2-d]pyrimidine-2,4(1H,3H)-dione (25) Mannosyl boronate ester (102) and commercially available 3-[(aminocarbonyl)amino]-5-bromo-2-thiophenecarboxylic acid methyl ester were reacted via the standard Suzuki coupling procedure (1.5 h at 80° C.). Next, the crude material was dissolved into MeNH$_2$ (33% wt. in EtOH; 5 mL), and the reaction was allowed to stir for 16 h at rt. Upon completion, the reaction contents were evaporated, and the crude material was separated and purified by HPLC (C18, 15*150 mm column; eluent: acetonitrile/water (0.05% TFA) to give the title compound 25 in 15% yield.

Formula: C$_{19}$H$_{20}$N$_2$O$_8$S Exact Mass: 436.09 Molecular Weight: 436.44 $^1$H NMR (400 MHz, dimethylsulfoxide-d$_6$) δ ppm 11.61 (s, 1H) 11.17 (s, 1H) 7.58 (s, 1H) 7.53 (d, J=8.6 Hz, 1H) 7.24 (d, J=8.6 Hz, 1H) 7.09 (s, 1H) 5.48 (s, 1H) 5.06 (d, J=4.3 Hz, 1H) 4.83 (d, J=5.9 Hz, 1H) 4.76 (d, J=5.9 Hz, 1H) 4.42 (t, J=5.9 Hz, 1H) 3.85-3.90 (m, 1H) 3.68-3.75 (m, 1H) 3.56-3.62 (m, 1H) 3.42-3.55 (m, 3H) 2.23 (s, 3H); ESI-MS [M+H]$^+$ calcd for C$_{19}$H$_{20}$N$_2$O$_8$SH$^+$ 437.10 found 437.3.

Example 26

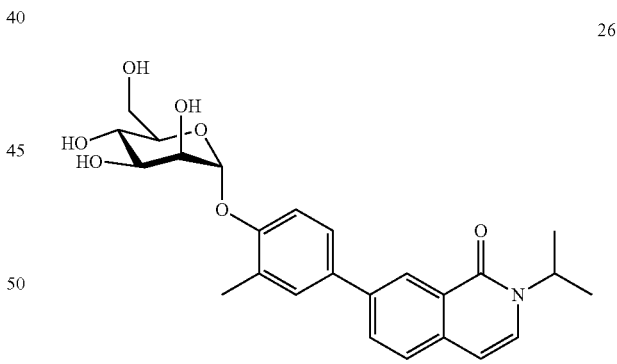

2-isopropyl-7-[4'-(α-D-mannopyranosyloxy)-3'-methylphenyl]-1(2H)-isoquinolinone Following Scheme IVb, mannosyl bromide (101) and 2-isopropyl-7-(4,4,5,5-tetramethyl-1,3,2-dioxaborolan-2-yl)isoquinolin-1(2H)-one were reacted via the standard Suzuki coupling procedure (40 min at 80° C.), followed first by the acetate deprotection protocol (1 h at rt) and then by purification using Prep-HPLC with conditions: Column: XBridge Shield Prep C18 OBD Column 19×150 mm, 5 μm; Mobile Phase A: Water with 0.05% ammonium bicarbonate, Mobile Phase B: acetonitrile; Flow rate: 20 mL/min; Gradient: 5% B to 45% B in 13 min; 254 nm, Rt: 12.5 min to afford the title compound (44.0 mg, 25% for two steps) as a white solid.

C$_{25}$H$_{29}$NO$_7$ Exact Mass: 455.19 Molecular Weight: 455.50.

$^1$H NMR (400 MHz, CD$_3$OD) δ: 8.52 (d, J=1.2 Hz, 1H), 7.95 (dd, J=8.0, 2.0 Hz, 1H), 7.67 (d, J=7.6 Hz, 1H), 7.54-7.51 (m, 2H), 7.44 (d, J=7.6 Hz, 1H), 7.33 (d, J=8.4 Hz, 1H), 6.77 (d, J=7.6 Hz, 1H), 5.57 (d, J=1.2 Hz, 1H), 5.40-5.30 (m, 1H), 4.09-4.08 (m, 1H), 3.98 (dd, J=9.6, 2.4 Hz, 1H), 3.81-3.72 (m, 3H), 3.63-3.58 (m, 1H), 2.33 (s, 3H), 1.43 (d, J=6.8 Hz, 6H). ESI-MS [M+H]$^+$ calcd for (C$_{25}$H$_{29}$NO$_7$H$^+$) 456.20, found 456.10.

Example 27

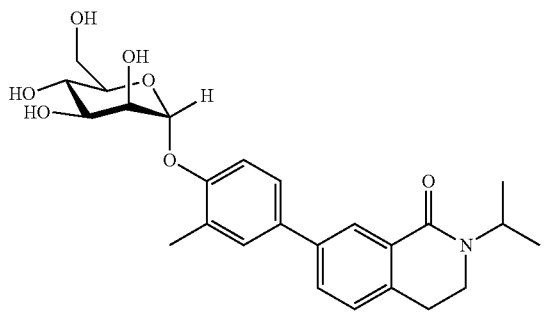

27

2-isopropyl-3,4-Dihydro-7-[4'-(α-D-mannopyranosyloxy)-3'-methylphenyl]-1(2H)-isoquinolinone Following Scheme IVa, boronic ester 102 and 7-bromo-2-isopropyl-3,4-dihydroisoquinolin-1(2H)-one were reacted via the standard Suzuki coupling procedure (40 min at 80° C.), followed first by the acetate deprotection protocol (2 h at rt) and then by purification using Prep-HPLC with conditions: Column: XBridge Prep C18 OBD Column, 100 Å, 5 μm, 19×250 mm; Mobile Phase A: Water with 0.05% ammonium bicarbonate, Mobile Phase B: acetonitrile; Flow rate: 20 mL/min; Gradient: 25% B to 36% B in 8 min; 254 nm; Rt: 6.62 min to afford the title compound (33.0 mg, 27% for two steps) as a white solid.

Formula: C$_{25}$H$_{31}$NO$_7$ Exact Mass: 457.21 Molecular Weight: 457.52.

Analytical data: $^1$H NMR (300 MHz, CD$_3$OD) δ: 8.14 (d, J=1.8 Hz, 1H), 7.68 (dd, J=7.4 Hz, 2.1 Hz, 1H), 7.45-7.41 (m, 2H), 7.33-7.28 (m, 2H), 5.54 (d, J=1.5 Hz, 1H), 5.05-4.96 (m, 1H), 4.08-4.06 (m, 1H), 3.97 (dd, J=9.3 Hz, 3.3 Hz, 1H), 3.81-3.70 (m, 3H), 3.63-3.57 (m, 1H), 3.53 (t, J=6.3 Hz, 2H), 2.99 (t, J=6.3 Hz, 2H), 2.30 (s, 3H), 1.25 (d, J=6.6 Hz, 6H). ESI-MS [M+H]$^+$ calcd for (C$_{25}$H$_{31}$NO$_7$H$^+$) 458.22, found 458.10.

Example 28

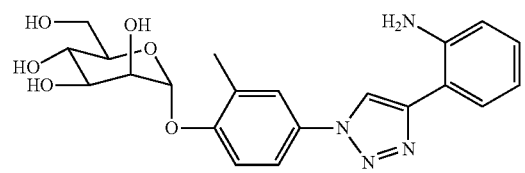

28

2-methyl-4-[4-(2-aminophenyl)-1H-1,2,3-triazol-1-yl]phenyl α-D-mannopyranoside The two-step deprotection/click procedure used to make Example 2 was followed with modification of the second step by dissolving the crude 4-azido-2-methylphenyl-α-D-mannopyranoside from the first step with 2-ethynylaniline in (2:1, v/v) THF/DMF (3 mL) and stirring for 24 h. Upon completion, saturated aq. NH$_4$Cl was added, and the reaction was stirred 1 h. The solvents were evaporated under reduced pressure, and the residue was triturated with DCM/Hexanes (9:1, v/v). The remaining solid was then purified by by HPLC (C18, 15*150 mm column; eluent: acetonitrile/water (0.05% TFA) to afford the title product in 11% yield.

Formula: C$_{21}$H$_{24}$N$_4$O$_6$ Exact Mass: 428.17 Molecular Weight: 428.45

$^1$H NMR (400 MHz, methanol-d$_4$) δ ppm 8.78-8.93 (m, 1H), 7.75 (d, J=5.0 Hz, 1H), 7.51-7.68 (m, 2H), 7.26-7.43 (m, 2H), 7.10 (br. s., 2H), 5.51 (s, 1H), 4.00 (br. s., 1H), 3.87 (dd, J=9.4, 3.2 Hz, 1H), 3.57-3.75 (m, 3H), 3.42-3.52 (m, 1H), 2.14-2.36 (m, 3H); ESI-MS [M+H]$^+$ calcd for C$_{21}$H$_{24}$N$_4$O$_6$H$^+$ 429.18 found 429.3.

Example 29

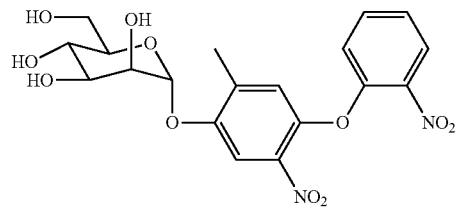

29

2-[4-(α-D-mannopyranosyloxy)-5-methyl-2-nitrophenoxy]nitrobenzene was obtained in 37% yield following the same two-step S$_N$Ar/deprotection procedure used to make Example 1, employing 2-nitrophenol and using a modified volume of DMF (1.0 mL).

Formula: C$_{19}$H$_{20}$N$_2$O$_{11}$ Exact Mass: 452.11 Molecular Weight: 452.37

$^1$H NMR (400 MHz, methanol-d$_4$) δ ppm 8.00 (d, J=8.2 Hz, 1H), 7.96 (s, 1H), 7.59 (t, J=7.6 Hz, 1H), 7.26-7.33 (m, 1H), 7.12 (s, 1H), 7.00 (d, J=8.2 Hz, 1H), 5.62 (s, 1H), 4.07-4.11 (m, 1H), 3.92 (dd, J=9.6, 3.3 Hz, 1H), 3.68-3.84 (m, 3H), 3.54 (td, J=6.3, 2.7 Hz, 1H), 2.30 (s, 3H); ESI-MS [M+Na]$^+$ calcd for C$_{19}$H$_{20}$N$_2$O$_{11}$Na$^+$ 475.10 found 475.2.

Example 30

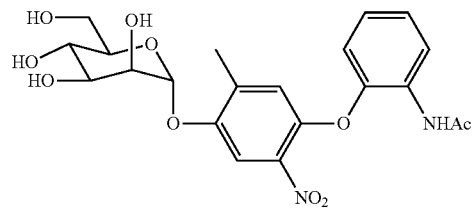

30

N-(2-[4-(α-D-mannopyranosyloxy)-5-methyl-2-nitrophenoxy]phenyl)acetamide was obtained in 40% yield following the same two-step S$_N$Ar/deprotection procedure used to make Example 1, employing 2-acetamidophenol and using a modified volume of DMF (1.0 mL) and a reaction temperature of 25° C.

Formula: $C_{21}H_{24}N_2O_{10}$ Exact Mass: 464.14 Molecular Weight: 464.43.

$^1$H NMR (400 MHz, methanol-d$_4$) δ ppm 7.83 (d, J=9.8 Hz, 1H), 7.41 (t, J=7.8 Hz, 1H), 7.26 (t, J=7.8 Hz, 1H), 7.17 (d, J=7.8 Hz, 1H), 7.03 (d, J=7.8 Hz, 1H), 6.89 (t, J=7.4 Hz, 1H), 5.55-5.65 (m, 1H), 4.05 (d, J=10.6 Hz, 1H), 3.85-3.95 (m, 1H), 3.63-3.84 (m, 3H), 3.42-3.58 (m, 1H), 2.20 (s, 3H), 1.97 (s, 3H); ESI-MS [M+H]$^+$ calcd for $C_{21}H_{24}N_2O_{10}H^+$ 465.15 found 465.3.

Example 31

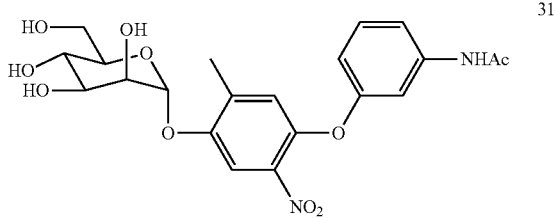 [SMILES: CC(=O)Nc1cccc(Oc2cc(C)c(OC3OC(CO)C(O)C(O)C3O)cc2[N+](=O)[O-])c1]

N-(3-[4-(α-D-mannopyranosyloxy)-5-methyl-2-nitrophenoxy]phenyl)acetamide was obtained in 45% yield following the same two-step S$_N$Ar/deprotection procedure used to make Example 1, employing 3-acetamidophenol and using a modified volume of DMF (1.0 mL) and a reaction temperature of 25° C.

Formula: $C_{21}H_{24}N_2O_{10}$ Exact Mass: 464.14 Molecular Weight: 464.43

$^1$H NMR (400 MHz, methanol-d$_4$) δ ppm 7.87 (s, 1H), 7.20-7.32 (m, 3H), 7.03 (s, 1H), 6.67 (d, J=7.0 Hz, 1H), 5.58 (s, 1H), 4.08 (d, J=1.6 Hz, 1H), 3.92 (dd, J=9.4, 3.5 Hz, 1H), 3.68-3.85 (m, 3H), 3.51-3.60 (m, 1H), 2.27 (s, 3H), 2.09 (s, 3H); ESI-MS [M+H]$^+$ calcd for $C_{21}H_{24}N_2O_{10}H^+$ 465.15 found 465.2.

Example 32

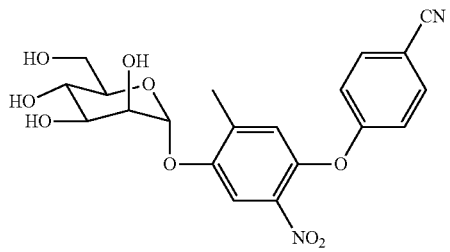

4-[4-(α-D-mannopyranosyloxy)-5-methyl-2-nitrophenoxy]benzonitrile was obtained in 71% yield following the same two-step S$_N$Ar/deprotection procedure used to make Example 1, employing 4-hydroxylbenzonitrile and using a modified volume of DMF (1.0 mL), and an extended reaction time of 25° C. for 24 h, followed by 24 h at 40° C.

Formula: $C_{20}H_{20}N_2O_9$ Exact Mass: 432.12 Molecular Weight: 432.39

$^1$H NMR (400 MHz, methanol-d$_4$) δ ppm 7.95 (s, 1H), 7.70 (d, J=9.0 Hz, 2H), 7.18 (s, 1H), 7.04 (d, J=9.0 Hz, 2H), 5.63 (s, 1H), 4.07-4.12 (m, 1H), 3.93 (dd, J=9.6, 3.3 Hz, 1H), 3.69-3.84 (m, 3H), 3.54 (td, J=6.3, 2.7 Hz, 1H), 2.32 (s, 3H); ESI-MS [M+H]$^+$ calcd for $C_{20}H_{20}N_2O_9H^+$ 433.12 found 433.2.

Example 33

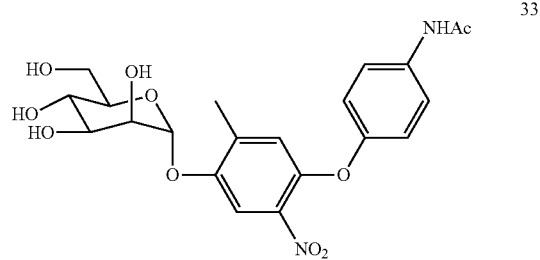 [SMILES: CC(=O)Nc1ccc(Oc2cc(C)c(OC3OC(CO)C(O)C(O)C3O)cc2[N+](=O)[O-])cc1]

N-(4-[4-(α-D-mannopyranosyloxy)-5-methyl-2-nitrophenoxy]phenyl)acetamide was obtained in 45% yield following the same two-step SNAr/deprotection procedure used to make Example 1, employing 4-acetamidophenol and using a modified volume of DMF (1.0 mL) and a reaction temperature of 25° C.

Formula: $C_{21}H_{24}N_2O_{10}$ Exact Mass: 464.14 Molecular Weight: 464.43

$^1$H NMR (400 MHz, methanol-d$_4$) δ ppm 7.75 (s, 1H), 7.42 (d, J=8.6 Hz, 2H), 6.79-6.88 (m, 3H), 5.47 (s, 1H), 3.98 (br. s., 1H), 3.81 (dd, J=9.4, 3.5 Hz, 1H), 3.59-3.74 (m, 3H), 3.41-3.48 (m, 1H), 2.15 (s, 3H), 2.01 (s, 3H); ESI-MS [M+H]$^+$ calcd for $C_{21}H_{24}N_2O_{10}H^+$ 465.15 found 465.3.

Example 34

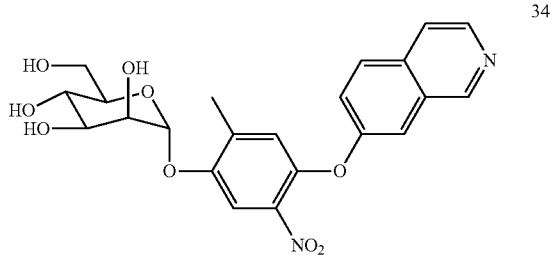 [SMILES: Cc1cc(Oc2ccc3ccncc3c2)c([N+](=O)[O-])cc1OC1OC(CO)C(O)C(O)C1O]

7-[4-(α-D-mannopyranosyloxy)-5-methyl-2-nitrophenoxy]isoquinoline was obtained in 37% yield following the same two-step SNAr/deprotection procedure used to make Example 1, employing 7-hydroxyisoquinoline and using a modified volume of DMF (1.0 mL) and a reaction temperature of 25° C.

Formula: $C_{22}H_{22}N_2O_9$ Exact Mass: 458.13 Molecular Weight: 458.42

$^1$H NMR (400 MHz, methanol-d$_4$) δ ppm 9.39 (s, 1H), 8.38 (d, J=6.3 Hz, 1H), 8.28 (d, J=6.7 Hz, 1H), 8.20 (d, J=9.0 Hz, 1H), 7.92 (s, 1H), 7.86 (dd, J=9.0, 2.3 Hz, 1H), 7.55 (d, J=2.0 Hz, 1H), 7.21 (s, 1H), 5.57 (s, 1H), 4.01-4.05 (m, 1H), 3.86 (dd, J=9.6, 3.3 Hz, 1H), 3.61-3.78 (m, 3H), 3.47 (td, J=6.3, 2.7 Hz, 1H), 2.26 (s, 3H); ESI-MS [M+H]$^+$ calcd for $C_{22}H_{22}N_2O_9H^+$ 459.14 found 459.3.

Example 35

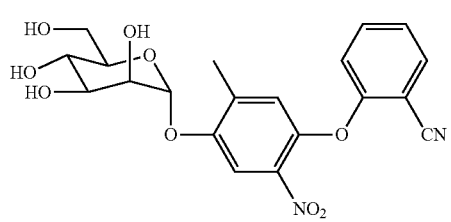

2-[4-(α-D-mannopyranosyloxy)-5-methyl-2-nitrophenoxy]benzonitrile was obtained in 40% yield similar to the two-step $S_NAr$/deprotection procedure used to make Example 1, employing 2-hydroxylbenzonitrile and using a modified volume of DMF (1.0 mL) and an extended reaction time of 25° C. for 24 h, followed by 24 h at 40° C., after which an additional 2 equivalents of 2-hydroxybenzonitrile and 0.5 equivalents of $Cs_2CO_3$ were added and the reaction was stirred another 48 h at 40° C.

Formula: $C_{20}H_{20}N_2O_9$ Exact Mass: 432.12 Molecular Weight: 432.39

$^1$H NMR (400 MHz, methanol-$d_4$) δ ppm 7.98 (d, J=2.0 Hz, 1H), 7.75 (d, J=7.8 Hz, 1H), 7.56 (t, J=8.0 Hz, 1H), 7.19-7.26 (m, 2H), 6.81 (dd, J=8.6, 1.2 Hz, 1H), 5.64 (s, 1H), 4.11 (d, J=2.0 Hz, 1H), 3.90-3.99 (m, 1H), 3.69-3.85 (m, 3H), 3.55 (td, J=6.4, 2.9 Hz, 1H), 2.33 (d, J=1.6 Hz, 3H); ESI-MS [M+H]$^+$ calcd for $C_{20}H_{20}N_2O_9H^+$ 433.12 found 433.2.

Example 36

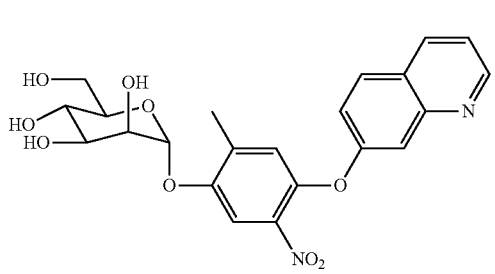

7-[4-(α-D-mannopyranosyloxy)-5-methyl-2-nitrophenoxy]quinoline was obtained in 40% yield following the same two-step $S_NAr$/deprotection procedure used to make Example 1, employing 7-hydroxyquinoline and using a modified volume of DMF (1.0 mL) and a reaction temperature of 25° C.

Formula: $C_{22}H_{22}N_2O_9$ Exact Mass: 458.13 Molecular Weight: 458.42

$^1$H NMR (400 MHz, methanol-$d_4$) δ ppm 8.94-9.05 (m, 2H), 8.30 (d, J=9.0 Hz, 1H), 8.03 (s, 1H), 7.85 (dd, J=7.8, 5.5 Hz, 1H), 7.68 (dd, J=9.2, 1.8 Hz, 1H), 7.32-7.40 (m, 2H), 5.68 (s, 1H), 4.10-4.17 (m, 1H), 3.95 (dd, J=9.4, 3.1 Hz, 1H), 3.70-3.85 (m, 3H), 3.56 (dd, J=8.8, 6.5 Hz, 1H), 2.36 (s, 3H); ESI-MS [M+H]$^+$ calcd for $C_{22}H_{22}N_2O_9H^+$ 459.14 found 459.2.

Example 37

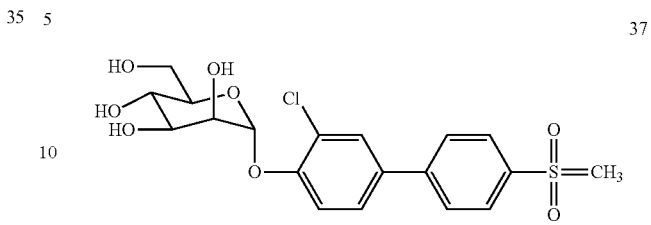

3-chloro-4'-(methylsulfonyl)biphenyl-4-yl α-D-mannopyranoside

The prepared 4-bromo-2-chlorophenyl 2,3,4,6-tetra-O-acetyl-α-D-mannopyranoside (108) and the commercially available 4-methylsulfonylphenylboronic acid were reacted via the standard Suzuki coupling procedure (1.5 h at 80° C.), followed by the acetate deprotection protocol (24 h at rt), to give the product in 76% yield.

Formula: $C_{19}H_{21}ClO_8S$ Exact Mass: 444.06 Molecular Weight: 444.88.

$^1$H NMR (400 MHz, methanol-$d_4$) δ ppm 7.91 (d, J=8.6 Hz, 2H), 7.75 (d, J=8.2 Hz, 2H), 7.67 (d, J=2.3 Hz, 1H), 7.52 (dd, J=8.8, 2.2 Hz, 1H), 7.39 (d, J=8.6 Hz, 1H), 5.53 (d, J=1.2 Hz, 1H), 4.02 (d, J=2.0 Hz, 1H), 3.91 (dd, J=9.4, 3.5 Hz, 1H), 3.59-3.72 (m, 3H), 3.50-3.57 (m, 1H), 3.05 (s, 3H); ESI-MS [M+Na]$^+$ calcd for $C_{19}H_{21}ClO_8SNa^+$ 467.05 found 467.2.

Example 38

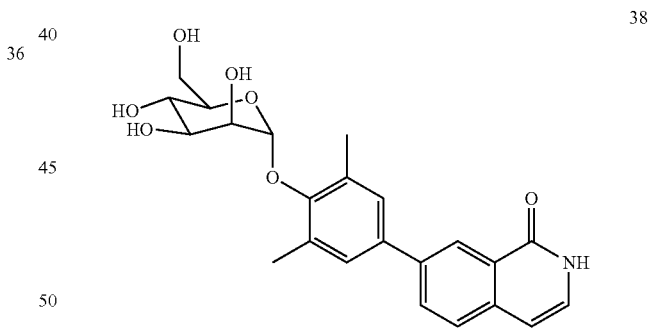

7-[4'-(α-D-mannopyranosyloxy)-3',5'-dimethylphenyl]-1 (2H)-iso-quinolinone was synthesized by a Suzuki coupling/ acetate deprotection procedure as detailed below.

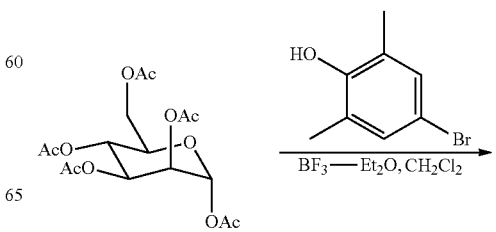

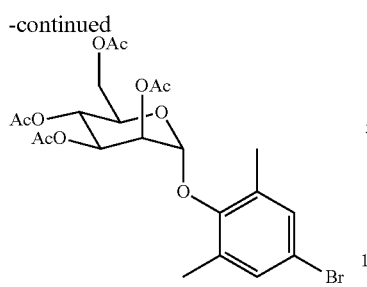

(2R,3R,4S,5S,6R)-2-(Acetoxymethyl)-6-(4-bromo-2,6-dimethylphenoxy)-tetrahydro-2H-pyran-3,4,5-triyl triacetate: To a solution of mannose pentaacetate and 4-bromo-2,6-dimethylphenol (4.6 g, 23.1 mmol) in $CH_2Cl_2$ (60 mL) was added $BF_3.OEt_2$ (47 wt %, 6 mL) dropwise at 0° C. The resulting mixture was stirred at 50° C. for 3 hours and then cooled to room temperature and poured into ice-water (100 mL). The mixture was extracted with $CH_2Cl_2$ (100 mL×3), and the combined organic layer was washed with saturated aqueous $NaHCO_3$ (100 mL), and brine (100 mL), then dried over anhydrous $Na_2SO_4$ and filtered. The filtrate was concentrated under vacuum and the residue was purified by silica gel chromatography, eluting with EtOAc in petroleum ether (0~50%) to afford the title compound (1.0 g, 25% yield) as a light red solid.

ESI-MS $[M+Na^+]$ calcd for $(C_{22}H_{27}BrO_{10}Na^+)$ 554.07, found 554.10.

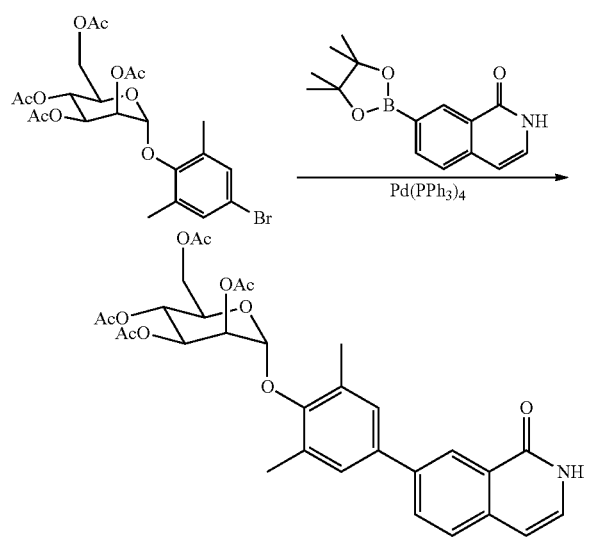

(2R,3R,4S,5S,6R)-2-(Acetoxymethyl)-6-(2,6-dimethyl-4-(1-oxo-1,2-dihydro-isoquinolin-7-yl)phenoxy)tetrahydro-2H-pyran-3,4,5-triyl triacetate To a solution of the product from the previous step (200 mg, 0.38 mmol) in dioxane/water (10 mL/2 mL) were added 7-(4,4,5,5-tetramethyl-1,3,2-dioxaborolan-2-yl)isoquinolin-1(2H)-one (112.3 mg, 0.41 mmol), $Cs_2CO_3$ (371.4 mg, 1.14 mmol) and $Pd(PPh_3)_4$ (21.4 mg, 0.02 mmol) at room temperature. The resulting mixture was purged with $N_2$ and stirred at 80° C. for 40 min. Upon completion, the reaction mixture was cooled to room temperature and concentrated under reduced pressure. The residue was purified by silica gel chromatography, eluted with MeOH in $CH_2Cl_2$ (0-20%) to afford the title compound (200 mg, contained de-Ac compound) as a light yellow solid.

ESI-MS $[M+H]^+$ calcd for $(C_{31}H_{33}NO_{11}H^+)$ 596.21, found 596.20.

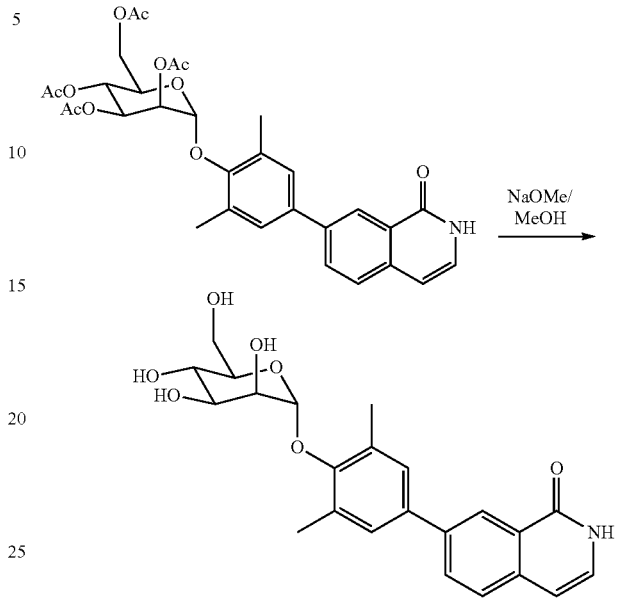

7-[4'-(α-D-mannopyranosyloxy)-3',5'-dimethylphenyl]-1(2H)-iso-quinolinone The product from the previous step (200 mg) was dissolved in MeOH (10 mL), and cooled to 0° C. NaOMe in MeOH (1M) was added dropwise until a pH of 9-10 was achieved. The reaction mixture was stirred at this temperature for 5 min and then stirred at room temperature for 1 h. The reaction mixture was quenched with water (0.2 mL) and concentrated in vacuo. The residue was purified by Prep-HPLC [Column: XBridge Prep C18 OBD Column, 5 um, 19*150 mm; Mobile Phase A: Water (10 mmol/L $NH_4HCO_3$), Mobile Phase B: ACN; Flow rate: 20 mL/min; Gradient: 15% B to 25% B in 15 min; 254 nm; Rt: 14.78 min] to afford the product (25.4 mg, 16% for two steps) as a white solid.

Formula: $C_{23}H_{25}NO_7$ Exact Mass: 427.16 Molecular Weight: 427.45.

Analytical data: $^1H$ NMR (400 MHz, Methanol-$d_4$) δ 8.49 (d, J=1.2 Hz, 1H), 7.96 (dd, J=8.4 Hz, 1.6 Hz, 1H), 7.70 (d, J=8.4, 1H), 7.39 (s, 2H), 7.17 (d, J=7.2 Hz, 1H), 6.69 (d, J=6.8 Hz, 1H), 5.08 (d, J=1.2 Hz, 1H), 4.29-4.27 (m, 1H), 4.10-4.05 (m, 1H), 3.99 (dd, J=5.6 Hz, 3.2 Hz, 1H), 3.90-3.77 (m, 3H), 2.40 (s, 6H). ESI-MS $[M+H]^+$ calcd for $(C_{23}H_{25}NO_7H^+)$ 428.17, found 428.30.

Example 39

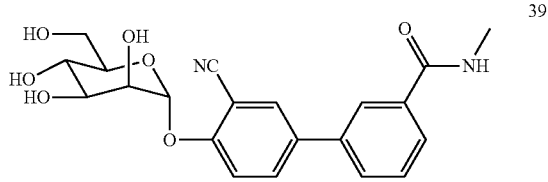 [SMILES: CNC(=O)c1cccc(-c2ccc(OC3OC(CO)C(O)C(O)C3O)c(C#N)c2)c1]

4'-(α-D-mannopyranosyloxy)-3'-cyano-N-methyl-1,1'biphenyl-3-carboxamide

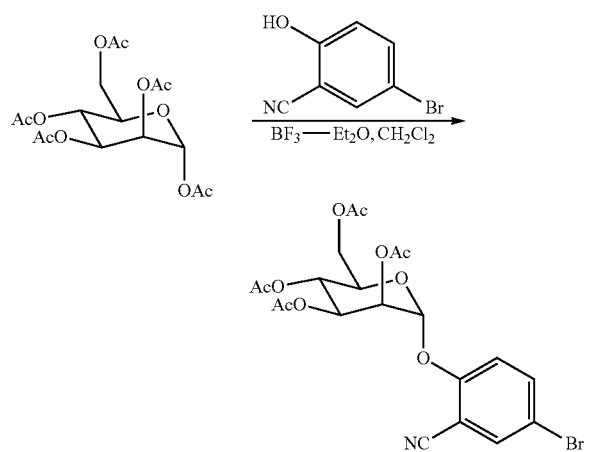

(2R,3R,4S,5S,6R)-2-(Acetoxymethyl)-6-(4-bromo-2-cyanophenoxy)tetrahydro-2H-pyran-3,4,5-triyl triacetate To a solution of (2R,3S,4S,5R,6R)-6-(acetoxymethyl)tetrahydro-2H-pyran-2,3,4,5-tetrayl tetraacetate (2.0 g, 5.13 mmol) and 5-bromo-2-hydroxybenzonitrile (1.12 g, 6.16 mmol) in $CH_2Cl_2$ (10 mL) was added $BF_3$ in $Et_2O$ (2 mL, 41%-47 wt %) at 0° C. under nitrogen atmosphere. The resulting mixture was stirred for 2 h at 35° C. Upon completion, the reaction was quenched with water, extracted with $CH_2Cl_2$ (25 mL×3), the organic layer was dried over $Na_2SO_4$ and filtered. The filtrate was concentrated under reduced pressure and the residue was purified by silica gel chromatography, eluting with ethyl acetate in petroleum ether (0-25%) to afford the title compound (1.8 g, 78%) as yellow oil.

ESI-MS $[M+NH_4]^+$ calculated for $(C_{21}H_{22}BrNO_{10}NH_4^+)$ 545.08, found 545.00, 546.95.

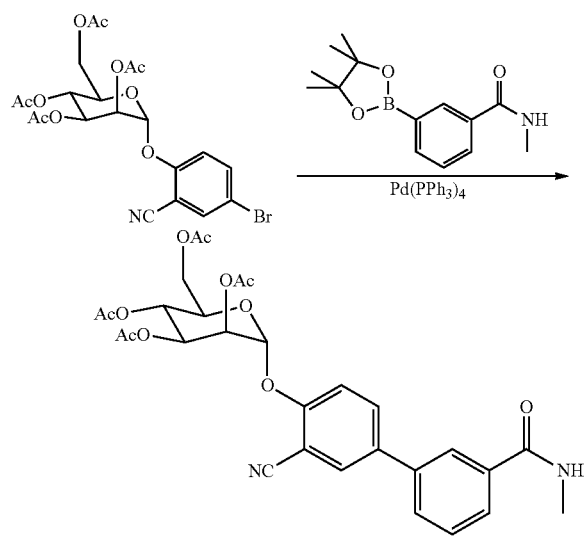

(2R,3R,4S,5S,6R)-2-(Acetoxymethyl)-6-((3-cyano-3'-(methylcarbamoyl)-[1,1'-biphenyl]-4-yl)oxy)tetrahydro-2H-pyran-3,4,5-triyl triacetate A mixture of (2R,3R,4S,5S,6R)-2-(acetoxymethyl)-6-(4-bromo-2-cyanophenoxy) tetrahydro-2H-pyran-3,4,5-triyl triacetate (400 mg, 0.76 mmol,), N-methyl-3-(4,4,5,5-tetramethyl-1,3,2-dioxaborolan-2-yl)benzamide (240 mg, 0.91 mmol), cesium carbonate (742 mg, 2.28 mmol) and $Pd(PPh_3)_4$ (44 mg, 0.038 mmol) in dioxane/water (5 mL/1 mL) was stirred for 1.5 h at 80° C. under $N_2$. Upon completion, the reaction was concentrated under reduced pressure. The residue was purified by silica gel chromatography, eluting with methanol in dichloromethane (0~20%) to afford the title product (140 mg, crude, contained de-Ac compound) as a light brown solid.

ESI-MS $[M+NH_4]^+$ calculated for $(C_{29}H_{30}N_2O_{11}NH_4^+)$ 600.22, found 600.10.

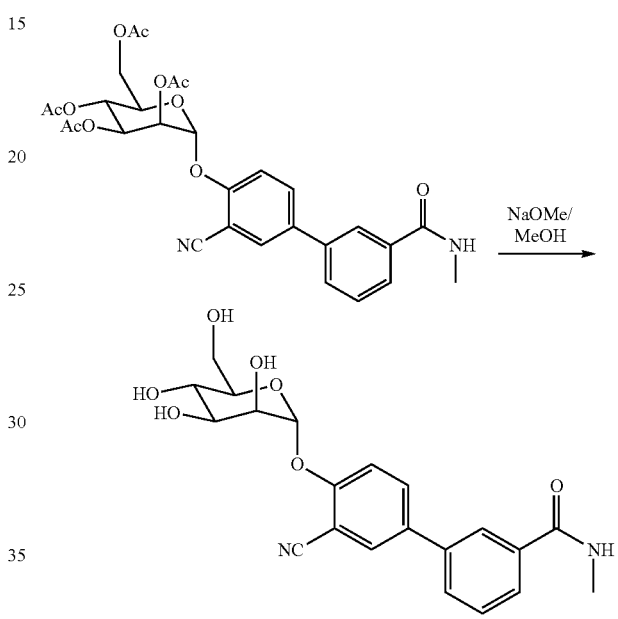

4'-(α-D-mannopyranosyloxy)-3'-cyano-N-methyl-1,1'biphenyl-3-carboxamide (2R,3R,4S,5S,6R)-2-(acetoxymethyl)-6-((3-cyano-3'-(methylcarbamoyl)-[1,1'-biphenyl]-4-yl)oxy)tetrahydro-2H-pyran-3,4,5-triyl triacetate (140 mg, crude) obtained above was dissolved in methanol (4 mL) and to the solution was dropwise added $NaOCH_3$ in $CH_3OH$ (0.02 N) at 0° C. until a pH of 9-10 was achieved. The reaction mixture was stirred for 1 h at 25° C. and then quenched with water (4 drops) and concentrated under reduced pressure. The residue was purified by prep-HPLC [Column: XBridge Prep OBD C18 Column 30×150 mm 5 um; Mobile Phase A: Water (10 mmol/L $NH_4HCO_3$), Mobile Phase B: ACN; Flow rate: 60 mL/min; Gradient: 5% B to 40% B in 7 min; 220 nm; Rt: 5.4 min] to afford the title compound (35 mg, 11% for two steps) as a white solid.

Formula: $C_{21}H_{22}N_2O_7$ Exact Mass: 414.14 Molecular Weight: 414.41.

Analytical data: $^1H$ NMR (300 MHz, Methanol-$d_4$) δ 8.05 (t, J=1.5 Hz, 1H), 7.99-7.92 (m, 2H), 7.83-7.77 (m, 2H), 7.60-7.53 (m, 2H), 5.72 (d, J=1.8 Hz, 1H), 4.13 (dd, J=3.3 Hz, 1.8 Hz, 1H), 4.01 (dd, J=9.6 Hz, 3.3 Hz, 1H), 3.83-3.69 (m, 3H), 3.63-3.57 (m, 1H), 2.95 (s, 3H). ESI-MS $[M+H]^+$ calculated for $(C_{21}H_{22}N_2O_7H^+)$ 415.15, found 415.05.

Biological Activity Assay

The activity of the compounds in Examples 1-39 as FimH inhibitors is illustrated in the following assay(s). The other compounds listed above, which have not yet been tested, are predicted to have activity in these assay(s) as well.

HAI Assay The hemagglutination inhibition (HAI) assay was performed with UTI89 bacteria and guinea pig red blood cells, as previously described (S. J. Hultgren, W. R. Schwan, A. J. Schaeffer, J. L. Duncan *Infect. Immun.* 1986, 54, 613-620). Results are listed in Table 1. Compounds not listed were not tested.

TABLE 1

| Example # | HAI titer EC$_{>90}$, μM |
|---|---|
| 1 | 0.125 |
| 2 | 0.032 |
| 3 | 0.062 |
| 4 | 0.032 |
| 5 | 0.062 |
| 6a | 0.062 |
| 6b | 0.062 |
| 7 | 0.25 |
| 8 | 0.25 |
| 9 | 0.032 |
| 10 | 16 |
| 11 | 0.032 |
| 12 | 0.062 |
| 13 | 0.125 |
| 14 | 0.02 |
| 15 | 0.062 |
| 16 | 0.125 |
| 17 | 0.062 |
| 18 | 0.125 |
| 19 | 2 |
| 20 | 2 |
| 21 | 0.032 |
| 22 | 2 |
| 23 | 0.032 |
| 24 | 0.25 |
| 25 | 0.024 |
| 26 | 0.043 |
| 27 | 0.032 |
| 28 | 0.15 |
| 29 | 1 |
| 30 | 1.5 |
| 31 | 0.5 |
| 32 | 0.5 |
| 33 | 0.25 |
| 34 | 0.125 |
| 35 | 1 |
| 36 | 0.5 |
| 37 | 0.15 |
| 38 | 0.266 |
| 39 | 0.188 |

Biofilm Assay The biofilm inhibition assay was performed with UTI89 bacteria as previously described (L. Cegelski, J. S. Pinkner, N. D. Hammer, C. K. Cusumano, C. S. Hung, E. Chorell, V. Aberg, J. N. Walker, P. C. Seed, F. Almqvist, M. R. Chapman, S. J. Hultgren Nature Chem. Biol. 2009, 5, 913-919). Results are listed in Table 2. Compounds not listed were not tested.

TABLE 2

| Example # | Biofilm prevention IC$_{50}$, μM |
|---|---|
| 2 | 0.524 |
| 4 | 0.32 |
| 14 | 0.336 |
| 21 | 0.247 |

Differential scanning fluorimetry (DSF) Purified FimHL (10 μM) in the absence or presence of mannoside (100 μM) was combined with 5× SYPRO Orange in a 50 μl reaction mixture buffered in 20 mM HEPES pH 7.5, 150 mM NaCl (HBS) and 0.4% DMSO. Binding equilibria were established by allowing the reaction mixtures to incubate at 23° C. for 30 min. These reaction mixtures were then placed in 96-well clear-bottom PCR plates and subjected to a melt curve from 20-90° C. in 0.5° C. increments of 15 seconds, each followed by a fluorescence read of the "HEX" channel in a Bio-Rad CFX96 thermocycler (Bio-Rad, Hercules, Calif.). Melt curves were fitted to the Boltzmann equation $(y=A2+(A1-A2)/(1+\exp((x-x_o)/dx))$ where $x_o$ is the $T_m$) to determine the melting temperature ($T_m$) using GraphPad Prism 6 (San Diego Calif.). Melting temperatures are represented as the mean and standard error of two biological replicates, each of which consisted of three technical replicates. The results are shown in Table 3. Compounds not listed were not tested.

TABLE 3

| Example # | DSF Melting Temp (° C.) |
|---|---|
| 2 | 74.4 |
| 4 | 74.1 |
| 14 | 75.1 |
| 21 | 75.0 |

In Vivo Assay

Animal infections Bacteria were grown under type 1 pilus-inducing conditions (2×24 hours at 37° C. statically in LB). The bacteria were harvested and resuspended to an A600 (absorbance at 600 nm) of 0.5 in PBS. Eight-week-old C3H/HeN (Harlan) female mice were anesthetized by inhalation of isoflurane and infected via transurethral catheterization with 50 μl of the bacterial suspension, resulting in $1\times10^7$ to $2\times10^7$ inoculum. At 6 hours after infection, mice were killed by cervical dislocation under anesthesia and the bladders were immediately harvested and processed as described below.

Chronic infection (as described in Cusumano, C. K. et al, *Sci Transl Med* 2011, 3) Mice were infected with UTI89, and the infection was allowed to continue for 2 weeks. At 12 days after infection, urine was collected and titered to determine which mice were chronically infected (urine titers $>10^6$). At 2 weeks after infection, chronically infected mice were treated orally with mannoside Example 15 (50 mg/kg). Six hours after treatment, mice were killed and bladders were aseptically removed and homogenized in 1 ml of PBS and serially diluted and plated them onto LB agar plates. CFU were enumerated after 16 hours of growth at 37° C., to determine tissue titers.

Figure 2:
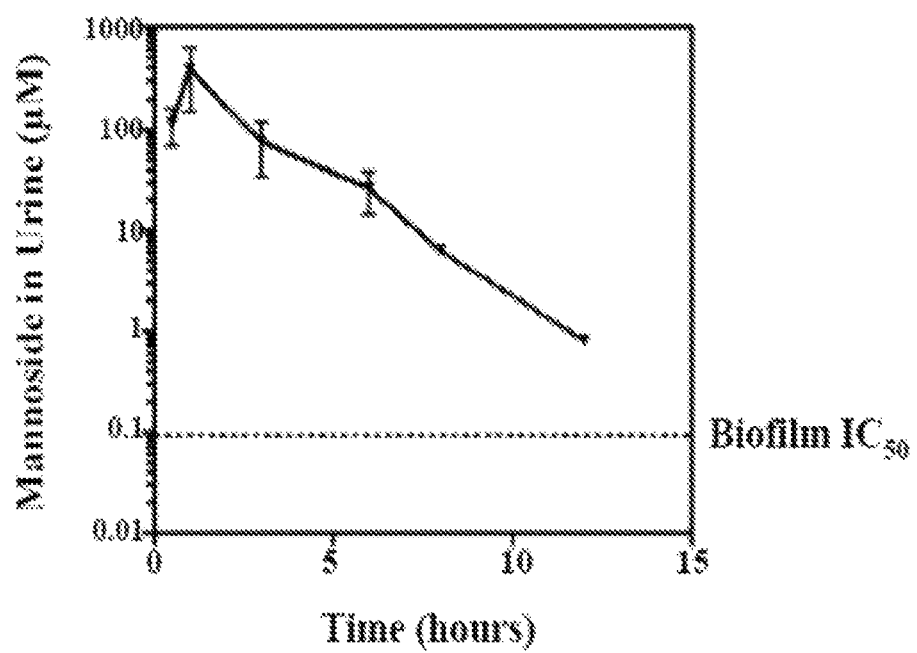
FIG. 2 provides concentrations of mannosides in urine collected at 30 min and 1, 3, 6, 8 and 12 hours after treatment, as described in the in vivo assay.

Pharmacokinetic analysis For oral dosing, 100 μl of a solution of mannoside Example 15 in 10% Cyclodextrin [10 mg/ml (50 mg/kg)] was inoculated with a gavage needle into the mouse stomach. Urine was collected at 30 min and 1, 3, 6, 8 and 12 hours after treatment, see FIG. 1. An equal volume of 10 μM internal standard N-methyl-4'-((2R,3S,4S,5S,6R)-3,4,5-trihydroxy-6-(hydroxymethyetetrahydro-2H-pyran-2-yloxy)biphenyl-3-carboxamide was added to the urine. Mannosides were extracted from the urine by loading on C18 columns (100 mg, Waters), washing with 30% methanol, and eluting with 60% methanol. Vacuum-concentrated eluates were analyzed using an AB Sciex API-4000 QTrap (AB Sciex, Foster City, Calif.) with a lower heated capillary temperature of 190° C. and a gradient as follows: Solvent B (80% acetonitrile in 0.1% formic acid) was held constant at 5% for 5 min, increased to 44% B by 45 min, and then to a 95% B by 65 min Selected reaction monitoring (SRM) mode quantification was performed with collision gas energy of 30% for the following MS/MS transitions [precursor mass/charge ratio (m/z)/product m/z]: Example 15: 397/235, see FIG. 2. Absolute quantification was achieved by comparison to a calibration curve.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. The compound of formula III, wherein formula III has the structural formula:

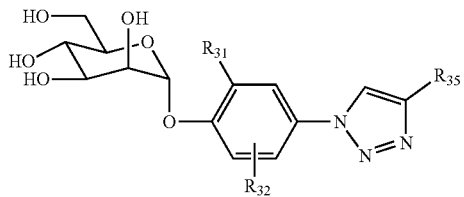

(III)

or a salt or ester thereof, wherein:
$R_{31}$ is chosen from $CH_3$, $CF_3$, $OCH_3$, OAc, halogen, $NH_2$, $NHR_{34}$;
$R_{32}$ is chosen from H, $NO_2$, $NH_2$, $NHR_{34}$;
each $R_{34}$ is independently chosen from alkyl, aryl, and heteroaryl;
and $R_{35}$ is an alkyl, cycloalkyl, heterocycloalkyl, aryl or heteroaryl group optionally substituted with one or more of the following:
halogen, CN, COOH, $NH_2$, $NO_2$, and $C_{1-4}$alkyl.

2. A method of treatment of a FimH-mediated disease comprising the administration of a therapeutically effective amount of a compound as recited in claim 1 to a human patient in need thereof, wherein said disease is chosen from a bacterial infection, Crohn's disease (CD), and Inflammatory Bowel Disease (IBD).

3. The method as recited in claim 2 wherein said bacterial infection is a urinary tract infection.

4. The method as recited in claim 3 wherein said urinary tract infection is recurrent.

5. The method as recited in claim 3 wherein said urinary tract infection is chronic.

6. The method as recited in claim 3 wherein said bacterial infection is an antibiotic-resistant bacterial infection.

7. The method as recited in claim 2 wherein said disease is Crohn's disease.

* * * * *

UNITED STATES PATENT AND TRADEMARK OFFICE
CERTIFICATE OF CORRECTION

PATENT NO. : 10,738,070 B2
APPLICATION NO. : 16/087305
DATED : August 11, 2020
INVENTOR(S) : Janetka et al.

Page 1 of 1

It is certified that error appears in the above-identified patent and that said Letters Patent is hereby corrected as shown below:

In the Specification

Column 1, Line 7, add the following paragraph:
STATEMENT REGARDING FEDERALLY SPONSORED RESEARCH OR DEVELOPMENT
This invention was made with government support under Award Numbers R43AI106112 and R44AI106112 awarded by the National Institute of Allergy and Infectious Diseases of the National Institutes of Health. The government has certain rights in the invention.

Signed and Sealed this
Twenty-fourth Day of August, 2021

Drew Hirshfeld
*Performing the Functions and Duties of the*
*Under Secretary of Commerce for Intellectual Property and*
*Director of the United States Patent and Trademark Office*